(12) United States Patent
Schottek et al.

(10) Patent No.: US 7,285,608 B2
(45) Date of Patent: Oct. 23, 2007

(54) METALLOCENE LIGANDS, METALLOCENE COMPOUNDS AND METALLOCENE CATALYSTS, THEIR SYNTHESIS AND THEIR USE FOR THE POLYMERIZATION OF OLEFINS

(75) Inventors: Joerg Schottek, Frankfurt (DE); Nicola Stefanie Paczkowski, Loveland, OH (US); Andreas Winter, Neuleiningen (DE); Thorsten Sell, Frankfurt (DE)

(73) Assignee: Novolen Technology Holdings C.V., The Hague (NL)

( * ) Notice: Subject to any disclaimer, the term of this patent is extended or adjusted under 35 U.S.C. 154(b) by 86 days.

(21) Appl. No.: 10/828,814

(22) Filed: Apr. 21, 2004

(65) Prior Publication Data

US 2005/0239979 A1    Oct. 27, 2005

(51) Int. Cl.
*C08F 4/52* (2006.01)
*C08F 4/76* (2006.01)

(52) U.S. Cl. ............... 526/160; 526/170; 526/941; 526/943; 556/53; 556/52; 556/51; 502/103

(58) Field of Classification Search ............ 526/160, 526/170, 943; 556/43, 42, 53, 52, 11
See application file for complete search history.

(56) References Cited

U.S. PATENT DOCUMENTS

| | | | | |
|---|---|---|---|---|
| 4,752,597 A | | 6/1988 | Turner | 502/104 |
| 4,985,576 A | * | 1/1991 | Rohrmann et al. | 556/435 |
| 5,017,714 A | | 5/1991 | Welborn, Jr. | 556/12 |
| 5,243,001 A | | 9/1993 | Winter et al. | 526/127 |
| 5,612,462 A | | 3/1997 | Lisowsky | 534/15 |
| 5,679,812 A | | 10/1997 | Winter et al. | 556/7 |
| 5,770,753 A | | 6/1998 | Küber et al. | 556/11 |
| 5,840,950 A | | 11/1998 | Fischer et al. | 556/11 |
| 5,912,373 A | | 6/1999 | Fischer et al. | 556/7 |
| 5,945,367 A | * | 8/1999 | Thiele et al. | 502/155 |
| 5,990,331 A | | 11/1999 | Winter et al. | 556/9 |
| 6,060,572 A | | 5/2000 | Gillis et al. | 526/335 |
| 6,117,957 A | | 9/2000 | Ewen | 526/160 |
| 6,184,402 B1 | * | 2/2001 | Yamazaki et al. | 556/11 |
| 6,365,763 B1 | * | 4/2002 | Winter et al. | 556/11 |
| 6,960,676 B2 | * | 11/2005 | Rix et al. | 556/87 |
| 2003/0149199 A1 | | 8/2003 | Schottek et al. | 526/126 |

FOREIGN PATENT DOCUMENTS

| | | |
|---|---|---|
| EP | 0 320 762 B1 | 12/1988 |
| EP | 0 416 815 B1 | 8/1990 |
| EP | 0 537 686 A1 | 10/1992 |
| EP | 0 669 340 B1 | 8/1994 |
| EP | 0 780 396 B1 | 12/1996 |
| WO | WO 02/14384 A | 2/2002 |
| WO | WO 03/051943 | 6/2003 |

OTHER PUBLICATIONS

Alt, Helmut G. et al., "ansa-Metallocene complexes of type . . . self-immobilized catalysts for ethylene polymerization", *J. of Organometallic Chemistry*, 562(2), 229-253 (1998).

Guo, Dawei et al., "Molecular modeling on the prediction of silolene-bridged indenyl metallocene catalyst for isotactic polypropylene", J. of Polymer Science, 38(12), 2232-2238 (2000).

\* cited by examiner

*Primary Examiner*—David W. Wu
*Assistant Examiner*—Rip A. Lee
(74) *Attorney, Agent, or Firm*—Dilworth & Barrese, LLP

(57) ABSTRACT

A catalyst system includes a metallocene compound having the formula $R^9 L^1 L^2 M^1 R^1 R^2$ wherein $R^9$ is a bridge between ligands $L^1$ and $L^2$ and $M^1$ is a metal of Group IVB of the Periodic Table such as titanium, zirconium and hafnium and $R^1$ and $R^2$ can be hydrogen or aliphatic or aromatic groups. Bridge $R^9$ can include silicon, germanium or tin. The metallocene compound of the invention as synthesized has a racemic to meso isomer ratio of greater than 5 to 1, thereby precluding the need for subsequent separation of the meso isomer.

71 Claims, No Drawings

METALLOCENE LIGANDS, METALLOCENE COMPOUNDS AND METALLOCENE CATALYSTS, THEIR SYNTHESIS AND THEIR USE FOR THE POLYMERIZATION OF OLEFINS

BACKGROUND

1. Field of the Invention

The present invention relates to substituted ligands and to a process for the preparation of such substituted ligands, to metallocenes comprising such substituted ligands and to a process for the economical preparation of such metallocenes in pure isomeric form, to highly active catalyst systems comprising such metallocenes, which can advantageously be used in olefin polymerization and to a process for the economical preparation of such catalyst systems, and to a process using such catalyst systems for the polymerization and copolymerization of olefins and to polymers which are prepared using such catalyst systems.

2. Background of the Art

Processes for preparing polyolefins using soluble, homogeneous catalyst systems comprising a transition metal component of the metallocene type and a cocatalyst component of the type of an aluminoxane, a Lewis acid or an ionic compound are well known. In polymerizations using such soluble, homogeneous catalyst systems, heavy deposits are formed on reactor walls and the stirrer if the polymer is obtained as a solid. These deposits are formed by agglomeration of the polymer particles whenever metallocene and/or cocatalyst are present in dissolved form in the suspension. The deposits in the reactor systems quickly reach considerable thickness and have a high strength. They prevent heat exchange to the cooling medium and therefore have to be removed regularly. Such homogeneous catalyst systems cannot be used industrially in liquid monomer or in the gas phase.

To avoid deposit formation in the reactor, supported catalyst systems in which the metallocene and/or the aluminum compound serving as cocatalyst is/are fixed on an inorganic support material have been proposed. As an example, EP-A-0 576 970 discloses metallocenes and corresponding supported catalyst systems. At industrially relevant polymerization temperatures of from 50° C. to 80° C., such supported catalyst systems give polymers, in particular polypropylenes, having melting points of at most 156° C.

In general, typical values for metallocene catalyst systems are in the region of 130 to 160° C. While the polypropylenes with lower melting points are usable for applications, where higher transparency, impact resistance or sealing behavior are required as dominating properties (for example thin wall injection molding, fiber, film), the polypropylenes with higher melting points are used for applications, where higher stiffness is the dominating requirement.

Metallocenes may be used as catalyst components for the polymerization and copolymerization of olefins, possibly in combination with one or more cocatalysts. In particular, halogen-containing metallocenes are used as catalyst precursors, which can be converted, for example, by an aluminoxane, to polymerization-active cationic metallocene complexes (EP-A-129,368).

The production of metallocenes is well known in itself (U.S. Pat. No. 4,752,597; U.S. Pat. No. 5,017,714; EP-A-320,762; EP-A-416,815; EP-A-537,686; EP-A-669,340; H. H. Brintzinger et al.; *Angew. Chem.*, 107 (1995), 1255; H. H. Brintzinger et al.; *J. Organomet. Chem.*, 232 (1982), 233). They may be produced, for example, by reacting cyclopentadienyl metal compounds with halides of transition metals, such as titanium, zirconium, and hafnium.

It is also well known that basic properties of the metallocenes, such as polymerization activity, stereoselectivity, regioselectivity, and maximum achievable polymer molecular weight can be systematically controlled by specific substitution patterns of the ligand sphere. For example, the molecular weight $M_w$ of the polypropylene produced with the use of dimethylsilylbis(2-R-indenyl)zirconium dichlorides is described with the typical values for PP waxes of 37,500 g/mole (R=H) to 197,500 g/mole (R=methyl) (EP 0 485 822 B1, U.S. Pat. No. 5,243,001).

With respect to controlling stereoselectivity, regioselectivity, and polymer molecular weight, the substitution of an indenyl ligand in the 4-position has also been found to be effective. For example, EP 0 576 970 (U.S. Pat. No. 5,770,753) comparatively describes the metallocenes dimethylsilylbis(2-ethyl-1-indenyl)zirconium dichloride (polymer molecular weight of 450,000 g/mole and polymer melting point of 147° C. as measures of the stereo- and regioselectivity) and dimethylsilylbis(2-ethyl-4-phenyl-1-indenyl)zirconium dichloride (polymer molecular weight of 1,790,000 g/mole and polymer melting point of 162° C.).

The controlling effect of units that bridge the idenyl ligands has also been described. For example, EP 0 284 708 B1 (U.S. Pat. No. 6,117,957) describes a method for controlling polymer molecular weight and polymer melting point by bridge variation ("It has been discovered that changing the structure and composition of the bridge leads to changes in the melting points and molecular weights of the polymer products.") Similar results were reported in EP 0 336 128 B1 (U.S. Pat. No. 5,679,812) and EP 0 344 887 (U.S. Pat. No. 5,017,714).

The metallocenes with standard bridges, such as the dimethylsilyl bridge, which have been described in the literature and in some cases are already being used in industry, generally have tremendous disadvantages. For example, metallocenes bridged in this way can be isolated in pure racemic ("rac") form only with unacceptably high yield losses and high expense of by-products, and the support-production step necessary for the use of metallocenes in all modern polymerization processes for preventing incrustation is made even more complicated by the unsatisfactory solubility behavior of these compounds.

However, to use metallocenes in the polymerization of olefins, the preparation of the isomerically pure racemic form is absolutely necessary, since the corresponding meso form produces undesired atactic polypropylene ("PP"). The isomerically pure racemic form is understood to mean a rac:meso ratio of greater than 5:1 preferably of at least 10:1, more preferred of at least 15:1 and most preferred of at least 20:1.

The separation of the metallocene and inorganic by-products is usually carried out by dissolving the metallocene with organic solvents, such that the inorganic by-products can be separated as practically insoluble components. Toluene and dichloromethane are used especially often as solvents for this purpose, but other solvents are also used, such as tetrahydrofuran, diethyl ether, and aliphatic, aromatic, and chlorinated hydrocarbons. The organometallic by-products are usually separated in a second step, in which the crude product is dissolved in a solvent and then depleted of undesired organometallic by-products, e.g., isomers, by fractional crystallization or fractional precipitation. The disadvantage of these methods is that many metallocenes are only moderately soluble in common organic solvents and therefore require large amounts of solvent, large filtration equipment, and a great deal of time. In addition, large amounts of solvents that are toxic or environmentally controversial are often used. Since the inorganic by-products are often obtained in very fine distribution, filtration times can become very long, even if filter aids are added and the filtration is carried out at elevated pressure. To be able to isolate the metallocene as completely as possible from the filtrate, it is usually necessary to distil off the solvent. This presents the problem of the limited stability of these types of metallocene solutions towards impurities, such as traces of moisture, bases, protic compounds, and thermal stress. Another point is that the large number of reaction steps makes it quite uneconomical in some cases. This problem is exacerbated by the fact that the compounds formed in the individual purification steps, some of which contain educts, cannot be isolated, since they are poorly separable components in mixtures.

Although methods for depleting inorganic and organometallic by-products are described in EP 0 780 396, economical utilization is not possible here, because these purification steps result in the loss of valuable educts and end products, and the yield of the desired end product is ultimately reduced by these losses to an extent that is no longer acceptable.

Therefore, the object of the invention is to eliminate the disadvantages of the state of the art and to make available compounds that are more soluble and have the same or an improved catalytic property profile and/or make available a direct synthesis, which yields the desired isomer with the use of surprising synergistic effects of alternative bridging concepts, suitable ligand substitution patterns, and ligand substituents, and at the same time is able to dispense with the large number of reaction steps and, in addition, produce a decisive economic advantage.

The object of the present invention is achieved by more highly soluble metallocenes and/or by a process for producing isomerically pure metallocenes on the basis of specially bridged and substituted metallocenes.

Another object of the present invention is to provide supported metallocene catalysts using such substituted and bridged metallocenes and to provide an environmentally friendly and economical process for preparing polyolefins under industrially relevant polymerization conditions using the catalyst systems of this invention.

We have found that this object is achieved by a supported catalyst system comprising at least one substituted and specifically bridged metallocene, at least one cocatalyst, at least one support and, if desired, at least one metal compound and further one additive component. According to the present invention, the catalyst system is prepared by mixing at least one substituted and specifically bridged metallocene, at least one cocatalyst, at least one support and if desired at least one metal compound and one further additive component.

As substituted and specifically bridged metallocene component of the catalyst system of the present invention, use is made of at least one compound of the formula 1a below, $$R^9 L^1 L^2 M^1 R^1 R^2 \qquad \text{(Formula 1a)}$$

where $L^1$ and $L^2$ are identical or different and are each a substituted mononuclear or polynuclear hydrocarbon radical or (a) hetero atom(s) containing hydrocarbon radical(s), for example substituted cyclopentadienyl, indenyl, tetrahydroindenyl, azurenyl, fluorenyl, azapentalenyl, thiapentalenyl or oxapentalenyl, which can form a sandwich structure with the central atom $M^1$, $R^1$ and $R^2$ are identical or different and are each a hydrogen atom, an alkyl group of from 1 to about 10 carbon atoms, an alkoxy group of from 1 to about 10 carbon atoms, an aryl group of from 6 to about 20 carbon atoms, an aryloxy group of from about 6 to about 10 carbon atoms, an alkenyl group of from 2 to about 10 carbon atoms, an OH group, a halogen atom, or a $NR_2^{32}$ group, where $R^{32}$ is an alkyl group of from 1 to about 10 carbon atoms or an aryl group of from 6 to about 14 carbon atoms, and $R^1$ and $R^2$ can form one or more ring system(s), $M^1$ is a metal of Group IVb of the Periodic Table of the Elements, $R^9$ is a bridge between the ligands $L^1$ and $L^2$,

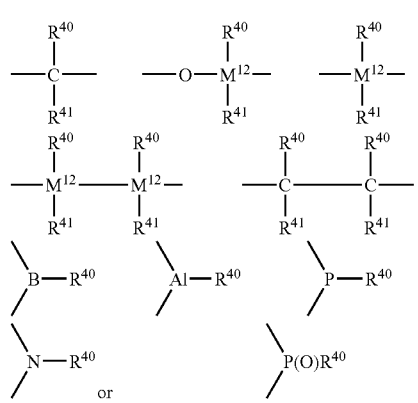

where $R^{40}$ and $R^{41}$, even when bearing the same index, can be identical or different and are each a $C_2$-$C_{40}$ group such as an alkyl group having from 2 to about 30 carbon atoms, a fluoroalkyl group of from 2 to about 10 carbon atoms, an alkoxy group of from 2 to about 10 carbon atoms, an aryloxy group of from 6 to about 10 carbon atoms, an alkenyl group of from about 3 to about 10 carbon atoms, an arylalkyl group of from 7 to about 40 carbon atoms, an alkylaryl group of from 7 to about 40 carbon atoms, a substituted or unsubstituted alkylsilyl or arylsilyl group, or an arylalkenyl group of from 8 to about 40 carbon atoms. $R^{40}$ and $R^{41}$ together with the atoms connecting them can form one or more cyclic systems and/or $R^{40}$ and $R^{41}$ can contain additional hetero atoms (i.e., non-carbon atoms) like Si, B, Al, O, S, N or P or halogen atoms like Cl or Br, and/or if $R^{40}$ and $R^{41}$ are different and $R^{40}$ is a hydrocarbon group of from about 4 to about 40 carbon atoms, $R^{41}$ can be a hydrocarbon group of from 1 to about 40 carbon atoms, $M^{12}$ is silicon, germanium or tin, and $R^9$ may also link two units of the formula 1a to one another.

In formula 1a it is preferred that $L^1$ is a substituted cyclopentadienyl, indenyl, tetrahydroindenyl, azurenyl, fluorenyl, azapentalenyl, thiapentalenyl or oxapentalenyl, which can form a sandwich structure with the central atom $M^1$, and $L^2$ is a substituted indenyl, tetrahydroindenyl, azurenyl, fluorenyl, azapentalenyl, thiapentalenyl or oxapentalenyl, which can form a sandwich structure with the central atom $M^1$, and the bridging unit $R^9$ is $R^{40}R^{41}Si=$, $R^{40}R^{41}Ge=$, $R^{40}R^{41}C=$ or $-(R^{40}R^{41}C-CR^{40}R^{41})-$, where $R^{40}$ and $R^{41}$ are identical or different and are each a hydrocarbon group of from 2 to about 30 carbon atoms, in particular an alkyl group of from 2 to about 30 carbon atoms, an arylalkyl group of from 7 to about 14 carbon atoms, an alkylaryl group of from 7 to 14 carbon atoms. If $R^{40}$ and $R^{41}$ are different and $R^{40}$ is a hydrocarbon group of from about 4 to about 40 carbon atoms, $R^{41}$ can be a hydrocarbon group of from 1 to about 30 carbon atoms.

In formula 1a it is very particularly preferred that $L^1$ and $L^2$ are identical or different and are each a substituted indenyl, azurenyl, fluorenyl, azapentalenyl, thiapentalenyl or oxapentalenyl, which can form a sandwich structure with the central atom $M^1$, and the bridging unit $R^9$ is $R^{40}R^{41}Si=$ or $R^{40}R^{41}Ge=$, where $R^{40}$ and $R^{41}$ are identical or different and are propyl, butyl, pentyl, hexyl, heptyl, octyl, nonyl, decyl, undecyl, dodecyl, cyclo-pentyl, cyclo-pentadienyl or cyclohexyl. If $R^{40}$ and $R^{41}$ are different and $R^{40}$ is butyl, pentyl, hexyl, heptyl, octyl, nonyl, decyl, undecyl, dodecyl, cyclopentyl, cyclopentadienyl or cyclohexyl, $R^{41}$ can be methyl, ethyl, propyl, butyl, pentyl, hexyl, heptyl, octyl, nonyl, decyl, undecyl, dodecyl, cyclopentyl, cyclopentadienyl or cyclohexyl.

More preferred, as the substituted and specifically bridged metallocene component of the catalyst system of the present invention, use is made of at least one compound of the formula 1b below

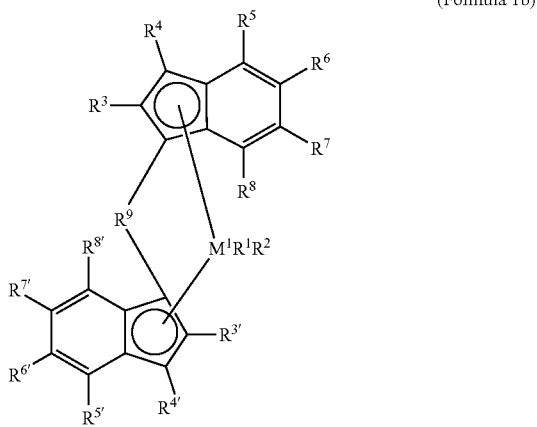

(Formula 1b)

where the substituents and indices have the following meanings:

$M^1$ is a metal of Group IVb of the Periodic Table of the Elements, $R^1$ and $R^2$ are identical or different and are each a hydrogen atom, an alkyl group of from 1 to about 10 carbon atoms, an alkoxy group of from 1 to about 10 carbon atoms, an aryl group of from 6 to about 20 carbon atoms, an aryloxy group of from 6 to about 10 carbon atoms, an alkenyl group of from 2 to about 10 carbon atoms, an OH group, a halogen atom, or a $NR_2^{32}$ group, where $R^{32}$ is an alkyl group of from 1 to about 10 carbon atoms or an aryl group of from 6 to about 14 carbon atoms, or $R^1$ and $R^2$ together can form one or more ring system(s), $R^3$, $R^4$, $R^5$, $R^6$, $R^7$, $R^8$ and also $R^{3'}$, $R^{4'}$, $R^{5'}$, $R^{6'}$, $R^{7'}$ and $R^{8'}$ are identical or different and are each a hydrogen atom, a linear, cyclic or branched hydrocarbon group, for example an alkyl group of from 1 to about 10 carbon atoms, an alkenyl group of from 2 to about 10 carbon atoms, an aryl group of from 6 to about 20 carbon atoms, an arylalkyl group of from 7 to about 40 carbon atoms, an alkylaryl group of from 7 to about 40 carbon atoms or an arylalkenyl group of from 8 to about 40 carbon atoms, or a substituted or unsubstituted alkylsilyl or arylsilyl group, with the proviso that $R^3$ and $R^{3'}$ are not hydrogen. The groups may contain one or more hetero atoms like Si, B, Al, O, S, N or P, and/or may contain halogen atoms like F, Cl or Br, and/or two adjacent radicals $R^5$, $R^6$ or $R^{5'}$, $R^{6'}$, or $R^6$, $R^7$ or $R^{6'}$, $R^{7'}$, or $R^7$, $R^8$ or $R^{7'}$, $R^{8'}$ in each case may form a hydrocarbon ring system, and the bridging unit $R^9$ has the meaning set forth above with respect to formula 1a.

The 4,5,6,7-tetrahydroindenyl and the (a) heteroatom(s) containing indenyl analogues corresponding to the compounds 1b are likewise of importance.

In formula 1b it is preferred that $M^1$ is zirconium or hafnium, $R^1$ and $R^2$ are identical or different and are an alkyl group of from 1 to about 10 carbon atoms, an alkoxy group of from 1 to about 10 carbon atoms, an aryloxy group of from 6 to 10 carbon atoms or a halogen atom, or $R^1$ and $R^2$ together may form one or more ring system(s), $R^3$ and $R^{3'}$, are identical or different and are each a linear, cyclic or branched hydrocarbon group which may be halogenated, for example an alkyl group of from 1 to about 10 carbon atoms or an alkenyl group of from 2 to about 10 carbon atoms, $R^4$, $R^5$, $R^6$, $R^7$, $R^8$ and also $R^{4'}$, $R^{5'}$, $R^{6'}$, $R^{7'}$ and $R^{8'}$ are identical or different and are each a hydrogen atom, a substituted or unsubstituted alkylsilyl or arylsilyl group, a linear, cyclic or branched alkyl group of from 1 to about 10 carbon atoms, or an aryl group of from 6 to about 10 carbon atoms, which may contain one or more hetero atoms like Si, B, Al, O, S, N or P, and/or may contain halogen atoms like F, Cl or Br, and/or the two adjacent radicals $R^5$, $R^6$ and $R^{5'}$, $R^{6'}$ may form a hydrocarbon ring system, $R^9$ is $R^{40}R^{41}Si=$, $R^{40}R^{41}Ge=$, $R^{40}R^{41}C=$ or $-(R^{40}R^{41}C-CR^{40}R^{41})-$, where $R^{40}$ and $R^{41}$ are identical or different and are each a $C_2-C_{30}$ hydrocarbon group, in particular an alkyl group of from 2 to about 10 carbon atoms, an arylalkyl group of from 7 to about 14 carbon atoms or an alkylaryl group of from 7 to about 14 carbon atoms. If $R^{40}$ and $R^{41}$ are different and $R^{40}$ is a hydrocarbon group of from 4 to about 30 carbon atoms, $R^{41}$ can be a hydrocarbon group of from 1 to about 30 carbon atoms.

The 4,5,6,7-tetrahydroindenyl and the (a) heteroatom(s) containing indenyl analogues corresponding to the compounds 1b are likewise of importance.

In formula 1b it is very particularly preferred that $M^1$ is zirconium, $R^1$ and $R^2$ are identical or different and are methyl, chlorine or phenolate, $R^3$ and $R^{3'}$, are identical or different and are each a linear, cyclic or branched hydrocarbon group which may be halogenated, for example an alkyl group of from 1 to about 10 carbon atoms or an alkenyl group of from 2 to about 10 carbon atoms, $R^4$ and also $R^{4'}$ are hydrogen, $R^5$, $R^6$, $R^7$, $R^8$ and also $R^{5'}$, $R^{6'}$, $R^{7'}$, $R^{8'}$ are identical or different and are each a hydrogen atom or a linear, cyclic or branched alkyl group of from 1 to about 10 carbon atoms, or an aryl group of from 6 to about 10 carbon atoms and/or the two adjacent radicals $R^5$, $R^6$ and $R^{5'}$, $R^{6'}$ respectively together may form a ring system, $R^9$ is $R^{40}R^{41}Si=$ or $R^{40}R^{41}Ge=$, where $R^{40}$ and $R^{41}$ are identical or different and are propyl, butyl, pentyl, hexyl, heptyl, octyl, nonyl, decyl, undecyl, dodecyl, cyclo-pentyl, cyclo-pentadienyl or cyclohexyl. If $R^{40}$ and $R^{41}$ are different and $R^{40}$ is butyl, pentyl, hexyl, heptyl, octyl, nonyl, decyl, undecyl, dodecyl, cyclopentyl, cyclopentadienyl or cyclohexyl, $R^{41}$ can be methyl, ethyl, propyl, butyl, pentyl, hexyl, heptyl, octyl, nonyl, decyl, undecyl, dodecyl, cyclopentyl, cyclopentadienyl or cyclohexyl.

Most preferred for the production of polypropylenes with high melting points for applications, where a high stiffness is required, as the substituted and specifically bridged metallocene component of the catalyst system of the present invention, use is made of at least one compound of the formula 1c below

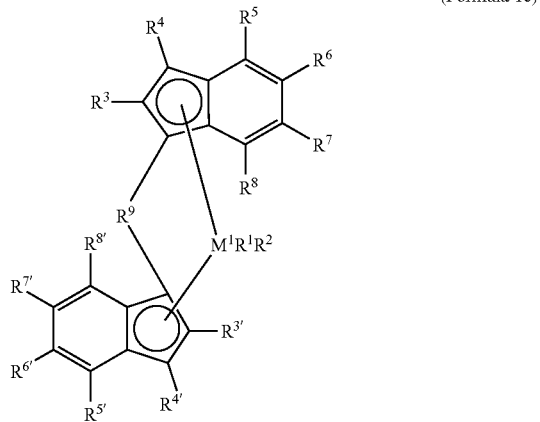

(Formula 1c)

where the substituents and indices have the following meanings:

$M^1$ is a metal of group IVb of the Periodic Table of the Elements, $R^1$ and $R^2$ are identical or different and are each a hydrogen atom, an alkyl group of from 1 to about 10 carbon atoms, an alkoxy group of from 1 to about 10 carbon atoms, an aryl group of from 6 to about 10 carbon atoms, an aryloxy group of from 6 to about 10 carbon atoms, an alkenyl group of from 2 to about 10 carbon atoms, an OH group, a halogen atom, or a $NR_2^{32}$ group, where $R^{32}$ is an alkyl group of from 1 to about 10 carbon atoms or an aryl group of from 6 to about 10 carbon atoms, and $R^1$ and $R^2$ may form one or more ring system(s), $R^3$, $R^4$, $R^5$, $R^6$, $R^7$, $R^8$ and also $R^{3'}$, $R^{4'}$, $R^{5'}$, $R^{6'}$, $R^{7'}$ and $R^{8'}$ are identical or different and are each a hydrogen atom, a linear, cyclic or branched hydrocarbon group, for example an alkyl group of from 1 to about 10 carbon atoms, an alkenyl group of from 2 to about 10 carbon atoms, an aryl group of from 6 to about 20 carbon atoms, an arylalkyl group of from 7 to about 40 carbon atoms, an alkylaryl group of from 7 to about 40 carbon atoms or an arylalkenyl group of from 8 to about 40 carbon atoms, a substituted or unsubstituted alkylsilyl or arylsilyl group, with the proviso that $R^3$ and $R^{3'}$ are not hydrogen and that $R^5$ and $R^{5'}$ are identical or different and are each a substituted or unsubstituted aryl group of from 6 to about 40 carbon atoms. The groups may contain one or more hetero atoms like Si, B, Al, O, S, N or P, and/or may contain halogen atoms like F, Cl or Br, and the bridging unit $R^9$ has the meaning set forth above with respect to formula 1a.

The 4,5,6,7-tetrahydroindenyl and the (a) heteroatom(s) containing indenyl analogues corresponding to the compounds 1c are likewise of importance.

In formula 1c it is preferred that $M^1$ is zirconium or hafnium, $R^1$ and $R^2$ are identical or different and are an alkyl group of from 1 to about 10 carbon atoms, an alkoxy group of from 1 to about 10 carbon atoms, an aryloxy group of from 6 to about 10 carbon atoms, or a halogen atom, and $R^1$ and $R^2$ may form one or more ring system(s), $R^3$ and $R^{3'}$, are identical or different and are each a linear, cyclic or branched group which may be halogenated, for example an alkyl group of from 1 to about 10 carbon atoms or an alkenyl group of from 2 to about 10 carbon atoms, $R^4$, $R^6$, $R^7$, $R^8$ and also $R^{4'}$, $R^{6'}$, $R^{7'}$ and $R^{8'}$ are identical or different and are each a hydrogen atom or a linear, cyclic or branched alkyl group of from 1 to about 10 carbon atoms, which may contain one or more hetero atoms like Si, B, Al, O, S, N or P, and/or may contain halogen atoms like F, Cl or Br, $R^5$ and $R^{5'}$ are identical or different and are each a substituted aryl group of from 6 to about 40 carbon atoms, $R^9$ is $R^{40}R^{41}Si=$, $R^{40}R^{41}Ge=$, $R^{40}R^{41}C=$ or $—(R^{40}R^{41}C—CR^{40}R^{41})—$, where $R^{40}$ and $R^{41}$ are identical or different and are each a $C_2$-$C_{30}$ hydrocarbon group, in particular an alkyl group of from 2 to about 10 carbon atoms, an arylalkyl group of from 7 to about 14 carbon atoms or an alkylaryl group of from 7 to about 14 carbon atoms. If $R^{40}$ and $R^{41}$ are different and $R^{40}$ is a hydrocarbon group of from 4 to about 30 carbon atoms, $R^{41}$ can be a hydrocarbon group of from 1 to about 30 carbon atoms.

The 4,5,6,7-tetrahydroindenyl and the (a) heteroatom(s) containing indenyl analogues corresponding to the compounds 1c are likewise of importance.

In formula 1c it is very particularly preferred that $M^1$ is zirconium, $R^1$ and $R^2$ are identical and are methyl, chlorine, or phenolate, $R^3$ and $R^{3'}$ are identical or different and are each a linear, cyclic or branched methyl, ethyl, propyl, butyl, pentyl or hexyl, $R^4$ and also $R^{4'}$ are hydrogen, $R^6$; $R^7$, $R^8$ and also $R^{6'}$, $R^{7'}$ and $R^{8'}$ are identical or different and are each a hydrogen atom or a linear, cyclic or branched alkyl group of from 1 to about 10 carbon atoms, which may contain one or more hetero atoms like Si, B, Al, O, S, N or P, and/or may contain halogen atoms like F, Cl or Br, $R^5$ and $R^{5'}$ are identical or different and are naphthyl, para-($C_1$-$C_{10}$-alkyl)phenyl, para-($C_1$-$C_{10}$-fluoroalkyl)phenyl, meta-($C_1$-$C_{10}$-alkyl)phenyl, meta-($C_1$-$C_{10}$-alkyl)phenyl, meta, meta'-($C_1$-$C_{10}$-alkyl)$_2$phenyl or meta, meta'-($C_1$-$C_{10}$-fluoroalkyl)$_2$phenyl, $R^9$ is $R^{40}R^{41}Si=$ or $R^{40}R^{41}Ge=$, where $R^{40}$ and $R^{41}$ are identical or different and are propyl, butyl, pentyl, hexyl, heptyl, octyl, nonyl, decyl, undecyl, dodecyl, cyclo-pentyl, cyclo-pentadienyl or cyclohexyl. If $R^{40}$ and $R^{41}$ are different and $R^{40}$ is butyl, pentyl, hexyl, heptyl, octyl, nonyl, decyl, undecyl, dodecyl, cyclopentyl, cyclopentadienyl or cyclohexyl, $R^{41}$ can be methyl, ethyl, propyl, butyl, pentyl, hexyl, heptyl, octyl, nonyl, decyl, undecyl, dodecyl, cyclopentyl, cyclopentadienyl or cyclohexyl.

Most preferred for the production of high molecular weight random copolymers or copolymer rubber, for the production of impact copolymers comprising high molecular weight copolymers or for the production of polypropylenes with melting points higher than 155° C. for applications, where a high stiffness is required, as the substituted and specifically bridged metallocene component of the catalyst system of the present invention use is made of at least one compound of the formula 1d below,

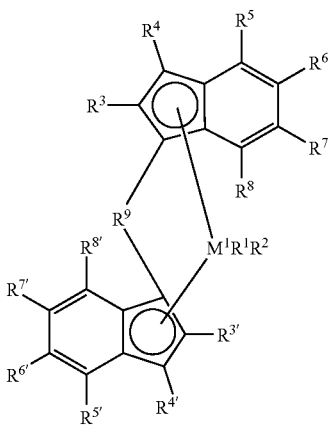

(Formula 1d)

where the substituents and indices have the following meanings:

$M^1$ is a metal of group IVb of the Periodic Table of the Elements, $R^1$ and $R^2$ are identical or different and are each a hydrogen atom, an alkyl group of from 1 to about 10 carbon atoms, an alkoxy group of from 1 to about 10 carbon atoms, an aryl group of from 6 to about 10 carbon atoms, an aryloxy group of from 6 to about 10 carbon atoms, an alkenyl group of from 2 to about 10 carbon atoms, an OH group, a halogen atom, or a $NR_2^{32}$ group, where $R^{32}$ is an alkyl group of from 1 to about 10 carbon atoms, or an aryl group of from 6 to about 14 carbon atoms, or $R^1$ and $R^2$ together may form one or more ring system(s), $R^4$, $R^5$, $R^6$, $R^7$, $R^8$ and also $R^{4'}$, $R^{5'}$, $R^{6'}$, $R^{7'}$ and $R^{8'}$ identical or different and are each a hydrogen atom, a linear, cyclic or branched hydrocarbon group, for example an alkyl group of from 1 to about 10 carbon atoms, an alkenyl group of from 2 to about 10 carbon atoms, an aryl group of from 6 to about 20 carbon atoms, an arylalkyl group of from 7 to about 40 carbon atoms, an alkylaryl group of from 7 to about 40 carbon atoms, or a arylalkenyl group of from 8 to about 40 carbon atoms, a substituted or unsubstituted alkylsilyl or arylsilyl group, with the proviso that $R^5$ and $R^{5'}$ are identical or different and are each a substituted aryl group of from 6 to about 40 carbon atoms. The hydrocarbon groups may contain one or more hetero atoms like Si, B, Al, O, S, N or P, and/or may contain halogen atoms like F, Cl or Br, $R^3$ is a hydrocarbon group, not cyclic or branched in the α-position, for example an alkyl group of from 1 to about 20 carbon atoms, an aryl substituted alkyl group of from 7 to about 40 carbon atoms, or an aryl substituted alkenyl group of from 8 to about 40 carbon atoms. The hydrocarbon groups may contain one or more hetero atoms like Si, B, Al, O, S, N or P, and/or may contain halogen atoms like F, Cl or Br, $R^{3'}$ is in an α-position cyclic or branched group, for example an alkyl group of from 3 to about 20 carbon atoms, an alkenyl group of from 3 to about 20 carbon atoms, an aryl group of from 6 to about 20 carbon atoms, an arylalkyl group of from 7 to about 40 carbon atoms, an alkylaryl group of from 7 to about 40 carbon atoms, or an arylalkenyl group of from 8 to about 40 carbon atoms. The groups may contain one or more hetero atoms like Si, B, Al, O, S, N or P, and/or may contain halogen atoms like F, Cl or Br, and the bridging unit $R^9$ has the meaning mentioned above with respect to formula 1a.

The 4,5,6,7-tetrahydroindenyl and the (a) heteroatom(s) containing indenyl analogues corresponding to the compounds 1d are likewise of importance.

In formula 1d it is preferred that $M^1$ is zirconium or hafnium, $R^1$ and $R^2$ are identical or different and are an alkyl group of from 1 to about 10 carbon atoms, an alkoxy group of from 1 to about 10 carbon atoms, an aryloxy group of from 6 to about 10 carbon atoms, or a halogen atom, and $R^1$ and $R^2$ may form one or more ring system(s), $R^3$ is a linear alkyl group of from 1 to about 10 carbon atoms or an alkenyl group of from 2 to about 10 carbon atoms, which can be halogenated, $R^{3'}$ is a in α-position cyclic or branched alkyl group of from 3 to about 20 carbon atoms, an alkenyl group of from 3 to about 20 carbon atoms, or an alkylaryl group of from 7 to about 20 carbon atoms, $R^4$, $R^6$, $R^7$, $R^8$ and also $R^{4'}$, $R^{6'}$, $R^{7'}$ and $R^{8'}$ are identical or different and are each a hydrogen atom or a linear, cyclic or branched alkyl group of from 1 to about 10 carbon atoms, which may contain one or more hetero atoms like Si, B, Al, O, S, N or P, and/or may contain halogen atoms like F, Cl or Br, $R^5$ and $R^5$ are identical or different and are each a substituted aryl group of from 6 to about 40 carbon atoms, like para-$(C_1$-$C_{10}$-alkyl)phenyl, meta-$(C_1$-$C_{10}$-alkyl)phenyl, meta, meta'-$(C_1$-$C_{10}$-alkyl)$_2$phenyl.

$R^9$ is $R^{40}R^{41}Si=$, $R^{40}R^{41}Ge=$, $R^{40}R^{41}C=$ or —$(R^{40}R^{41}C$—$CR^{40}R^{41})$—, where $R^{40}$ and $R^{41}$ are identical or different and are each a $C_2$-$C_{30}$ group, in particular an alkyl group of from 2 to about 10 carbon atoms, an arylalkyl group of from 7 to about 14 carbon atoms, or an alkylaryl group of from 7 to about 14 carbon atoms. If $R^{40}$ and $R^{41}$ are different and $R^{40}$ is a hydrocarbon group of from 4 to about 30 carbon atoms, $R^{41}$ can be a hydrocarbon group of from 1 to about 30 carbon atoms.

The 4,5,6,7-tetrahydroindenyl and the (a) heteroatom(s) containing indenyl analogues corresponding to the compounds 1d are likewise of importance.

In formula 1d, it is very particularly preferred that $M^1$ is zirconium, $R^1$ and $R^2$ are identical and are methyl, chlorine, or phenolate, $R^3$ is methyl, ethyl, n-propyl, n-butyl, n-pentyl or n-hexyl, $R^{3'}$ is iso-propyl, iso-butyl, n-butyl, sec-butyl, cyclobutyl, 1-methyl-butyl, 1-ethyl-butyl, 1-methyl-pentyl, cyclopentyl, cyclohexyl, cyclopent-2-enyl, cyclopent-3-enyl, cyclohex-2-enyl, cyclohex-3-enyl or para-methyl-cyclohexyl, $R^4$ and also $R^{4'}$ are hydrogen, and $R^6$, $R^7$, $R^8$ and also $R^{6'}$, $R^{7'}$ and $R^{8'}$ are identical or different and are each a hydrogen atom or a linear, cyclic or branched alkyl group of from 1 to about 10 carbon atoms, which may contain one or more hetero atoms like Si, B, Al, O, S, N or P, and/or may contain halogen atoms like F, Cl or Br, $R^5$ and $R^{5'}$ are identical or different and are p-isopropyl-phenyl, p-tert.-butyl-phenyl, p-s-butyl-phenyl, p-cyclohexyl-phenyl, p-trimethylsilyl-phenyl, p-adamantyl-phenyl, p-(trisfluor)trimethyl-phenyl, m,m'-dimethyl-phenyl, $R^9$ is $R^{40}R^{41}$ Si= or $R^{40}R^{41}Ge=$, where $R^{40}$ and $R^{41}$ are identical or different and are propyl, butyl, pentyl, hexyl, heptyl, octyl, nonyl, decyl, undecyl, dodecyl, cyclo-pentyl, cyclo-pentadienyl or cyclo-hexyl. If $R^{40}$ and $R^{41}$ are different and $R^{40}$ is butyl, pentyl, hexyl, heptyl, octyl, nonyl, decyl, undecyl, dodecyl, cyclopentyl, cyclopentadienyl or cyclohexyl, $R^{41}$ can be methyl, ethyl, propyl, butyl, pentyl, hexyl, heptyl, octyl, nonyl, decyl, undecyl, dodecyl, cyclopentyl, cyclopentadienyl or cyclohexyl.

Not limiting examples for the particularly preferred metallocene compounds of the present invention are the following compounds of formulas 1a -1d:

A-(2-isopropyl-4-(p-isopropyl-phenyl)indenyl)(2-methyl-4-(p-isopropyl-phenyl)indenyl)-zirconiumdichloride,
A-(2-isopropyl-4-(p-tert. butyl-phenyl)indenyl)(2-methyl-4-(p-tert. butyl-phenyl)indenyl)-zirconiumdichloride,
A-(2-isopropyl-4-(p-tert. butyl-phenyl)indenyl)(2,7-dimethyl-4-(p-tert. butyl-phenyl)indenyl)-zirconiumdichloride,
A-(2-isopropyl-4-(p-tert. butyl-phenyl)indenyl)(2,5,6,7-tetramethyl-4-(p-tert. butyl-phenyl)indenyl)-zirconiumdichloride,
A-(2-isopropyl-6-methyl-4-(p-tert. butyl-phenyl)indenyl)(2,6-dimethyl-4-(p-tert. butyl-phenyl)indenyl)-zirconiumdichloride,
A-(2-isopropyl-4-(p-sec. butyl-phenyl)indenyl)(2-methyl-4-(p-sec. butyl-phenyl)indenyl)-zirconiumdichloride,
A-(2-isopropyl-4-(p-cyclohexyl-phenyl)indenyl)(2-methyl-4-(p-cyclohexyl-phenyl)indenyl)-zirconiumdichloride,
A-(2-isopropyl-4-(p-trimethylsilyl-phenyl)indenyl)(2-methyl-4-(p-trimethylsilyl-phenyl)indenyl)-zirconiumdichloride,
A-(2-isopropyl-4-(p-adamantyl-phenyl)indenyl)(2-methyl-4-(p-adamantyl-phenyl)indenyl)-zirconiumdichloride,
A-(2-isopropyl-4-(p-tris(trifluoro-methyl)methyl-phenyl)indenyl)(2-methyl-4-(p-tris(trifluoro-methyl)methyl-phenyl)indenyl)-zirconiumdichloride,
A-(2-isopropyl-4-phenyl-indenyl)(2-methyl-4-(p-tert. butyl-phenyl)indenyl)-zirconiumdichloride;
A-(2-isopropyl-4-(p-tert. butyl-phenyl)indenyl)(2-methyl-4-phenyl-indenyl)-zirconiumdichloride,
A-(2-isopropyl-4-(p-tert. butyl-phenyl)indenyl)(2,7-dimethyl-4-phenyl-indenyl)-zirconiumdichloride,
A-(2-isopropyl-4-(p-tert. butyl-phenyl)indenyl)(2,5,6,7-tetramethyl-4-phenyl-indenyl)-zirconiumdichloride,
A-(2-isopropyl-6-methyl-4-(p-tert. butyl-phenyl)indenyl)(2,6-dimethyl-4-phenyl-indenyl)-zirconiumdichloride,
A-(2-isopropyl-4-phenyl-indenyl)(2,7-dimethyl-4-(p-tert. butyl-phenyl)indenyl)-zirconiumdichloride,
A-(2-isopropyl-4-phenyl-indenyl)(2,5,6,7-tetramethyl-4-(p-tert. butyl-phenyl)indenyl)-zirconiumdichloride,
A-(2-isopropyl-6-methyl-4-phenyl-indenyl)(2,6-dimethyl-4-(p-tert. butyl-phenyl)indenyl)-zirconiumdichloride,
A-(2-isopropyl-4-(p-tert. butyl-phenyl)indenyl)(2-methyl-4-(4-naphthyl)-indenyl)indenyl)-zirconiumdichloride,
A-(2-isopropyl-4-(4-naphthyl)-indenyl)indenyl)(2-methyl-4-(p-tert. butyl-phenyl)indenyl)-zirconiumdichloride,
A-bis(4-naphthyl-indenyl)zirconiumdichloride,
A-bis(2-methyl-benzo-indenyl)zirconiumdichloride
A-bis(2-methyl-indenyl)zirconiumdichloride,
A-bis(2-methyl-4-(1-naphthyl)-indenyl)zirconiumdichloride,
A-bis(2-methyl-4-(2-naphthyl)-indenyl)zirconiumdchloride,
A-bis(2-methyl-4-phenyl-indenyl)zirconiumdichloride,
A-bis(2-methyl-4-t-butyl-indenyl)zirconiumdichloride,
A-bis(2-methyl-4-isopropyl-indenyl)zirconiumdichloride,
A-bis(2-methyl-4-ethyl-indenyl)zirconiumdichloride,
A-bis(2-methyl-4-acenaphth-indenyl)zirconiumdichloride,
A-bis(2,4-dimethyl-indenyl)zirconiumdichloride,
A-bis(2-ethyl-indenyl)zirconiumdichloride,
A-bis(2-ethyl-4-ethyl-indenyl)zirconiumdichloride,
A-bis(2-ethyl-4-phenyl-indenyl)zirconiumdichloride,
A-bis(2-methyl-4,6 diisopropyl-indenyl)zirconiumdichloride,
A-bis(2-methyl-4,5 diisopropyl-indenyl)zirconiumdichloride,
A-bis(2,4,6-trimethyl-indenyl)zirconiumdichloride,
A-bis(2,5,6-trimethyl-indenyl)zirconiumdichloride,
A-bis(2,4,7-trimethyl-indenyl)zirconiumdichloride,
A-bis(2-methyl-5-isobutyl-indenyl)zirconiumdichloride,
A-bis(2-methyl-5-t-butyl-indenyl)zirconiumdichloride,
A-bis(2-methyl-4-(tert-butyl-phenyl)-indenyl)zirconiumdichloride,
A-bis(2-methyl-4-(4-methyl-phenyl)-indenyl)zirconiumdichloride,
A-bis(2-methyl-4-(4-ethyl-phenyl)-indenyl)zirconiumdichloride,
A-bis(2-methyl-4-(4-trifluoromethyl-phenyl)-indenyl)zirconiumdichloride,
A-bis(2-methyl-4-(4-methoxy-phenyl)-indenyl)zirconiumdichloride,
A-bis(2-ethyl-4-(4-tert-butyl-phenyl)-indenyl)zirconiumdichloride,
A-bis(2-ethyl-4-(4-methyl-phenyl)-indenyl)zirconiumdichloride,
A-bis(2-ethyl-4-(4-ethyl-phenyl)-indenyl)zirconiumdichloride,
A-bis(2-ethyl-4-(4-trifluoromethyl-phenyl)-indenyl)zirconiumdichloride,
A-bis(2-ethyl-4-(4-methoxy-phenyl)-indenyl)zirconiumdichloride,
A-bis(2-methyl-4-(4-tert-butyl-phenyl)-indenyl)zirconiumdimethyl,
A-bis(2-methyl-4-(4-methyl-phenyl)-indenyl)zirconiumdimethyl,
A-bis(2-methyl-4-(4-ethyl-phenyl)-indenyl)zirconiumdimethyl,
A-bis(2-methyl-4-(4-trifluoromethyl-phenyl)-indenyl)zirconiumdimethyl,
A-bis(2-methyl-4-(4-methoxy-phenyl)-indenyl)zirconiumdimethyl,
A-bis(2-ethyl-4-(4-tert-butyl-phenyl)-indenyl)zirconiumdimethyl,
A-bis(2-ethyl-4-(4-methyl-phenyl)-indenyl)zirconiumdimethyl,
A-bis(2-ethyl-4-(4-ethyl-phenyl)-indenyl)zirconiumdimethyl,
A-bis(2-ethyl-4-(4-trifluoromethyl-phenyl)-indenyl)zirconiumdimethyl,
A-bis(2-ethyl-4-(4-methoxy-phenyl)-indenyl)zirconiumdimethyl,
A-bis(2-isopropyl-4-(tert-butyl-phenyl)-indenyl)zirconiumdichloride,
A-bis(2-isopropyl-4-(4-methyl-phenyl)-indenyl)zirconiumdichloride,
A-bis(2-isopropyl-4-(4-ethyl-phenyl)-indenyl)zirconiumdichloride,
A-bis(2-isopropyl-4-(4-trifluoromethyl-phenyl)-indenyl)zirconiumdichloride,
A-bis(2-isopropyl-4-(4-methoxy-phenyl)-indenyl)zirconiumdichloride,
A-bis(2-isopropyl-4-(4'-tert.-butyl-phenyl)-indenyl)zirconiumdichloride,
A-bis(2-isopropyl-4-(4'-tert.-butyl-phenyl)-indenyl)hafniumdichloride,
A-bis(2 isopropyl-4-(4'-tert.-butyl-phenyl)-indenyl)titaniumdichloride,
A-bis(2-isopropyl-4-(4'-methyl-phenyl)-indenyl)zirconiumdichloride, A-bis(2-isopropyl-4-(4'-n-propyl-phenyl)-indenyl)zirconiumdichloride,
A-bis(2-isopropyl-4-(4'-n-butyl-phenyl)-indenyl)zirconiumdichloride,
A-bis(2-isopropyl-4-(4'-hexyl-phenyl)-indenyl)zirconiumdichloride,
A-bis(2-isopropyl 1-4-(4'-sec-butyl-phenyl)-indenyl)zirconiumdichloride,
A-bis(2-isopropyl-4-phenyl)-indenyl)zirconiumdichloride,
A-bis(2-isopropyl-4-(4'-methyl-phenyl)-indenyl)zirconiumdichloride,
A-bis(2-isopropyl-4-(4'-ethyl-phenyl)-indenyl)zirconiumdichloride,
A-bis(2-isopropyl-4-(4'-n-propyl-phenyl)-indenyl)zirconiumdichloride,
A-bis(2-isopropyl-4-(4'-n-butyl-phenyl)-indenyl)zirconiumdichloride,
A-bis(2-isopropyl-4-(4'-hexyl-phenyl)-indenyl)zirconiumdichloride,
A-bis(2-isopropyl 4-(4'-pentyl-phenyl)-indenyl)zirconiumdichloride,
A-bis(2-isopropyl-4-(4'-cyclohexyl-phenyl)-indenyl)zirconiumdichloride,
A-bis(2-isopropyl-4-(4'-sec-butyl-phenyl)-indenyl)zirconiumdichloride,
A-bis(2-isopropyl-4-(4'-tert.-butyl-phenyl)-indenyl)zirconiumdichloride,
A-bis(2-isopropyl-4-(4'-tert.-butyl-phenyl)-indenyl)zirconiumdichloride,
A-bis(2-methyl-4-(4'-tert.-butyl-phenyl)-indenyl)hafniumdichloride,
A-bis(2-methyl-4-(4'-tert.-butyl-phenyl)-indenyl)hafniumdichloride,
A-bis(2-methyl-4-(4'-methyl-phenyl)-indenyl)zirconiumdichloride,
A-bis(2-methyl-4-(4'-n-propyl-phenyl)-indenyl)zirconiumdichloride,
A-bis(2-methyl-4-(4'-n-butyl-phenyl)-indenyl)zirconiumdichloride,
A-bis(2-methyl-4-(4'-hexyl-phenyl)-indenyl)zirconiumdichloride,
A-bis(2-methyl-4-(4'-sec-butyl-phenyl)-indenyl)zirconiumdichloride,
A-bis(2-ethyl-4-phenyl-indenyl)zirconiumdichloride,
A-bis(2-ethyl-4-(4'-methyl-phenyl)-indenyl)zirconiumdichloride,
A-bis(2-ethyl-4-(4'-ethyl-phenyl)-indenyl)zirconiumdichloride,
A-bis(2-ethyl-4-(4'-n-propyl-phenyl)-indenyl)zirconiumdichloride,
A-bis(2-ethyl-4-(4'-n-butyl-phenyl)-indenyl)zirconiumdichloride,
A-bis(2-ethyl-4-(4'-hexyl-phenyl)-indenyl)zirconiumdichloride,
A-bis(2-ethyl-4-(4'-pentyl-phenyl)-indenyl)zirconiumdichloride,
A-bis(2-ethyl-4-(4'-cyclohexyl-phenyl)-indenyl)zirconiumdichloride,
A-bis(2-ethyl-4-(4'-sec-butyl-phenyl)-indenyl)zirconiumdichloride,
A-bis(2-ethyl-4-(4'-tert.-butyl-phenyl)-indenyl)zirconiumdichloride,
A-bis(2-n-propyl-4-phenyl-indenyl)zirconiumdichloride,
A-bis(2-n-propyl-4-(4'-methyl-phenyl)-indenyl)zirconiumdichloride,
A-bis(2-n-propyl-4-(4'-ethyl-phenyl)-indenyl)zirconiumdichloride,
A-bis(2-n-propyl-4-(4'-iso-propyl-phenyl)-indenyl)zirconiumdichloride,
A-bis(2-n-propyl-4-(4'-n-butyl-phenyl)-indenyl)zirconiumdichloride,
A-bis(2-n-propyl-4-(4'-hexyl-phenyl)-indenyl)zirconiumdichloride,
A-bis(2-n-propyl-4-(4'-cyclohexyl-phenyl)-indenyl)zirconiumdichloride,
A-bis(2-n-propyl-4-(4'-sec-butyl-phenyl)-indenyl)zirconiumdichloride,
A-bis(2-n-propyl-4-(4'-tert.-butyl-phenyl)-indenyl)zirconiumdichloride,
A-bis(2-n-butyl-4-phenyl-indenyl)zirconiumdichloride,
A-bis(2-n-butyl-4-(4'-methyl-phenyl)-indenyl)zirconiumdichloride,
A-bis(2-n-butyl-4-(4'-ethyl-phenyl)-indenyl)zirconiumdichloride,
A-bis(2-n-butyl-4-(4'-n-propyl-phenyl)-indenyl)zirconiumdichloride,
A-bis(2-n-butyl-4-(4'-iso-propyl-phenyl)-indenyl)zirconiumdichloride,
A-bis(2-n-butyl-4-(4'-n-butyl-phenyl)-indenyl)zirconiumdichloride,
A-bis(2-n-butyl-4-(4'-hexyl-phenyl)-indenyl)zirconiumdichloride,
A-bis(2-n-butyl-4-(4'-cyclohexyl-phenyl)-indenyl)zirconiumdichloride,
A-bis(2-n-butyl-4-(4'-sec-butyl-phenyl)-indenyl)zirconiumdichloride,
A-bis(2-n-butyl-4-(4'-tert.-butyl-phenyl)-indenyl)zirconiumdichloride,
A-bis(2-hexyl-4-phenyl-indenyl)zirconiumdichloride,
A-bis(2-hexyl-4-(4'-methyl-phenyl)-indenyl)zirconiumdichloride,
A-bis(2-hexyl-4-(4'-ethyl-phenyl)-indenyl)zirconiumdichloride,
A-bis(2-hexyl-4-(4'-n-propyl-phenyl)-indenyl)zirconiumdichloride,
A-bis(2-hexyl-4-(4'-iso-propyl-phenyl)-indenyl)zirconiumdichloride,
A-bis(2-hexyl-4-(4'-n-butyl-phenyl)-indenyl)zirconiumdichloride,
A-bis(2-hexyl-4-(4'-n-hexyl-phenyl)-indenyl)zirconiumdichloride,
A-bis(2-hexyl-4-(4'-cyclohexyl-phenyl)-indenyl)zirconiumdichloride,
A-bis(2-hexyl-4-(4'-sec-butyl-phenyl)-indenyl)zirconiumdichloride,
A-bis(2-hexyl-4-(4'-tert.-butyl-phenyl)-indenyl)zirconiumdichloride,
A-bis(2-methyl-4-(4'-tert.-butyl-phenyl)-indenyl)zirconiumbis (dimethylamine),
A-bis(2-ethyl-4-(4'-tert.-butyl-phenyl)-indenyl)zirconiumdibenzyl,
A-bis(2-methyl-4-(4'-tert.-butyl-phenyl)-indenyl)zirconiumdimethyl,
A-(2-methyl-4-azapentalene)(2-methyl-4-(4'-methyl-phenyl)-indenyl) zirconiumdichloride,
A-(2-methyl-5-azapentalene)(2-methyl-4-(4'-methyl-phenyl)-indenyl) zirconiumdichloride,
A-(2-methyl-6-azapentalene)(2-methyl-4-(4'-methyl-phenyl)-indenyl) zirconiumdichloride,
A-(2-methyl-4-azapentalene)(2-methyl-4-(4'-ethyl-phenyl)-indenyl) zirconiumdichloride,
A-(2-methyl-4-thiapentalene)(2-methyl-4-(4'-n-propyl-phenyl)-indenyl)-zirconiumdichloride, A-(2-methyl-4-azapentalene)(2-methyl-4-(4'-isopropyl-phenyl)-indenyl)-zirconiumdichloride,
A-(2-methyl-6-azapentalene)(2-methyl-4-(4'-isopropyl-phenyl)-indenyl)-zirconiumdichloride,
A-(2,5-dimethyl-6-thiapentalene)(2-methyl-4-(4'-isopropyl-phenyl)-indenyl)-zirconiumdichloride,
A-(2-methyl-6-oxapentalen)(2-methyl-4-(4'-isopropyl-phenyl)-indenyl)zirconiumdichloride,
A-(2-methyl-6-azapentalene)(2-methyl-4-(4'-n-butyl-phenyl)-indenyl)-zirconiumdichloride,
A-(2-methyl-5-thiapentalene)(2-methyl-4-(4'-n-butyl-phenyl)-indenyl) zirconiumdichloride,
A-(2-methyl-4-oxapentalene)(2-methyl-4-(4'-n-butyl-phenyl)-indenyl)zirconiumdichloride,
A-(2-methyl-4-thiapentalene)(2-methyl-4-(4'-s-butyl-phenyl)-indenyl)zirconiumdichloride,
A-(2-methyl-4-oxapentalene)(2-methyl-4-(4'-s-butyl-phenyl)-indenyl)zirconiumdichloride,
A-(2-methyl-4-azapentalene)(2-methyl-4-(4'-tert-butyl-phenyl)-indenyl)-zirconiumdichloride,
A-(2-methyl-6-azapentalene)(2-methyl-4-(4'-tert-butyl-phenyl)-indenyl)-zirconiumdichloride,
A-(2-methyl-4-azapentalene)(2-methyl-4-(4'-n-pentyl-phenyl)-indenyl)-zirconiumdichloride,
A-(2-methyl-N-phenyl-6-azapentalene)(2-methyl-4-(4'-n-pentyl-phenyl)-indenyl)-zirconiumdichloride,
A-(2-methyl-4-oxapentalene)(2-methyl-4-(4'-n-pentyl-phenyl)-indenyl)-zirconiumdichloride,
A-(2-methyl-4-azapentalene)(2-methyl-4-(4'-n-hexyl-phenyl)-indenyl)-zirconiumdichloride,
A-(2-methyl-4-thiapentalene)(2-methyl-4-(4'-n-hexyl-phenyl)-indenyl)-zirconiumdichloride,
A-(2-methyl-6-thiapentalene)(2-methyl-4-(4'-n-hexyl-phenyl)-indenyl)-zirconiumdichloride,
A-(2,5-dimethyl-4-thiapentalene)(2-methyl-4-(4'-n-hexyl-phenyl)-indenyl)-zirconiumdichloride,
A-(2,5-dimethyl-6-thiapentaiene)(2-methyl-4-(4'-n-hexyl-phenyl)-indenyl)-zirconiumdichloride,
A-(2,5-dimethyl-6-thiapentalene)(2-methyl-4-(4'-cyclohexyl-phenyl)-indenyl)-zirconiumdichloride,
A-(2-methyl-4-azapentalene)(2-methyl-4-(4'-trimethylsilyl-phenyl)-indenyl)-zirconiumdichloride,
A-(2-methyl-4-thiapentalene)(2-methyl-4-(4'-trimethylsilyl-phenyl)-indenyl)-zirconiumdichloride,
A-(2-methyl-5-thiapentalene)(2-methyl-4-(4'-trimethylsilyl-phenyl)-indenyl)-zirconiumdichloride,
A-(2-methyl-6-thiapentalene)(2-methyl-4-(4'-trimethylsilyl-phenyl)-indenyl)-zirconiumdichloride,
A-(2,5-dimethyl-4-azapentalene)(2-methyl-4-(4'-adamantyl-phenyl)-indenyl)-zirconiumdichloride,
A-(2-methyl-4-thiapentalene)(2-methyl-4-(4'-adamantyl-phenyl)-indenyl)-zirconiumdichloride,
A-(2-methyl-6-thiapentalene)(2-methyl-4-(4'-adamantyl-phenyl)-indenyl)-zirconiumdichloride,
A-(2,5-dimethyl-4-thiapentalene)(2-methyl-4-(4'-adamantyl-phenyl)-indenyl)-zirconiumdichloride,
A-(2-methyl-4-azapentalene)(2-methyl-4-(4'-tris(trifluoromethyl)methyl-phenyl)-indenyl)-zirconiumdichloride,
A-(2,5-dimethyl-4-azapentalene)(2-methyl-4-(4'-tris(trifluoromethyl)methyl-phenyl)-indenyl) zirconiumdichloride,
A-(2-methyl-4-thiapentalene)(2-methyl-4-(4'-tris(trifluoromethyl)methyl-phenyl)-indenyl)zirconiumdichloride,
A-(2-methyl-6-thiapentalene)(2-methyl-4-(4'-tris(trifluoromethyl)methyl-phenyl)-indenyl)zirconiumdichloride,
A-(2-methyl-4-azapentalene)(2-ethyl-4-(4'-tert-butyl-phenyl)-indenyl)-zirconiumdichloride,
A-(2-methyl-5-azapentalene)(2-n-butyl-4-(4'-tert-butyl-phenyl)-indenyl)-zirconiumdichloride,
A-(2-methyl-N-phenyl-6-azapentalene)(2-methyl-4-(4'-tert-butyl-phenyl)-indenyl)-zirconiumdichloride,
A-(2-methyl-4-azapentalene)(2-methylindenyl)zirconiumdichloride,
A-(2-methyl-N-phenyl-4-azapentalene)(2-methylindenyl)zirconiumdichloride,
A-(2-methyl-4-thiapentalene)(2-methylindenyl)zirconiumdichloride,
A-(2-methyl-5-thiapentalene)(2-methylindenyl)zirconiumdichloride,
A-(2-methyl-6-thiapentalene)(2-methylindenyl)zirconiumdichloride,
A-(2-methyl-4-azapentalene)(indenyl)zirconiumdichloride,
A-(2-methyl-5-azapentalene)(indenyl)zirconiumdichloride,
A-(2-methyl-6-azapentalene)(indenyl)zirconiumdichloride,
A-(2-methyl-N-phenyl-4-azapentalene)(indenyl)zirconiumdichloride,
A-(2-methyl-N-phenyl-5-azapentalene)(indenyl)zirconiumdichloride,
A-(2-methyl-N-phenyl-6-azapentalene)(indenyl)zirconiumdichloride,
A-(2,5-dimethyl-N-phenyl-6-azapentalene)(indenyl)zirconiumdichloride,
A-(2-methyl-4-thiapentalene)(indenyl)zirconiumdichloride,
A-(2-methyl-5-thiapentalene)(indenyl)zirconiumdichloride,
A-(2-methyl-6-thiapentalene)(indenyl)zirconiumdichloride,
A-(2,5-dimethyl-4-thiapentalene)(indenyl)zirconiumdichloride,
A-(2-methyl-4-azapentalene)(2-methyl-4-phenyl-indenyl)zirconiumdichloride,
A-(2-methyl-5-azapentalene)(2-methyl-4-phenyl-indenyl)zirconiumdichloride,
A-(2-methyl-6-azapentalene)(2-methyl-4-phenyl-indenyl)zirconiumdichloride,
A-(2-methyl-N-phenyl-4-azapentalene)(2-methyl-4-phenyl-indenyl) zirconiumdichloride,
A-(2-methyl-N-phenyl-5-azapentalene)(2-methyl-4-phenyl-indenyl) zirconiumdichloride,
A-(2-methyl-4-thiapentalene)(2-methyl-4-phenyl-indenyl)zirconiumdichloride,
A-(2-methyl-5-thiapentalene)(2-methyl-4-phenyl-indenyl)zirconiumdichloride,
A-(2-methyl-6-thiapentalene)(2-methyl-4-phenyl-indenyl)zirconiumdichloride,
A-(2-methyl-4-oxapentalene)(2-methyl-4-phenyl-indenyl)zirconiumdichloride,
A-(2-methyl-4-azapentalene)(2-methyl-4,5-benzo-indenyl)zirconiumdichloride,
A-(2-methyl-N-phenyl-4-azapentalene)(2-methyl-4,5-benzo-indenyl) zirconiumdichloride,
A-(2-methyl-N-phenyl-5-azapentalene)(2-methyl-4,5-benzo-indenyl) zirconiumdichloride,
A-(2-methyl-N-phenyl-6-azapentalene)(2-methyl-4,5-benzo-indenyl) zirconiumdichloride,
A-(2-methyl-4-thiapentalene)(2-methyl-4,5-benzo-indenyl) zirconiumdichloride, A-(2-methyl-5-thiapentalene)(2-methyl-4,5-benzo-indenyl)zirconiumdichloride,
A-(2-methyl-6-thiapentalene)(2-methyl-4,5-benzo-indenyl)zirconiumdichloride,
A-(2-methyl-4-oxapentalene)(2-methyl-4,5-benzo-indenyl)zirconiumdichloride,
A-(2-methyl-5-oxapentalene)(2-methyl-4,5-benzo-indenyl)zirconiumdichloride,
A-(2-methyl-6-oxapentalene)(2-methyl-4,5-benzo-indenyl)zirconiumdichloride,
A-bis(2-methyl-4-azapentalene)zirconiumdichloride,
A-bis(2-methyl-N-phenyl-4-azapentalene)zirconiumdichloride,
A-bis(2-methyl-4-thiapentalene)zirconiumdichloride.

A is Dipropylsilanediyl, Dibutylsilanediyl, Dipentylsilanediyl, Dihexylsilanediyl, Diheptylsilanediyl, Dioctylsilanediyl, Dinonylsilanediyl, Didecylsilanediyl, Diundecylsilanediyl, Didodecylsilanediyl, Dipropylgermanediyl, Dibutylgermanediyl, Dipentylgermanediyl, Dihexylgermanediyl, Diheptylgermanediyl, Dioctylgermanediyl, Dinonylgermanediyl, Didecylgermanediyl, Diundecylgermanediyl or Didodecylgermanediyl, Hexyl(methyl)germanediyl, Butyl(methyl)silanediyl, Butyl(ethyl)silanediyl, Butyl(propyl)silanediyl, Pentyl(methyl)silanediyl, Pentyl(ethyl)silanediyl, Pentyl(propyl)silanediyl, Hexyl(methyl)silanediyl, Hexyl(ethyl)silanediyl or Hexyl(propyl)silanediyl, such that the list of bridge elements A is to be understood in such a way that the naming of the substituents on the bridge atom is meant also to include all structural isomers as though they were explicitly named. For example, dibutylsilanediyl simultaneously includes di(n-butyl)silanediyl, di(sec-butyl)silanediyl, di(tert-butyl)silanediyl, or mixtures of these structural isomers. Similarly, the naming of dipentylsilanediyl also includes, for example, di(cyclopentyl)silanediyl or the naming of hexyl(methyl)silanediyl also includes, for example, cyclohexyl(methyl)silanediyl.

The particularly preferred units A of the metallocene compounds of the formulas 1a-1d are Di-n-propylsilanediyl, Di-n-butylsilanediyl, Di-n-pentylsilanediyl, Di(cyclopentyl)silanediyl, Di-n-hexylsilanediyl, Cyclohexyl(methyl)silanediyl, (n-butyl)(methyl)silanediyl and (n-hexyl)(methyl)silanediyl.

Another object of the invention is a ligand system with the formula LS or its double-bond isomers,

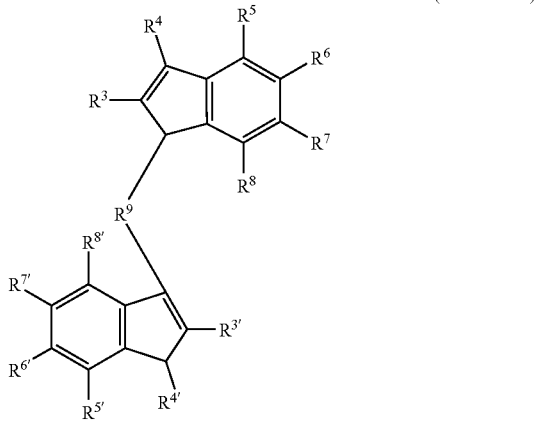

(Formula LS)

in which the variables R are defined as in formulas 1a-1d, including the preferred embodiments.

Instead of the preferred pure chiral bridged racemic or pseudoracemic metallocene compounds of formulas 1a-1d, mixtures of the metallocenes of formulas 1a-1d and the corresponding meso or pseudomeso metallocenes may be used in the catalyst preparation. However, the preparation of the isomerically pure racemic form is especially preferred for the use of metallocenes in the polymerization of olefins to isotactic polyolefins, since the corresponding meso form may produce undesired atactic polypropylene ("PP"). The "isomerically pure" racemic form is understood to mean a rac:meso ratio of greater than 5:1 preferably of at least 10:1, more preferred of at least 15:1 and most preferred of at least 20:1. As used herein the term "racemic" (or "rac") includes "pseudoracemic" (or "pseudorac"), and the term "meso" includes "pseudomeso."

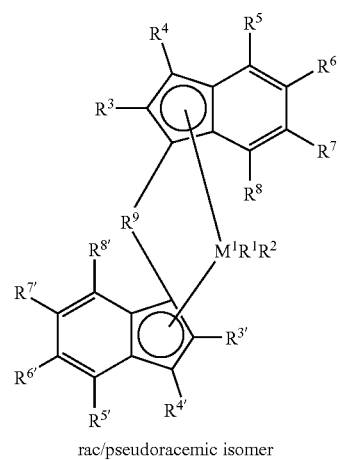

rac/pseudoracemic isomer

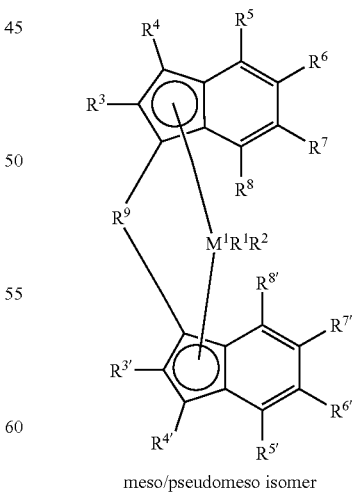

meso/pseudomeso isomer

The present invention also includes a process for producing the transition-metal compounds of the invention.

An object of the invention is thus a process for producing compounds of formulas 1a-1d $R^9L^1L^2M^1R^1R^2$ (Formula 1a)

(Formulas 1b-1d)

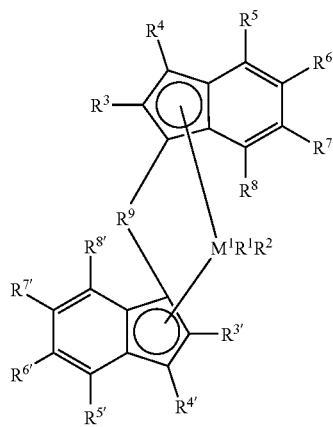

in which the variables L, R and $M^1$ have the meaning specified above, including the preferred embodiments, comprising the steps of:

a) Deprotonation of the compound of formula 2:

(Formula 2)

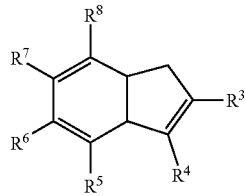

with a base, in which $R^3$, $R^4$, $R^5$, $R^6$, $R^7$, and $R^8$ have the meaning specified above.

b) If $R^9$ has the meaning $M^{12}R^{40}R^{41}$, where $M^{12}$, $R^{40}$, and $R^{41}$ have the meanings specified above, then the further production proceeds by the reaction of the deprotonated compound from step (a) with $R^{40}R^{41}M^{12}X_2$ to form the compound of formula 3 or formula 4, depending on the quantitative proportions used, where $R^{40}$, $R^{41}$, and $M^{12}$ have the meanings specified above, and X may be the same or different and means a halogen atom, preferably chlorine, bromine, or iodine, or another leaving group, preferably triflate, tosylate, or mesylate.

(Formula 3)

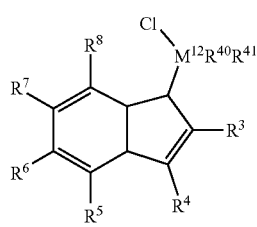

(Formula 4)

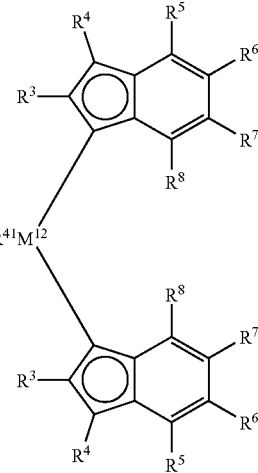

c) In the production of chlorosilane indenes or chlorogermane indenes of formula 3, these are reacted with a metal-indene compound of formula (Formula 5)

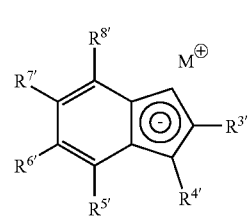

in which M stands for Li, Na, or K, and $R^{3'}$, $R^{4'}$, $R^{5'}$, $R^{6'}$, $R^{7'}$, and $R^{8'}$ have the meanings specified above, to obtain the compound of formula 6.

(Formula 6)

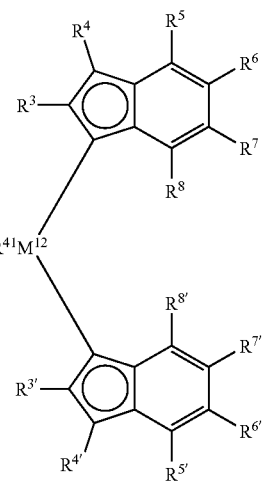

d) Reaction of the compound of formula 4 or 6 with a base and addition of $M^1Cl_4$, in which $M^1$ stands for zirconium, titanium, or hafnium, to form the compound of formulas 1a-1d.

In step (a), the compound of formula 2, for example, 2-methyl-7-(4'-tert-butylphenyl)indene in an inert solvent, which consists of one or more aromatic or aliphatic hydrocarbons and/or one or more polar, aprotic solvents, is deprotonated with a strong base, for example, n-butyllithium. The deprotonation is carried out at temperatures of −70° C. to 80° C., and preferably 0° C. to 80° C. The resulting metal salt is then reacted directly, without further isolation, in step (b) with a silicon compound or germanium compound that contains two leaving groups. Preferential production of the compound of formula 3 or the compound of formula 4 can be achieved by adjustment of the quantitative proportions. Compounds of formula 3 are reacted in step (c) with a metal-indenyl compound of formula 5. In the following step (d), the bis(indenyl)silanes of formula 4 or 6 are doubly deprotonated with a strong base, such as n-butyllithium, in an inert solvent, which consists of one or more aromatic or aliphatic hydrocarbons and/or one or more polar, aprotic solvents, and the bislithium salt formed in this way is reacted, without isolation, directly with a source of Ti, Zr, or Hf to obtain the compound of formula 1a-1d. The deprotonation is carried out at temperatures of −70° C. to 80° C., and preferably 0° C. to 80° C. Depending on the nature of the bridge $R^9$ and the bridge $R^{40}R^{41}M^{12}$ respectively, the metallocenes are isolated from the reaction mixture with rac:meso ratios or pseudo-rac:meso ratios of greater than 5:1 preferably of at least 10:1, more preferred of at least 15:1 and most preferred of at least 20:1 without any further rac:meso separation steps.

That is, a significant feature of the invention is that the process described herein provides a composition having a mixture of isomers of the compounds specified herein having a racemic or pseudoracemic to meso or pseudomeso weight ratio of greater than 5:1 (i.e., the meso or pseudomeso isomer is less than 16% of the mixture) as synthesized. The terms "as synthesized" or "as prepared" as used herein refer to the material as isolated from the reaction mixture without any subsequent separation of racemic or pseudoracemic isomers from meso or pseudomeso isomers. This feature provides a significant advantage in obviating the need for time consuming and expensive separation of rac and meso isomers to obtain a suitable catalyst.

In the following diagrams 1 and 2, the individual steps of the process of the invention for producing transition-metal compounds of formulas 1a-1d are shown once again for the example of a preferred embodiment.

Diagram 1

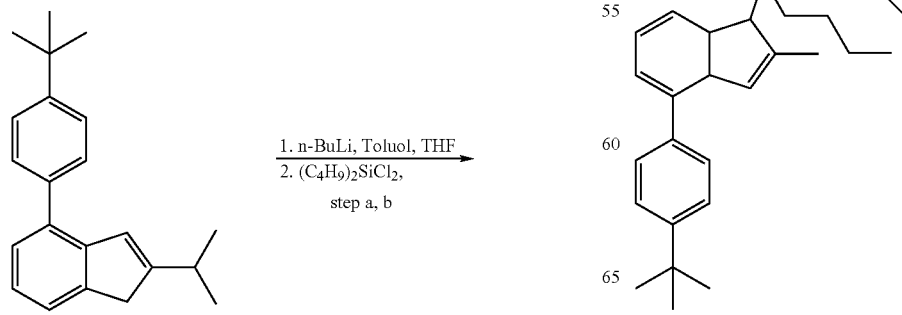

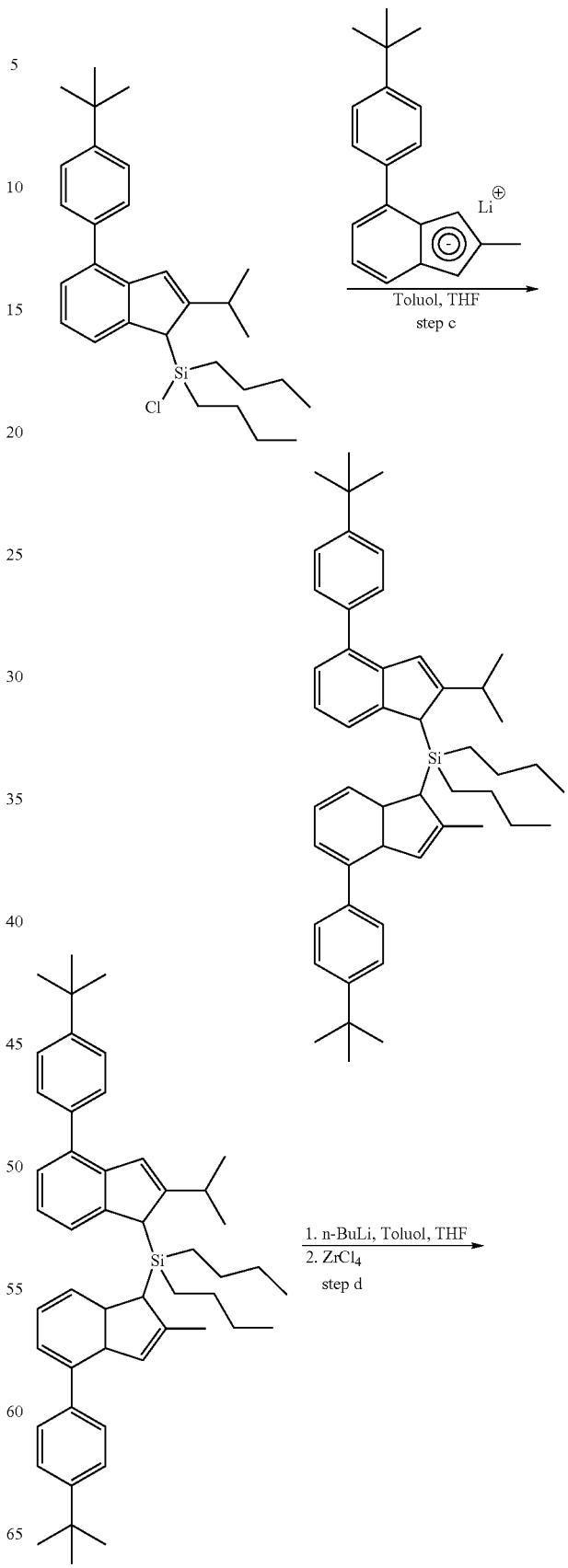

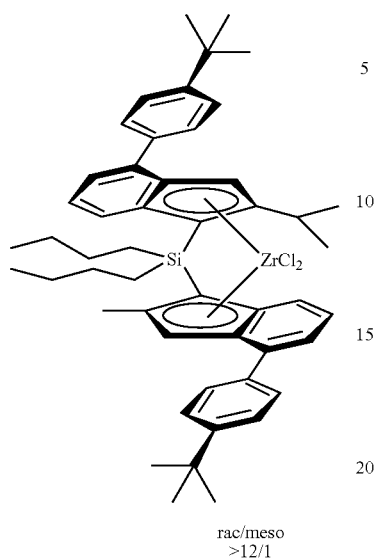

rac/meso >12/1

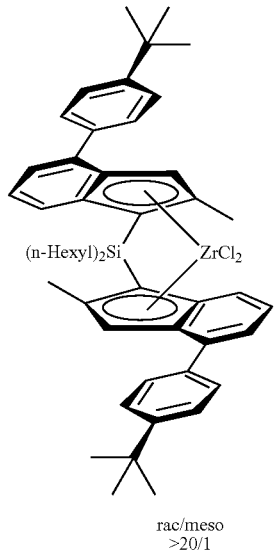

rac/meso >20/1

In addition, the present invention relates to a catalyst system comprising at least one compound of formulas 1a-1d and at least one cocatalyst.

A suitable cocatalyst component which may be present according to the present invention in the catalyst system comprises at least one compound of the type of an aluminoxane, a Lewis acid or an ionic compound which reacts with a metallocene to convert the latter into a cationic compound.

As aluminoxane, preference is given to using a compound of the formula 7.

(R—Al—O) (Formula 7)

Aluminoxanes may be, for example, cyclic as in formula 8

(Formula 8)

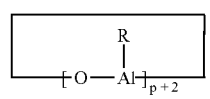

or linear as in formula 9

(Formula 9)

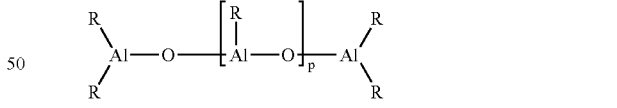

or of the cluster type as in formula 10, as described in recent literature, cf. JACS 117 (1995), 6465-74, Organometallics 13 (1994), 2957-2969.

(Formula 10)

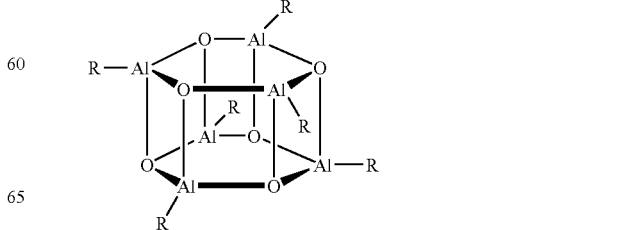

Diagram 2

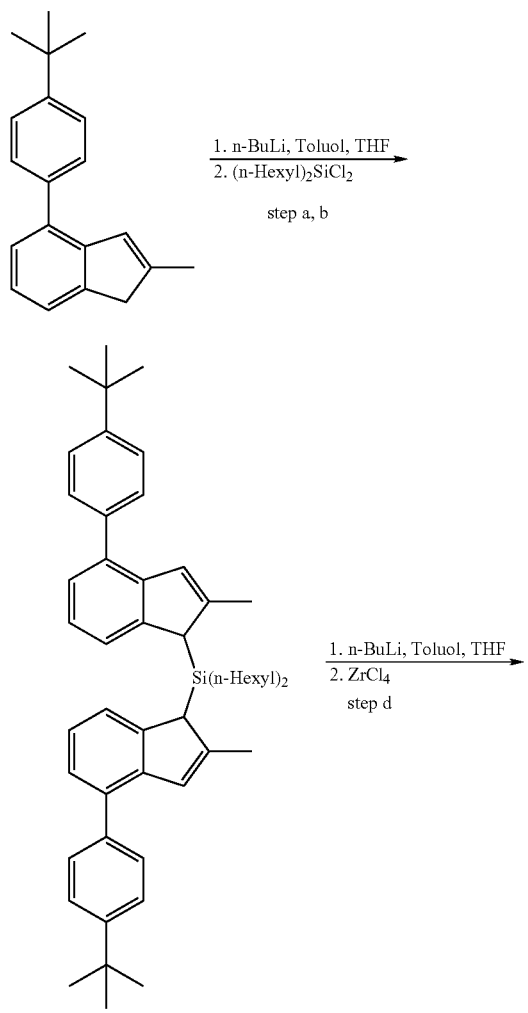

The radicals R in the formulas (7), (8), (9) and (10) can be identical or different and are each a $C_1$-$C_{20}$ group such as an alkyl group of from 1 to about 6 carbon atoms, an aryl group of from 6 to about 18 carbon atoms, benzyl or hydrogen and p is an integer from 2 to 50, preferably from 10 to 35.

Peferably, the radicals R are identical and are methyl, isobutyl, n-butyl, phenyl or benzyl, particularly preferably methyl.

If the radicals R are different, they are preferably methyl and hydrogen, methyl and isobutyl or methyl and n-butyl, with hydrogen, isobutyl or n-butyl preferably being present in a proportion of from 0.01 to 40% (number of radicals R).

The aluminoxane can be prepared in various ways by known methods. One of the methods comprises the reaction of an aluminum-hydrocarbon compound and/or a hydridoaluminum-hydrocarbon compound with water, which may be gaseous, solid, liquid or bound as water of crystallization, in an inert solvent such as toluene. To prepare an aluminoxane having different alkyl groups R, two different trialkylaluminums ($AlR_3$+$AlR'_3$) corresponding to the desired composition and reactivity are reacted with water, cf. S. Pasynkiewicz, Polyhedron 9 (1990) 429 and EP-A-0 302 424.

Regardless of the method of preparation, all aluminoxane solutions have in common a variable content of unreacted aluminum starting compound which is present in free form or as an adduct.

Furthermore, instead of the aluminoxane compounds of the formulas 7, 8, 9 or 10, it is also possible to use modified aluminoxanes in which the hydrocarbon radicals or hydrogen atoms have been partly replaced by alkoxy, aryloxy, siloxy or amide radicals.

The amounts of aluminoxane and metallocene used in the preparation of the supported catalyst system can be varied within a wide range. However, it has been found to be advantageous to use the metallocene compound of formulas 1a -1d and the aluminoxane compounds in such amounts that the atomic ratio of aluminum from the aluminoxane compounds to the transition metal from the metallocene compound is in the range from 10:1 to 1000:1, preferably from 20:1 to 500:1 and in particular in the range from 30:1 to 400:1. In the case of methylaluminoxane, preference is given to using ≧30% strength toluene solutions, but the use of 10% strength solutions is also possible.

As Lewis acid, preference is given to using compounds of the formula 11

$$M^2X^1X^2X^3 \qquad \text{(Formula 11)}$$

where $M^2$ is an element of Group 13 of the Periodic Table of Elements, in particular B, Al or Ga, preferably B or Al, $X^1$, $X^2$ and $X^3$ are the same or different and each are a hydrogen atom, an alkyl group of from 1 to about 20 carbon atoms, an aryl group of from 6 to about 15 carbon atoms, alkylaryl, arylalkyl, haloalkyl or haloaryl each having from 1 to 10 carbon atoms in the alkyl radical and from 6-20 carbon atoms in the aryl radical or fluorine, chlorine, bromine or iodine. Preferred examples for $X^1$, $X^2$ and $X^3$ are methyl, propyl, isopropyl, isobutyl or trifluoromethyl, unsaturated groups such as aryl or haloaryl like phenyl, tolyl, benzyl groups, p-fluorophenyl, 3,5-difluorophenyl, pentachlorophenyl, pentafluorophenyl, 3,4,5-trifluorophenyl and 3,5-di(trifluoromethyl)phenyl.

Preferred Lewis acids are trimethylaluminium, triethylaluminum, triisobutylaluminum, tributylaluminum, trifluoroborane, triphenylborane, tris(4-fluorophenyl)borane, tris (3,5-difluorophenyl)borane, tris(4-fluoromethylphenyl) borane, tris(2,4,6-trifluorophenyl)borane, tris(pentafluorophenyl)borane, tris(tolyl)borane, tris(3,5-dimethylphenyl)borane, tris(3,5-difluorophenyl)borane and/or tris(3, 4,5-trifluorophenyl)borane.

Particular preference is given to tris(pentafluorophenyl) borane.

As ionic cocatalysts, preference is given to using compounds which contain a non-coordinating anion such as tetrakis(pentafluorophenyl)borate, tetraphenylborate, $SbF_6^-$, $CF_3SO_3^-$ or $ClO_4^-$. Suitable counterions are either Lewis acid or Broenstedt acid cation.

As Broensted acids, particular preference is given to protonated amine or aniline derivatives such as methylammonium, anilinium, dimethylammonium, diethylammonium, N-methylanilinium, diphenylammonium, N,N-dimethylanilinium, trimethylammonium, triethylammonium, tri-n-butylammonium, methyldiphenylammonium, pyridinium, p-bromo-N,N-dimethylanilinium or p-nitro-N,N-dimethylanilinium, Suitable Lewis-acid cations are cations of the formula 12

$$[(Y^{a+})Q_1Q_2 \ldots Q_z]^{d+} \qquad \text{(Formula 12)}$$

where Y is an element of Groups 1 to 16 of the Periodic Table of the Elements, $Q_1$ to $Q_z$ are singly negatively charged groups such as $C_1$-$C_{28}$-alkyl, $C_6$-$C_{15}$-aryl, alkylaryl, arylalkyl, haloalkyl, haloaryl each having from 6 to 20 carbon atoms in the aryl radical and from 1 to 28 carbon atoms in the alkyl radical, cycloalkyl groups of from 3 to about 10 carbon atoms, which may in turn bear alkyl groups of from 1 to about 10 carbon atoms as substitutents, halogen, alkoxy groups of from 1 to 28 carbon atoms, aryloxy groups of from 6 to 15 carbon atoms, silyl or mercaptyl groups.

a is an integer from 1-6, z is an integer from 0 to 5 and d corresponds to the difference a-z, but d is larger than or equal to 1

Particularly suitable cations are carbonium cations such as triphenylcarbenium, oxonium cations, sulfonium cations such as tetrahydrothiophenium, phosphonium cations such as triethylphosphonium, triphenylphosphonium and diphenylphosphonium, and also cationic transition metal complexes such as the silver cation and the 1,1'-dimethylferrocenium cation.

Preferred ionic compounds which can be used according to the present invention include:
triethylammoniumtetra(phenyl)borate,
tributylammoniumtetra(phenyl)borate,
trimethylammoniumtetra(tolyl)borate,
tributylammoniumtetra(tolyl)borate,
tributylammoniumtetra(pentafluorophenyl)borate,
tributylammoniumtetra(pentafluorophenyl) aluminate,
tripropylammoniumtetra(dimethylphenyl)borate,
tributylammoniumtetra(trifluoromethyl phenyl)borate,
tributylammoniumtetra(4-fluorophenyl)borate,
N,N-dimethylcyclohexylammoniumtetrakis(pentafluorophenyl)borate,
N,N-dimethylbenzylammoniumtetrakis(pentafluorophenyl) borate
N,N-dimethylaniliniumtetra(phenyl)borate,
N,N-diethylaniliniumtetra(phenyl)borate,
N,N-dimethylaniliniumtetrakis(pentafluorophenyl)borate,
N,N-dimethylaniliniumtetrakis(pentafluorophenyl)aluminate,
di(propyl)ammoniumtetrakis(pentafluorophenyl)borate, di(cyclohexyl)ammoniumtetrakist(pentafluorophenyl)borate,
triphenylphosphoniumtetrakis(phenyl)borate,
triethylphosphoniumtetrakis(phenyl)borate,
diphenylphosphoniumtetrakis(phenyl)borate,
tri(methylphenyl)phosphoniumtetrakis(phenyl)borate,
tri(dimethylphenyl)phosphoniumtetrakis(phenyl)borate,
triphenylcarbeniumtetrakis(pentafluorophenyl)borate,
triphenylcarbeniumtetrakis(pentafluorophenyl)aluminate,
triphenylcarbeniumtetrakis(phenyl)aluminate,
ferroceniumtetrakis(pentafluorophenyl)borate and/or
ferroceniumtetrakis(pentafluorophenyl)aluminate, Preference is given to triphenylcarbeniumtetrakis(pentafluorophenyl) borate, N,N-dimethylcyclohexylammoniumtetrakis(pentafluorophenyl)borate or N,N-dimethylbenzylammoniumtetrakis(pentafluorophenyl)borate.

It is also possible to use mixtures of all of the above and below mentioned cation-forming compounds. Preferred mixtures comprise aluminoxanes and an ionic compound, and/or a Lewis acid.

Other useful cocatalyst components are likewise borane or carborane compounds such as
7,8-dicarbaundecaborane(13),
undecahydrido-7,8-dimethyl-7,8-dicarbaundecaborane,
dodecahydrido-1-phenyl-1,3-dicarbanonaborane,
tri(butyl)ammoniumun decahydrido-8-ethyl-7,9-dicarbaundecaborate,
4-carbanonaborane(14),
bis(tri(butyl)ammonium)nonaborate,
bis(tri(butyl)ammonium)undecaborate,
bis(tri(butyl)ammonium)dodecaborate,
bis(tri(butyl)ammonium)decachlorodecaborate,
tri(butyl)ammonium-1-carbadecaborate,
tri(butyl)ammonium-1-carbadodecaborate,
tri(butyl)ammonium-1-trimethylsilyl-1-carbadecaborate,
tri(buyl)ammoniumbis(nonahydrido-1,3-dicarbanonaborato)cobaltate(III),
tri(butyl)ammonium bis(undecahydrido-7,8-dicarbaundecaborato)ferrate(III).

The amount of Lewis acids or ionic compounds having Lewis-acid or Broensted-acid cations is preferably from 0.1 to 20 equivalents, preferably from 1 to 10 equivalents, based on the metallocene compound of the formulas 1a-1d.

Combinations of at least one Lewis base with bimetallic compounds of the type $R_i^{17}M^3(-O-M^3R_j^{18})_v$, or $R_i^{18}M^3(-O-M^3R_j^{17})_v$, (formula 13), as described in Patent Application WO 99/40,129, are likewise important as cocatalyst systems.

In this regard, $R^{17}$ and $R^{18}$ are the same or different and represent a hydrogen atom, a halogen atom, a $C_1$-$C_{40}$ carbon-containing group, especially an alkyl group of from 1 to about 20 carbon atoms, haloalkyl of from 1 to about 20 carbon atoms, alkoxy of from 1 to about 10 carbon atoms, aryl of from 6 to about 20 carbon atoms, haloaryl of from 6 to about 20 carbon atoms, aryloxy of from 6 to about 20 carbon atoms, arylalkyl of from 7 to about 40 carbon atoms, haloarylalkyl of from 7 to about 40 carbon atoms, alkylaryl of from 7 to about 40 carbon atoms, or haloalkylaryl of from 7 to about 40 carbon atoms. $R^{17}$ may also be an $-OSiR^{51}_3$ group, in which the $R^{51}$ groups are the same or different and have the same meaning as $R^{17}$, $M^3$ is the same or different and represents an element of main group III of the periodic table of elements, i, j, and v each stands for a whole number 0, 1, or 2, and i+j+v is not equal to 0.

Preferred cocatalyst systems are the compounds of formulas (A) and (B)

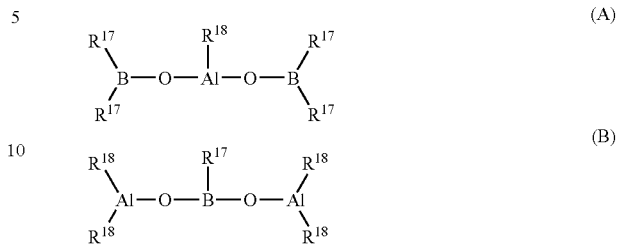

where $R^{17}$ and $R^{18}$ have the same meaning as specified above.

Furthermore, compounds that are generally to be regarded as preferred are those formed by the reaction of at least one compound of formulas (C) and/or (D) and/or (E) with at least one compound of formula (F).

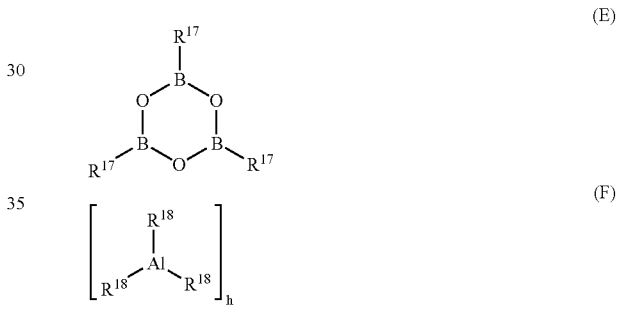

in which
$R^{27}$ may be a hydrogen atom or a boron-free $C_1$-$C_{40}$ carbon-containing group, such as an alkyl of from 1 to about 20 carbon atoms, aryl of from 6 to about 20 carbon atoms, arylalkyl of from 7 to about 40 carbon atoms, and alkylaryl of from 7 to about 40 carbon atoms, and in which $R^{17}$, $R^{18}$ have the same meaning as specified above, D is an element of main Group VI of the periodic table of elements or an $NR^{61}$ group, where $R^{61}$ is a hydrogen atom or a $C_1$-$C_{20}$ hydrocarbon group, such as alkyl of from 1 to about 20 carbon atoms or aryl of from 6 to about 20 carbon atoms, f is a whole number from 0 to 3,
g is a whole number from 0 to 3 with z+y not equal to 0, and
h is a whole number from 1 to 10.

The bimetallic compounds of formula 13 are possibly combined with an organometallic compound of formula 14, i.e., $[M^4R^{19}_q]_k$, in which $M^4$ is an element of main Group I, II, or III of the periodic table of the elements, $R^{19}$ is the same or different and represents a hydrogen atom, a halogen atom, a $C_1$-$C_{40}$ carbon-containing group, an alkyl group of from 1 to about 20 carbon atoms, an aryl group of from about 6 to about 40 carbon atoms, arylalkyl of from 7 to about 40 carbon atoms, and alkylaryl of from 7 to about 40 carbon atoms, q is a whole number from 1 to 3, and k is a whole number from 1 to 4.

The organometallic compounds of formula 14 are preferably neutral Lewis acids, in which $M^4$ stands for lithium, magnesium, and/or aluminum, especially aluminum. Examples of preferred organometallic compounds of formula 14 are trimethylaluminum, triethylaluminum, triisopropylaluminum, trihexylaluminum, trioctylaluminum, tri-n-butylaluminum, tri-n-propylaluminum, triisoprene aluminum, dimethyl aluminum monochloride, aluminum monochloride, diisobutyl aluminum monochloride, methyl aluminum sesquichloride, ethyl aluminum sesquichloride, dimethyl aluminum hydride, aluminum hydride, diisopropyl aluminum hydride, dimethyl aluminum(trimethylsiloxide), dimethyl aluminum(triethylsiloxide), phenylalan, pentafluorophenylalan, and o-tolylalan.

The catalyst system of the invention contains an organoboroaluminum compound, which contains units of formula 13, as the cocatalytically active chemical compound. Compounds of formula 13 in which $M^3$ stands for boron or aluminum are preferred. The compounds that contain units of formula 13 may be present as monomers or as linear, cyclic, or cage-like oligomers. Two or more chemical compounds that contain units of formula 13 may also form dimers, trimers, or higher combinations among themselves by Lewis acid-base interactions.

Preferred cocatalytically active bimetallic compounds correspond to formulas 15 and 16,

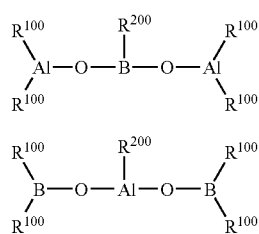

(formula 15)

(formula 16)

in which $R^{100}$ and $R^{200}$ have the same meaning as the substituents $R^{17}$ and $R^{18}$ in formula 13.

Examples of the cocatalytically active compounds of formulas 15 and 16 are

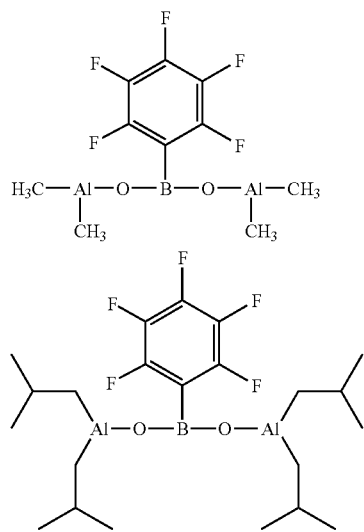

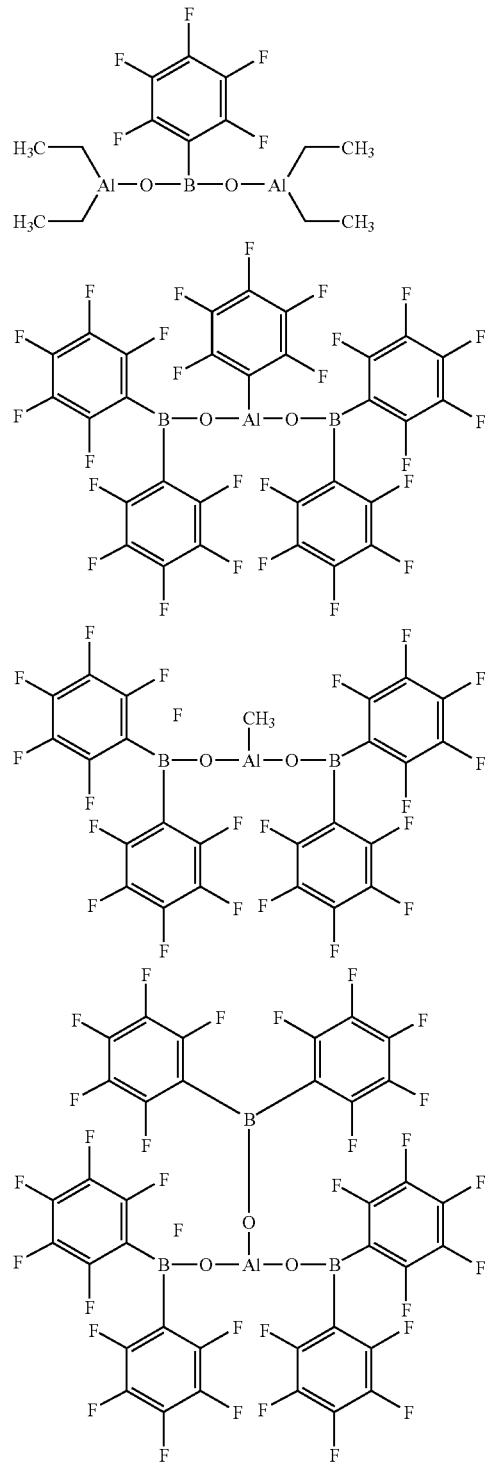

The compounds named in EP-A-924,223, DE 196 22 207.9, EP-A-601,830, EP-A-824,112, EP-A-824,113, WO 99/06,414, EP-A-811,627, WO 97/11,775, DE 196 06 167.9 and DE 198 04 970 are to be used as additional cocatalysts, which may be present in unsupported or supported form.

The amount of cocatalysts of formula 13 and/or 15 and/or 16 used in the catalyst of the present invention can vary from 0.1 to 500 equivalents, preferably from 1 to 300 equivalents, most preferably from 5 to 150 equivalents, based on the used amount of metallocene compound of the formulas 1a-1d.

The catalyst system of the present invention can further comprise, as additional component, a metal compound of the formula 17,

  (Formula 17)

wherein

M$^5$ is an alkali, an alkali earth metal or a metal of Group 13 of the Periodic Table of the Elements, R$^{22}$ is a hydrogen atom, alkyl of from 1 to about 10 carbon atoms, aryl of from 6 to about 15 carbon atoms, or alkylaryl or arylalkyl each having from 1 to 10 carbon atoms in the alkyl part and from 6 to 20 carbon atoms in the aryl part, R$^{23}$ and R$^{24}$ are each a hydrogen atom, a halogen atom, alkyl of from 1 to about 10 carbon atoms, $C_6$-$C_{15}$-aryl of from about 6 to about 15 carbon atoms, or alkylaryl, arylalkyl or alkoxy each having from 1 to 10 carbon atoms in the alkyl part and from 6 to 20 carbon atoms in the aryl radical, r is an integer from 1 to 3 and s and t are integers from 0 to 2, where the sum r+s+t corresponds to the valence of M$^5$, where this component is not identical with the above mentioned cocatalyst compounds. It is also possible to use mixtures of various metal compounds of the formula 17.

Among the metal compounds of the formula 17 preference is given to those in which M$^5$ is lithium, magnesium or aluminum and R$^{23}$ and R$^{24}$ are each alkyl of from 1 to about 10 carbon atoms. Particularly preferred metal compounds of the formula 17 are n-butyllithium, n-butyl-n-octyl-magnesium, n-butyl-n-heptylmagnesium, tri-n-hexylaluminum, triisobutylaluminum, triethylaluminum, trimethylaluminum or mixtures thereof.

If a metal compound of the formula 17 is used, it is preferably present in the catalyst system in such an amount that the molar ratio of M$^5$ to the transition metal from the metallocene compound of formulas 1a-1d is from 800:1 to 1:1, in particular from 200:1 to 2:1.

The support component of the catalyst system of the present invention can be any organic or inorganic inert solid, in particular a porous support such as hydrotalcites, talc, inorganic oxides and finely divided polymer powders.

Suitable inorganic oxides, which are preferably employed include from the Periodic Table of Elements Groups 2, 3, 4, 5, 13, 14, 15 and 16 metal oxides such as silicon dioxide, aluminum oxide, aluminosilicates, zeolites, MgO, $ZrO_2$, $TiO_2$ or $B_2O_3$, CaO, ZnO, $ThO_2$, $Na_2O$, $K_2O$, $LiO_2$ or mixed oxides like Al/Si oxides, Mg/Al oxides or Al/Mg/Si oxides. Other suitable inorganic support materials are $Na_2CO_3$, $K_2CO_3$, $CaCO_3$, $MgCl_2$, $Na_2SO_4$, $Al_2(SO_4)_3$, $BaSO_4$, $KNO_3$, $Mg(NO_3)_2$ and $Al(NO_3)_3$.

Suitable polymer powders are homopolymers, copolymers, crosslinked polymers or polymer blends. Examples of such polymers are polyethylene, polypropylene, polybutene, polystyrene, divinylbenzene-crosslinked polystyrene, polyvinyl chloride, acrylonitrile-butadien-styrene copolymer, polyamide, polymethacrylate, polycarbonate, polyester, polyacetal or polyvinyl alcohol.

The preferred support materials have a specific surface area in the range from 10 to 1000 m$^2$/g, a pore volume in the range from 0.1 to 5 cm$^3$/g and a mean particle size of from 1 to 500 µm. Preference is given to supports having a specific surface area in the range from 50 to 500 m$^2$/g, a pore volume in the range from 0.5 to 3.5 cm$^3$/g and a mean particle size in the range from 5 to 250 µm. Particular preference is given to supports having a specific surface area in the range from 200 to 400 m$^2$/g, a pore volume in the range from 0.8 to 3.0 cm$^3$/g and a mean particle size of from 10 to 100 µm.

The support materials can thermally and chemically be pretreated in order to adjust certain properties of the carrier (e.g. the water or the hydroxyl group content).

If the support material has a low moisture content or residual solvent content, dehydration or drying before use can be omitted. If this is not the case, as when using silica gel as support material, dehydration or drying is advisable. Thermal dehydration or drying of the support material can be carried out under reduced pressure with simultaneous inert gas blanketing (nitrogen). The drying temperature is in the range from 100° C. to 1000° C., preferably from 150° C. to 800° C. The pressure is not crucial in this case. The duration of the drying process can be from 1 to 24 hours. But shorter or longer drying periods are also possible.

In addition or alternatively, dehydration or drying of the support material can also be carried out by chemical means, by reacting the adsorbed water and/or the surface hydroxyl groups with suitable passivating agents. Reaction with the passivating reagent can convert the hydroxyl groups completely or partially into a form, which does not show any adverse interaction with the catalytically active centers. Suitable passivating agents are silicon halides, silanes or amines, eg. silicon tetrachloride, chlorotrimethylsilane, dichlorodialkylsilanes, dimethylaminotrichlorosilane, N,N-dimethylanilin or N,N-dimethylbenzylamine or organometallic compounds of aluminum, boron and magnesium, eg. aluminoxanes, trimethylaluminum, triethylaluminum, triisobutylaluminum, triethylborane or dibutylmagnesium. The chemical dehydration or passivation of the support material is carried out by reacting, under the exclusion of air and moisture, a suspension of the support material in a suitable solvent with the passivating reagent in pure form or dissolved in a suitable solvent. Suitable solvents are aliphatic or aromatic hydrocarbons such as pentane, hexane, heptane, toluene or xylene. The passivation is carried out at temperatures from 25° C. to 120° C., preferably from 50° C. to 70° C. Higher and lower temperatures are possible. The duration of the reaction is from 30 minutes to 20 hours, preferably from 1 to 5 hours. After the chemical dehydration is complete, the support material is isolated by filtration under inert conditions, washed one or more times with suitable inert solvents as described above and subsequently dried in a stream of inert gas or under reduced pressure.

As outlined above, organic support materials such as finely divided polyolefin powders, can also be used and should, before use, likewise be freed from any adhering moisture, solvent residues or other impurities by means of appropriate purification and drying operations.

The supported catalyst system according to this invention can be made in various ways.

In one embodiment of the present invention, at least one of the above-described metallocene components of formulas 1a-1d is brought into contact in a suitable solvent with at least one cocatalyst component, preferably giving a soluble reaction product, an adduct or a mixture. The obtained composition is mixed with the dehydrated or passivated support material, the solvent is removed and the resulting supported metallocene catalyst system is dried to ensure that the solvent is completely or mostly removed from the pores of the support material. The supported catalyst is obtained as a free-flowing powder.

As an example, the process for preparing a free-flowing and, if desired, prepolymerized supported catalyst system comprises the following steps:

a) preparing a metallocene/cocatalyst mixture in a suitable solvent or suspension medium, where the metallocene component has one of the above-described structures, b) applying the metallocene/cocatalyst mixture to a porous, preferably inorganic, if necessary thermally or chemically pretreated support, c) removing the major part of solvent from the resulting mixture, d) isolating the supported catalyst system and e) if desired, prepolymerizing the resulting supported catalyst system with one or more olefinic monomer(s), to obtain a prepolymerized supported catalyst system.

In another embodiment of this invention the metallocene/cocatalyst composition is mixed with the dehydrated or passivated support material, the supported catalyst is recovered and optionally washed with an aromatic hydrocarbon and/or paraffinic hydrocarbon solvent. The isolated catalyst is then dispersed in a non-reactive suspension media such as a paraffinic hydrocarbon solvent, a mineral oil or a wax.

In a further embodiment of this invention the catalyst is prepared according to the procedure disclosed in WO 00/05277 and WO 98/01481 (corresponding to EP 0 909 279 B1 and U.S. Pat. No. 6,265,339).

In an even further embodiment of the present invention a free flowing and, if desired, prepolymerized supported catalyst system is prepared comprising the following steps:

a) preparing a trialkylaluminium/borinic acid mixture in a suitable solvent or suspension medium b) applying the trialkylaluminium/borinic acid mixture to a porous, preferably inorganic, if necessary thermally or chemically pretreated support, which was prior treated with a base c) removing the major part of solvent from the resulting mixture to obtain a supported cocatalyst, d) preparing a metallocene/supported cocatalyst mixture in a suitable solvent or suspension medium, where the metallocene component has one of the above-described structures, e) isolating the supported catalyst system and f) if desired, prepolymerizing the resulting supported catalyst system with one or more olefinic monomer(s), to obtain a prepolymerized supported catalyst system.

Preferred solvents for the preparation of the metallocene/cocatalyst mixture are hydrocarbons and hydrocarbon mixtures, which are liquid at the selected reaction temperature and in which the individual components preferably dissolve. The solubility of the individual components is, however, not a prerequisite as long as it is ensured that the reaction product of metallocene and cocatalyst components is soluble in the solvent selected. Suitable solvents are alkanes such as pentane, isopentane, hexane, isohexane, heptane, octane and nonane, cycloalkanes such as cyclopentane and cyclohexane and aromatics such as benzene, toluene, ethylbenzene and diethylbenzene. Very particular preference is given to toluene, heptane and ethylbenzene.

For a preactivation, the metallocene in the form of a solid is dissolved in a solution of the cocatalyst in a suitable solvent. It is also possible to dissolve the metallocene separately in a suitable solvent and subsequently to combine this solution with the cocatalyst solution. Preference is given to using toluene. The preactivation time is from 1 minute to 200 hours. The preactivation can take place at room temperature of 25° C. In individual cases, the use of higher temperatures can reduce the required preactivation time and give an additional increase in activity. Elevated temperatures in this case refer to a range from 25° C. to 100° C.

The preactivated solution or the metallocene/cocatalyst mixture is subsequently combined with an inert support material, usually silica gel, which is in the form of a dry powder or as a suspension in one of the above mentioned solvents. The support material is preferably used as powder. The preactivated metallocene/cocatalyst solution or the metallocene/cocatalyst mixture can be either added to the initially charged support material, or else the support material can be introduced into the initially charged solution.

The volume of the preactivated solution or the metallocene/cocatalyst mixture can exceed 100% of the total pore volume of the support material used or else be up to 100% of the total pore volume.

The temperature at which the preactivated solution or the metallocene/cocatalyst mixture is brought into contact with the support material can vary within the range from 0° C. to 100° C. However, lower or higher temperatures are also possible.

While the solvent is completely or mostly removed from the supported catalyst system, the mixture can be stirred and, if desired, also heated. Preferably, both the visible portion of the solvent and the portion in the pores of the support material are removed. The removal of the solvent can be carried out in a conventional way using reduced pressure and/or purging with inert gas. During the drying process, the mixture can be heated until the free solvent has been removed, which usually takes from 1 to 3 hours at a preferred temperature of from 30° C. to 60° C. The free solvent is the visible portion of the solvent in the mixture. For the purposes of the present invention, residual solvent is the portion present in the pores.

As an alternative to the complete removal of the solvent, the supported catalyst system can also be dried until only a certain residual solvent content is left, with the free solvent having been completely removed. Subsequently, the supported catalyst system can be washed with a low-boiling hydrocarbon such as pentane or hexane and dried again.

The supported catalyst system prepared according to the present invention can be used either directly for the polymerization of olefins or be prepolymerized with one or more olefinic monomers, with or without the use of hydrogen as molar mass regulating agent, prior to use in a polymerization process. The procedure for the prepolymerization of supported catalyst systems is described in WO 94/28034.

As additive, it is possible to add, during or after the preparation of the supported catalyst system, a small amount of an olefin, preferably an alpha-olefin such as styrene or phenyldimethylvinylsilane as activity-increasing component or an antistatic, as described in U.S. Ser. No. 08/365,280. The molar ratio of additive to metallocene component of formulas 1a-1d is preferably from 1:1000 to 1000:1, very particularly preferably from 1:20 to 20:1.

The present invention also provides a process for preparing a polyolefin by polymerization of one or more olefins in the presence of the catalyst system of the present invention comprising at least one transition metal component of the formulas 1a-1d. For the purposes of the present invention, the term polymerization refers to both homopolymerization and copolymerization and the term copolymerization includes terpolymerisation or copolymerisation of more than three different monomers.

Preference is given to polymerizing olefins of the formula $R'''$—CH═CH—$R''$, where $R'''$ and $R''$ are identical or different and are each a hydrogen atom or a radical having from 1 to 20 carbon atoms, in particular from 1 to 10 carbon atoms, and R'" and R" together with the atoms connecting them can form one or more rings.

Suitable olefins are 1-olefins, eg. ethene, propene, 1-butene, 1-pentene, 1-hexene, 4-methyl-1-pentene or 1-octene, styrene, dienes such as 1,3-butadiene, 1,4-hexadiene, vinylnorbornene, norbornadiene, ethylnorbornadiene and cyclic olefins such as norbornene, tetracyclododecene or methylnorbornene. In the process of the present invention, preference is given to homopolymerizing propene or ethene or copolymerizing propene with ethene and/or one or more 1-olefins having from 4 to 20 carbon atoms, eg. 1-butene or hexene, and/or one or more dienes having from 4 to 20 carbon atoms, eg. 1,4-butadiene, norbornadiene, ethylidenenorbornene or ethylnorbornadiene. Very suitable copolymers are ethene-propene copolymers, propene-1-pentene copolymers and ethene-propene-1-butene, ethene-propene-1-pentene or ethene-propene-1,4-hexadiene terpolymers.

The polymerization is carried out at from −60° C. to 300° C., preferably from 50° C. to 200° C., very particularly preferably from 50° C. to 95° C. The pressure is from 0.5 to 2000 bar, preferably from 5 to 100 bar.

The polymerization can be carried out in solution, in bulk, in suspension or in the gas phase, continuously or batchwise, in one or more stages. As an example, impact copolymers are preferably produced in more than one stage. The homopolymer or random copolymer content of such a polymer can be produced in (a) first stage(s) and the copolymer rubber content can be produced in (a) consecutive stage(s).

The supported catalyst system prepared according to the present invention can be used as sole catalyst component for the polymerization of olefins or preferably in combination with at least one alkyl compound of elements of main Groups I to III of the Periodic Table, for example an aluminum alkyl, magnesium alkyl or lithium alkyl or an aluminoxane. The alkyl compound is added to the monomer or suspension medium and serves to free the monomer of substances, which can impair the catalytic activity. The amount of alkyl compound added depends on the quality of the monomers used.

To prepare olefin polymers having a broad or bimodal molecular weight distribution or a broad or bimodal melting range, it is recommended to use a catalyst system comprising two or more different metallocenes and/or two or more different cocatalysts. Alternatively two or more different catalyst systems of the present invention can be used as a mixture.

As molar mass regulator and/or to increase the activity, hydrogen is added if required.

The catalyst system may be supplied to the polymerization system as a solid or in the form of a suspension in a hydrocarbon or may be treated with inert components, such as paraffins, oils, or waxes, to achieve better metering. If the catalyst system is to be metered into the reactor together with the monomer to be polymerized or the monomer mixture to be polymerized, the mixing unit and the metering line are preferably cooled.

Furthermore, an additive such as an antistatic or an alcohol can be used in the process of the present invention, for example to improve the particle morphology of the olefin polymer. In general it is possible to use all antistatics which are suitable in olefin polymerization processes. It is preferred to dose the antistatic directly into the polymerization system, either together with or separately from the catalyst system used.

The polymers prepared using the catalyst systems of the present invention display an uniform particle morphology and contain no fines. No agglomerates or deposits are obtained in the polymerization using the catalyst system of the present invention.

The catalyst systems of the present invention give polymers such as polypropylene having high molecular weight and cover a broad range of stereospecificity and regiospecificity.

The copolymers which can be prepared using the catalyst system based on metallocenes of formula 1d of the present invention have a significantly higher molar mass compared to the prior art. At the same time, such copolymers can be prepared using the catalyst system of the present invention at a high productivity and at industrially relevant process parameters without deposit formation.

The polymers prepared by the process of the present invention are suitable, in particular, for producing products such as fibers, filaments, injection-molded parts, films, sheets, caps, closures, bottles or large hollow bodies such as pipes with excellent properties.

EXAMPLES

General Procedures

The preparation and handling of the organometallic compounds were carried out under argon using Schlenk techniques or in a glove box. All solvents were purged with argon and dried over molecular sieves before use.

The polymers produced and the metallocenes used were characterized by
$^1$H-NMR, $^{13}$C-NMR, DSC, GPC and IR spectroscopy.

The following abbreviations are employed:
PP=polypropylene
MC=metallocene
Cat=supported catalyst system
h=hour
VN=viscosity number in cm$^3$/g
$M_w$=weight average molar mass of the polymer in g/mol
$M_w/M_n$=polydispersity, determined by gel permeation chromatography (GPC)
MFR=melt flow rate, measured at 230° C. with a load of 2,16 kg (ISO 1133)
m.p.=polymer melting point in ° C., determined by differential scanning calorimetry (DSC, ISO 3146) with a 1$^{st}$ heating/cooling/2$^{nd}$ heating rate of 20° C./min
$T_g$=glass transition temperature in ° C., determined by differential scanning-calorimetry (DSC, conditions see above)

Example 1

Preparation of Di-n-hexylsilanediylbis(2-methyl-4-(4'-tert-butylphenyl)indene)

10.9 g (41.5 mmoles) of 2-methyl-4-(4'-tert-butylphenyl)-1-indene are introduced into 190 mL of toluene and 11 mL of THF, and 17.4 mL of n-butyllithium (2.5 M in toluene) are added without interruption at room temperature. After this addition is complete, the mixture is heated to 80° C. and stirred at this temperature for one hour. It is allowed to cool to 40° C., and then 5.8 mL (20.7 mmoles) of di-n-hexyldichlorosilane are slowly added dropwise. After this addition, the reaction solution is stirred for three hours at 60° C. and then overnight at room temperature. 60 mL of water are added, and the phases that form are separated. The organic phase is washed with 100 mL of water, and the aqueous phase is extracted three times with a total of 100 mL of toluene. The combined organic phases are dried over magnesium sulfate. After separation of the magnesium sulfate, the solvent is removed and the residue is purified by column chromatography. The desired product di-n-hexylsilanediylbis(2-methyl-4-(4'-tert-butylphenyl)indene) is isolated in a yield of 6.6 g (44%) (purity 98%).

$^1$H-NMR (400 MHz, CDCl$_3$): 7.42-7.04 (m, 14H, arom-H), 6.72 (s, br, 2H, olefin-H indene), 3.60, 3.48 (each s, each 1H, SiC-H), 2.04, 2.02 (each s, each 3H, CH$_3$), 1.33, 1.31 (each s, each 9H, tert-butyl), 1.20-1.02 (m, 16H, aliph-H), 0.78-0.72 (m, 6H, CH$_3$), 0.67-0.50 (m, 4H, aliph-H).

Example 2

Preparation of Di-n-hexylsilanediylbis(2-methyl-4-(4'-tert-butylphenyl)-indenyl)zirconium dichloride 7.3 g (10.1 mmoles) of di-n-hexylsilanediylbis(2-methyl-4-(4'-tert-butylphenyl)indene are introduced into 80 mL of diethyl ether, and 8.1 mL of n-butyllithium solution (2.5 M in toluene) are added at room temperature. After this addition is complete, the mixture is stirred overnight at this temperature. It is cooled to 0° C., and then 2.36 g (10.1 mmoles) of zirconium tetrachloride are added in portions. After the addition of 20 mL of diethyl ether, the mixture is allowed to warm to room temperature and is then stirred for two hours at this temperature. The precipitate that forms is separated through a G3 fritted glass filter and washed once with 20 mL of diethyl ether. The residue is then dried in an oil-pump vacuum. The desired product is obtained in a yield of 4.9 g (55%) and a rac:meso ratio>20:1.

$^1$H-NMR (400 MHz, CDCl$_3$): 7.60-6.96 (m, 16H, arom-H), 2.22 (s, 6H, CH$_3$), 1.87-1.35 (m, 20H, aliph-H), 1.31(s, 18H, tert-butyl), 0.92 (t, 6H, CH$_3$).

Example 1a and Example 2a

Analogous to example 1 and example 2 respectively, the ligand system di-n-propylsilanediylbis(2-methyl-4-(4'-tert-butylphenyl)indene) and the corresponding metallocene di-n-propylsilanediylbis(2-methyl-4-(4'-tert-butylphenyl)-indenyl)zirconium dichloride was synthesized. The desired product is obtained in a rac:meso ratio>8:1.

Example 1b and Example 2b

Analogous to example 1 and example 2 respectively, the ligand system di-n-butylsilanediylbis(2-methyl-4-(4'-tert-butylphenyl)indene) and the corresponding metallocene di-n-butylsilanediylbis(2-methyl-4-(4'-tert-butylphenyl)-indenyl)zirconium dichloride was synthesized. The desired product is obtained in a rac:meso ratio>12:1.

Example 1c and Example 2c

Analogous to example 1 and example 2 respectively, the ligand system di-n-pentylsilanediylbis(2-methyl-4-(4'-tert-butylphenyl)indene) and the corresponding metallocene di-n-pentylsilanediylbis(2-methyl-4-(4'-tert-butylphenyl)-indenyl)zirconium dichloride was synthesized. The desired product is obtained in a rac:meso ratio>17:1.

Example 3

Preparation of Diethylsilanediylbis(2-methyl-4-(4'-tert-butylphenyl)indene)

48.0 g (183 mmoles) of 2-methyl-4-(4'-tert-butylphenyl)-1-indene are introduced into 822 mL of toluene and 48 mL of THF, and 77 mL of an n-butyllithium solution (2.5 M in toluene) are added without interruption at room temperature. After this addition is complete, the mixture is heated to 80° C. and stirred at this temperature for one hour. It is allowed to cool to 40° C., and then 13.7 mL (91.5 mmoles) of diethyldichlorosilane are slowly added dropwise. After this addition, the reaction solution is stirred for three hours at 60° C. and then overnight at room temperature. 400 mL of water are added and the phases that form are separated. The organic phase is washed with 200 mL of water, and the aqueous phase is extracted three times with a total of 300 mL of toluene. The combined organic phases are dried over magnesium sulfate. After separation of the magnesium sulfate, the solvent is removed, and the residue is stirred with 300 mL of pentane. The colorless precipitate is separated by filtration, washed with 100 mL of pentane, and dried in a vacuum. The desired product diethylsilanediylbis(2-methyl-4-(4'-tert-butylphenyl)indene) is isolated in a yield of 27.3 g (49%) (purity 99%).

$^1$H-NMR (400 MHz, CDCl$_3$): 7.45-7.09 (m, 14H, arom-H), 6.77 (s, br, 2H, olefin-H indene), 3.63, 3.53 (each s, each 1H, SiC-H), 2.07 (s, 6H, CH$_3$), 1.37 (s, 18H, tert-butyl), 0.78-0.61 (m, 10H, aliph-H).

Example 4

Preparation of Diethylsilanediylbis(2-methyl-4-(4'-tert-butylphenyl)-indenyl)zirconium dichloride 13.3 g (21.8 mmoles) of diethylsilanediylbis(2-methyl-4-(4'-tert-butylphenyl)indene) are introduced into 135 mL of diethyl ether. 17.5 mL of an n-butyllithium solution (2.5 M in toluene) are added at room temperature, and the suspension is stirred overnight at this temperature. The reaction solution is cooled to 0° C., and then 5.1 g (21.8 mmoles) of zirconium tetrachloride are added in portions. After this addition, the reaction solution is allowed to warm to room temperature and is then stirred for two hours at this temperature. The precipitate that forms is filtered through a G3 fritted glass filter and the residue is washed once with 38 mL of diethyl ether. The residue is then dried in a vacuum, and the desired product is obtained in a yield of 8.6 g (51%) with a rac:meso ratio of 5:1.

$^1$H-NMR (400 MHz, CDCl$_3$): 7.60-6.99 (m, 16H, arom-H), 2.23 (s, 6H, CH$_3$), 1.95-1.78 (m, 4H, aliph-H), 1.45(t, 6H, CH$_3$), 1.31 (s, 18H, tert-butyl).

Example 5

Preparation of (2-Isopropyl-4-(4'-tert-butylphenyl)-1-indenyl)di-n-hexylchlorosilane 20 g (68.9 mmoles) of 2-isopropyl-4-(4'-tert-butylphenyl)-1-indene are introduced into 145 mL of toluene and 4.5 mL of dimethoxyethane, and 27.6 mL of an n-butyllithium solution (2.5 M in toluene) are added without interruption at room temperature. After this addition is complete, the mixture is heated to 80° C. and stirred for one hour at this temperature. It is then allowed to cool to room temperature. The resulting reaction solution is slowly added dropwise to a solution of 57.8 mL (206 mmoles) of di-n-hexyldichlorosilane in 236 mL of tetrahydrofuran, which has been cooled to −40° C. The solution is allowed to warm to room temperature and is then stirred overnight. The solvent is removed in an oil-pump vacuum, and the remaining residue is dissolved in 91 mL of toluene. The insoluble lithium chloride is filtered through a G4 fritted glass filter and washed twice with 9 mL of toluene per washing. The solvent is then removed in a rotary evaporator, and the excess di-n-hexyldichlorosilane is removed by vacuum distillation. The desired product is isolated in a yield of 34.6 g (96%) (70%/o according to GC).

$^1$H-NMR (400 MHz, CDCl$_3$): 7.29-7.05 (m, 7H, arom-H), 6.73 (s, 1H, olefin-H indene), 3.75 (s, 1H, SiCH), 2.86-2.77 (m, 1H, isopropyl-H), 1.29 (s, 9H, tert-butyl), 1.29, 1.24 (each d, each 3H, isopropyl-CH$_3$), 0.72-0.63 (m, 6H, aliph-H), 0.42-0.06 (m, 20H, aliph-H).

Example 6

Preparation of Di-n-hexylsilanediyl(2-isopropyl-4-(4'-tert-butylphenyl)-1-indenyl)(2-methyl-4-(4'-tert-butylphenyl)-1-indenyl)zirconium dichloride 16.4 g (62.5 mmoles) of 2-methyl-4-(4'-tert-butylphenyl)-1-indene are introduced into 197 mL of toluene and 9.2 mL of tetrahydrofuran, and 26.3 mL of an n-butyllithium solution (2.5 M in toluene) are added without interruption at room temperature. After this addition is complete, the mixture is heated to 80° C. and stirred for one hour at this temperature. It is then allowed to cool. A solution of 32.7 g (62.5 mmoles) of (2-isopropyl-4-(4'-tert-butylphenyl)-1-indenyl)di-n-hexylchlorosilane in 68 mL of toluene is added to this reaction solution by drops within 10 minutes. The suspension is then stirred for three hours at 60° C. The reaction solution is cooled to room temperature, and then 50 mL of an n-butyllithium solution (2.5 M in toluene) are added without interruption. After this addition is complete, the mixture is heated to 80° C. and stirred for two hours at this temperature. It is allowed to cool to room temperature, and then 16.9 g (72.5 mmoles) of zirconium tetrachloride are added in portions. The resulting mixture is stirred for two hours at 45° C. and for one hour at room temperature. The precipitate that forms is separated by filtration through a G3 fritted glass filter and then carefully washed with 20-mL portions of tetrahydrofuran. The residue is dried in an oil-pump vacuum, and the product is obtained in a yield of 32.9 g (58%) and with a rac:meso ratio>15:1.

$^1$H-NMR (400 MHz, CDCl$_3$): 7.71-7.01 (m, 16H, arom-H), 3.18-3.11 (m, 1H, isopropyl-H), 2.23 (s, 3H, CH$_3$), 1.86-1.33 (m, 20H, aliph-H), 1.30 (s, 18H, tert-butyl), 1.12 (d, 3H, isopropyl-CH$_3$), 1.05 (d, 3H, isopropyl-CH$_3$), 0.89 (t, 6H, CH$_3$).

Example 7

Preparation of (2-Isopropyl-4-(4'-tert-butylphenyl)-1-indenyl)diethylchlorosilane 16.4 g (56.5 mmoles) of 2-isopropyl-4-(4'-tert-butylphenyl)-1-indene are introduced into 120 mL of toluene and 4.0 mL of dimethoxyethane, and 22.6 mL of an n-butyllithium solution (2.5 M in toluene) are added without interruption at room temperature. After this addition is complete, the mixture is heated to 80° C. and stirred for one hour at this temperature. It is then allowed to cool to room temperature. The resulting reaction solution is slowly added dropwise to a solution of 25.3 mL (169 mmoles) of diethyldichlorosilane in 190 mL of tetrahydrofuran, which has been cooled to −40° C. The solution is allowed to warm to room temperature and is then stirred overnight. The solvent is removed in an oil-pump vacuum and the residue is dissolved in 75 mL of toluene. The insoluble lithium chloride is filtered through a G4 fritted glass filter and washed twice with 7 mL of toluene per washing. The solvent is then removed in a rotary evaporator, and an oil is obtained. The desired product is dried in an oil-pump vacuum at 50° C. and isolated in a yield of 21.8 g (94%) (72% according to GC).

$^1$H-NMR (400 MHz, CDCl$_3$): 7.16-7.01 (m, 7H, arom-H), 6.71 (s, 1H, olefin-H indene), 3.71 (s, 1H, SiCH), 2.89-2.81 (m, 1H, isopropyl-H), 1.27 (s, 9H, tert-butyl), 1.25, 1.22 (each d, each 3H, isopropyl-CH$_3$), 0.72-0.63 (m, 6H, aliph-H), 0.21-0.12 (m, 4H, aliph-H).

Example 8

Preparation of Diethylsilanediyl(2-isopropyl-4-(4'-tert-butylphenyl)-1-indenyl)(2-methyl-4-(4'-tert-butylphenyl)-1-indenyl)zirconium dichloride 17.6 g (67.0 mmoles) of 2-methyl-4-(4'-tert-butylphenyl)-1-indene are introduced into 210 mL of toluene and 10.0 mL of tetrahydrofuran, and 28.1 mL of an n-butyllithium solution (2.5 M in toluene) are added without interruption at room temperature. After this addition is complete, the mixture is heated to 80° C. and stirred for one hour at this temperature. It is then allowed to cool. A solution of 27.5 g (67.0 mmoles) of (2-isopropyl-4-(4'-tert-butylphenyl)-1-indenyl)diethylchlorosilane in 72 mL of toluene is added to this reaction solution dropwise within 10 minutes. The suspension is then stirred for three hours at 60° C. The reaction solution is cooled to room temperature, then 54 mL of an n-butyllithium solution (2.5 M in toluene) are added without interruption. After this addition is complete, the mixture is heated to 80° C. and stirred for two hours at this temperature. It is allowed to cool to room temperature, then 18.1 g (77.6 mmoles) of zirconium tetrachloride are added in portions. It is stirred for two hours at 45° C. and for one hour at room temperature. The precipitate that forms is separated by filtration through a G3 fritted glass filter and then carefully washed with 20-mL portions of tetrahydrofuran. The residue is dried in an oil-pump vacuum, and the product is obtained in a yield of 28.8 g (54%) and with a rac:meso ratio of 5:1.

$^1$H-NMR (400 MHz, CDCl$_3$): 7.63-6.90 (m, 16H, arom-H), 3.20-3.12 (m, 1H, isopropyl-H), 2.26 (s, 3H, CH$_3$), 1.89-1.68 (m, 4H, aliph-H), 1.47 (t, 6H, CH$_3$), 1.33 (s, 18H, tert-butyl), 1.09 (d, 3H, isopropyl-CH$_3$), 1.03 (d, 3H, isopropyl-CH$_3$).

Example 9

Preparation of Di-n-hexylbis(2-methyl-4,5-benzoindenyl)silane

A solution of 5.4 g (30.0 mmoles) of the isomeric mixture of 2-methyl-4,5-benzoindene and 2-methyl-6,7-benzoindene in 50 mL of tetrahydrofuran is treated with 12 mL of an n-butyllithium solution (2.5 M in hexane) and heated under reflux for one hour. The resulting red solution is then added dropwise at room temperature to a solution of 4.0 g (15.0 mmoles) of di-n-hexyldichlorosilane in 10 mL of THF, and the resulting solution is heated under reflux for 5-6 hours. The reaction solution is then cooled to room temperature and poured into ice water. The aqueous phase is repeatedly extracted with 50 mL of diethyl ether. After the organic phase has been dried with magnesium sulfate, the solvent is removed and the residue is purified by column chromatography. The desired product is isolated in a yield of 4.8 g (58%).

$^1$H-NMR (400 MHz, CDCl$_3$): 7.93-7.18 (m, 12H, arom-H), 6.33 (s, br, 2H, olefin-H indene), 3.50, 3.42 (each s, each 1H, SiC-H), 1.98, 1.94 (each s, each 3H, CH$_3$), 1.25-1.04 (m, 16H, aliph-H), 0.72-0.65 (m, 6H, CH$_3$), 0.63-0.48 (m, 4H, aliph-H).

Example 10

Preparation of Di-n-hexylsilanediylbis(2-methyl-4, 5-benzoindenyl)zirconium dichloride A solution of 2.0 g (3.6 mmoles) of di-n-hexylbis(2-methyl-4,5-benzo-indenyl)silane in 20 mL of tetrahydrofuran is treated with 2.9 mL of an n-butyllithium solution (2.5 M in hexane) and stirred for 16 hours at room temperature. The reaction solution is cooled to 0° C. and 606 mg (3.6 mmoles) of zirconium tetrachloride are added in portions. After this addition, the solution is warmed to room temperature and stirred for two hours at this temperature. The precipitate that forms is filtered through a G3 fritted glass filter and the residue is washed once with 5 mL of diethyl ether. The residue is then dried in a vacuum, and the desired product is obtained in a yield of 1.34 g (52%) with a rac:meso ratio>15:1.

$^1$H-NMR (400 MHz, CDCl$_3$): 7.58-7.01 (m, 14H, arom-H), 2.24 (s, 6H, CH$_3$), 1.85-1.30 (m, 20H, aliph-H), 0.88(t, 6H, CH$_3$).

Example 11

Preparation of Di-n-hexylbis(2-methyl-indenyl)silane 9.2 g (70.7 mmoles) of 2-methylindene are introduced into 200 mL of toluene and 15 mL of THF, and 28.3 mL of n-butyllithium (2.5 M in toluene) are added without interruption at room temperature. After this addition is complete, the mixture is heated to 80° C. and stirred at this temperature for one hour. It is allowed to cool to 40° C., then 9.5 g (35.4 mmoles) of di-n-hexyldichlorosilane are slowly added dropwise. After this addition, the reaction solution is stirred for three hours at 60° C. and then overnight at room temperature. 80 mL of water are added and the phases that form are separated. The organic phase is washed with 100 mL of water, and the aqueous phase is extracted three times with a total of 100 mL of toluene. The combined organic phases are dried over magnesium sulfate. After separation of the magnesium sulfate, the solvent is removed and the residue is purified by column chromatography. The desired product is isolated in a yield of 13.3 g (82%) (purity 99%).

$^1$H-NMR (400 MHz, CDCl$_3$): 7.53-7.08 (m, 8H, arom-H), 6.38 (s, br, 2H, olefin-H indene), 3.53, 3.47 (each s, each 1H, SiC-H), 2.07, 2.04 (each s, each 3H, CH$_3$), 1.15-0.89 (m, 16H, aliph-H), 0.67-0.55 (m, 6H, CH$_3$), 0.51-0.35 (m, 4H, aliph-H).

Example 12

Preparation of Di-n-hexylsilanediylbis(2-methylindenyl)zirconium dichloride A solution of 4.8 g (10.5 mmoles) of di-n-hexylbis(2-methylindenyl)silane in 30 mL of tetrahydrofuran is treated with 8.4 mL of an n-butyllithium solution (2.5 M in hexane) and stirred for 16 hours at room temperature. The reaction solution is cooled to 0° C. and 2.4 g (10.5 mmoles) of zirconium tetrachloride are added in portions. After this addition, the solution is heated to room temperature and stirred for two hours at this temperature. The precipitate that forms is filtered through a G3 fritted glass filter, and the residue is washed once with 10 mL of diethyl ether. The residue is then dried in a vacuum, and the desired product is obtained in a yield of 3.1 g (48%) with a rac:meso ratio>20:1.

$^1$H-NMR (400 MHz, CDCl$_3$): 7.46-6.93 (m, 10H, arom-H), 2.23 (s, 6H, CH$_3$), 1.79-1.29 (m, 20H, aliph-H), 0.86(t, 6H, CH$_3$).

Example 13

Preparation of Di-n-hexylbis(2-methyl-4-phenylindenyl)silane 8.0 g (38.8 mmoles) of 2-methyl-4-phenylindene are introduced into 180 mL of toluene and 10 mL of THF, then 15.5 mL of n-butyllithium solution (2.5 M in toluene) are added without interruption at room temperature. After this addition is complete, the mixture is heated to 80° C. and stirred at this temperature for one hour. It is allowed to cool to 40° C., then 5.2 g (19.4 mmoles) of di-n-hexyldichlorosilane are slowly added dropwise. After this addition, the reaction solution is stirred for three hours at 60° C. and then overnight at room temperature. 80 mL of water are added and the phases that form are separated. The organic phase is washed with 80 mL of water, and the aqueous phase is extracted three times with a total of 80 mL of toluene. The combined organic phases are dried over magnesium sulfate. After separation of the magnesium sulfate, the solvent is removed and the residue is purified by column chromatography. The desired product is isolated in a yield of 8.9 g (75%) (purity 97%).

$^1$H-NMR (400 MHz, CDCl$_3$): 7.83-7.10 (m, 16H, arom-H), 6.27 (s, br, 2H, olefin-H indene), 3.55, 3.47 (each s, each 1H, SiC-H), 1.92, 1.90 (each s, each 3H, CH$_3$), 1.30-1.11 (m, 16H, aliph-H), 0.76-0.65 (m, 6H, CH$_3$), 0.65-0.50 (m, 4H, aliph-H).

Example 14

Preparation of Di-n-hexylsilanediylbis(2-methyl-4-phenylindenyl)zirconium dichloride 6.0 g (9.8 mmoles) of di-n-hexylsilanediylbis(2-methyl-4-phenyl)indene are introduced into 80 mL of diethyl ether, and 7.8 mL of an n-butyllithium solution (2.5 M in toluene) are added at room temperature. After this addition is complete, the mixture is stirred overnight at this temperature. It is cooled to 0° C., then 2.3 g (9.8 mmoles) of zirconium tetrachloride are added in portions. 20 mL of diethyl ether are added, then the solution is heated to room temperature and stirred for two hours at this temperature. The precipitate that forms is filtered through a G3 fritted glass filter and washed once with 20 mL of diethyl ether. The residue is then dried in an oil-pump vacuum, and the desired product is obtained in a yield of 3.9 g (52%) with a rac:meso ratio>20:1.

$^1$H-NMR (400 MHz, CDCl$_3$): 7.63-6.93 (m, 18H, arom-H), 2.24 (s, 6H, CH$_3$), 1.90-1.37 (m, 20H, aliph-H), 0.95(t, 6H, CH$_3$).

Example 15

Preparation of Di-n-hexylgermanediylbis(2-methyl-4-(4'-tert-butylphenyl)indene)

12.3 g (46.9 mmoles) of 2-methyl-4-(4'-tert-butylphenyl)-1-indene are introduced into 190 mL of toluene and 11 mL of THF, and 18.8 mL of n-butyllithium (2.5 M in toluene) are added without interruption at room temperature. After this addition is complete, the mixture is heated to 80° C. and stirred at this temperature for one hour. It is allowed to cool to 40° C., then 7.4 g (23.5 mmoles) of di-n-hexyldichlorogermane are slowly added dropwise. After this addition, the reaction solution is stirred for three hours at 60° C. and then overnight at room temperature. 70 mL of water are added and the phases that form are separated. The organic phase is washed with 100 mL of water, and the aqueous phase is extracted three times with a total of 100 mL of toluene. The combined organic phases are dried over magnesium sulfate. After separation of the magnesium sulfate, the solvent is removed, and the residue is purified by column chromatography. The desired product, i.e., Di-n-hexylgermanediylbis(2-methyl-4-(4'-tert-butylphenyl)indene), is isolated in a yield of 11.0 g (61%) (purity 95%).

$^1$H-NMR (400 MHz, CDCl$_3$): 7.50-7.14 (m, 14H, arom-H), 6.75 (s, br, 2H, olefin-H indene), 3.63, 3.50 (each s, each 1H, SiC-H), 2.06, 2.02 (each s, each 3H, CH$_3$), 1.36, 1.33 (each s, each 9H, tert-butyl), 1.23-1.07 (m, 16H, aliph-H), 0.79-0.71 (m, 6H, CH$_3$), 0.65-0.50 (m, 4H, aliph-H).

Example 16

Preparation of Di-n-hexylgermanediylbis(2-methyl-4-(4'-tert-butylphenyl)-indenyl)zirconium dichloride 6.3 g (8.2 mmoles) of di-n-hexylgermanediylbis(2-methyl-4-(4'-tert-butylphenyl)indene are introduced into 80 mL of diethyl ether, and 6.6 mL of n-butyllithium solution (2.5 M in toluene) are added at room temperature. After this addition is complete, the mixture is stirred overnight at this temperature. It is cooled to 0° C., and then 1.9 g (8.2 mmoles) of zirconium tetrachloride are added in portions. After the addition of 20 mL of diethyl ether, the mixture is allowed to warm to room temperature and is then stirred for two hours at this temperature. The precipitate that forms is separated through a G3 fritted glass filter and washed once with 10 mL of diethyl ether. The residue is then dried in an oil-pump vacuum. The desired product is obtained in a yield of 3.6 g (47%) and a rac:meso ratio>20:1.

$^1$H-NMR (400 MHz, CDCl$_3$): 7.74-7.03 (m, 16H, arom-H), 2.23 (s, 6H, CH$_3$), 1.92-1.40 (m, 20H, aliph-H), 1.36(s, 18H, tert-butyl), 0.94 (t, 6H, CH$_3$).

Example 17

Preparation of Cyclohexyl(methyl)silanediylbis(2-methyl-4-(4'-tert-butyl-phenyl)indene)

4.0 g (15.2 mmoles) of 2-methyl-4-(4'-tert-butylphenyl)-1-indene are introduced into 68 mL of toluene and 4 mL of THF, and 6.5 mL of n-butyllithium (2.5 M in toluene) are added without interruption at room temperature. After this addition is complete, the mixture is heated to 80° C. and stirred at this temperature for one hour. It is allowed to cool to 40° C., then 5.8 mL (20.7 mmoles) of cyclohexyl(methyl) dichlorosilane are slowly added dropwise. After this addition, the reaction solution is stirred for three hours at 60° C. and then overnight at room temperature. 50 mL of water are added and the phases that form are separated. The organic phase is washed with 25 mL of water, and the aqueous phase is extracted twice with a total of 20 mL of toluene. The combined organic phases are dried over magnesium sulfate. After separation of the magnesium sulfate, the solvent is removed, and the residue is purified by column chromatography. The desired product, i.e., cyclohexyl(methyl)silanediylbis(2-methyl-4-(4'-tert-butylphenyl)indene) is isolated in a yield of 2.35 g (48%) (purity 97%).

$^1$H-NMR (400 MHz, CDCl$_3$): 7.45-7.02 (m, 14H, arom-H), 6.76 (s, 1H, olefin-H indene), 3.61 (s, 1H, SiC-H), 3.50 (s, 2H, benzyl-H), 2.21, 2.06 (each s, each 3H, CH$_3$), 1.81-1.23 (m, 11H, aliph-H), 1.38, 1.37 (each s, each 9H, tert-butyl), 0.18 (s, 3H, Me).

Example 18

Preparation of Cyclohexyl(methyl)silanediylbis(2-methyl-4-(4'-tert-butyl-phenyl)indenyl)zirconium dichloride 7.0 g (10.8 mmoles) of cyclohexyl(methyl)silanediylbis (2-methyl-4-(4'-tert-butylphenyl)indene) are introduced into 70 mL of diethyl ether, and 8.6 mL of an n-butyllithium solution (2.5 M in toluene) are added at room temperature. After this addition is complete, the mixture is stirred overnight at this temperature. It is cooled to 0° C., and then 2.51 g (10.8 mmoles) of zirconium tetrachloride are added in portions. The solution is stirred for two hours at room temperature. The precipitate that forms is separated by filtration through a G3 fritted glass filter and washed twice with 6 mL of diethyl ether. The residue is then dried in an oil-pump vacuum, and the desired product is obtained in a yield of 4.66 g (53%) with a rac:meso ratio>20:1.

$^1$H-NMR (400 MHz, CDCl$_3$): 7.40-6.97 (m, 16H, arom-H), 2.22 (s, 6H, CH$_3$), 2.19-1.46 (m, 11H, aliph-H), 1.32(s, 18H, tert-butyl), 1.27 (s, 3H, CH$_3$).

Example 19

Preparation of Dicyclopentylsilanediylbis(2-methyl-4-(4'-tert-butylphenyl)-indene)

This synthesis is analogous to Example 17.

Example 20

Preparation of Dicyclopentylsilanediylbis(2-methyl-4-(4'-tert-butylphenyl)-indenyl)zirconium dichloride This synthesis is analogous to Example 18.

Example 21

Preparation of n-Butyl(methyl)silanediylbis(2-methyl-4-(4'-tert-butyl-phenyl)indenyl)zirconium dichloride 16 g (60 mmoles) of 2-methyl-4-(4'-tert-butylphenyl)-1-indene are introduced into 260 mL of toluene and 16 mL of tetrahydrofuran, and 25.9 mL of an n-butyllithium solution (2.5 M in toluene) are added without interruption at room temperature. After this addition is complete, the mixture is heated to 80° C. and stirred for one hour at this temperature. It is allowed to cool to 40° C., then 5.1 g (30 mmoles) of n-butyl(methyl)dichlorosilane are added dropwise to this reaction solution. The reaction solution is stirred for three hours at 60° C. It is cooled to room temperature, and then 24.2 mL of an n-butyllithium solution (2.5 M in toluene) are added dropwise. After this addition is complete, the solution is heated to 80° C. and stirred for one hour at this temperature. It is allowed to cool to room temperature, then 7.0 g (30 mmoles) of zirconium tetrachloride are added in portions. The solution is stirred for two hours at 45° C. and the precipitate that forms is separated by filtration through a G3 fritted glass filter and then carefully washed with 80 mL portions of tetrahydrofuran. The residue is dried in an oil-pump vacuum, and the product is obtained in a yield of 12.4 g (53%) and with a rac:meso ratio of >6:1.

$^1$H-NMR (400 MHz, CDCl$_3$): 7.68-6.88 (m, 16H, arom-H), 2.24 (s, 6H, CH$_3$), 1.82-0.88 (m, 30H, aliph-H).

Example 22

Preparation of n-Hexyl(methyl)silanediylbis(2-methyl-4-(4'-tert-butyl-phenyl)indenyl)zirconium dichloride 30 g (114 mmoles) of 2-methyl-4-(4'-tert-butylphenyl)-1-indene are introduced into 508 mL of toluene and 30 mL of tetrahydrofuran, and 45.8 mL of an n-butyllithium solution (2.5 M in toluene) are added without interruption at room temperature. After this addition is complete, the mixture is heated to 80° C. and stirred for one hour at this temperature. It is allowed to cool to 40° C., then 11.4 g (57 mmoles) of n-hexyl(methyl)dichlorosilane are added dropwise to this reaction solution. The reaction solution is stirred for three hours at 60° C. It is cooled to room temperature, and then 46 mL of an n-butyllithium solution (2.5 M in toluene) are added dropwise. After this addition is complete, the solution is heated to 80° C. and stirred for one hour at this temperature. It is allowed to cool to room temperature, then 13.3 g (57 mmoles) of zirconium tetrachloride are added in portions. The solution is stirred for two hours at 45° C. and the precipitate that forms is separated by filtration through a G3 fritted glass filter and then carefully washed with 140 mL portions of tetrahydrofuran. The residue is dried in an oil-pump vacuum, and the product is obtained in a yield of 22.7 g (49%) and with a rac:meso ratio of >15:1.

$^1$H-NMR (400 MHz, CDCl$_3$): 7.70-6.81 (m, 16H, arom-H), 2.23 (s, 6H, —CH$_3$), 1.89-0.79 (m, 34H, aliph.-H).

Comparison Example 23

Preparation of Dimethylsilanediylbis(2-methyl-4-(4'-tert-butyl-phenyl)indenyl)zirconium dichloride 143 g (0.54 moles) of 2-methyl-4-(4'-tert-butylphenyl)-1-indene are introduced into 2.4 L of toluene and 143 mL of tetrahydrofuran, and 234 mL of an n-butyllithium solution (2.5 M in toluene) are added without interruption at room temperature. After this addition is complete, the mixture is heated to 80° C. and stirred for one hour at this temperature. It is allowed to cool to 40° C., then 33.6 g (0.26 moles) of dimethyldichlorosilane are added dropwise to this reaction solution. The reaction solution is stirred for three hours at 60° C. It is cooled to room temperature, and then 218 mL of an n-butyllithium solution (2.5 M in toluene) are added dropwise. After this addition is complete, the solution is heated to 80° C. and stirred for one hour at this temperature. It is allowed to cool to room temperature, then 71.1 g (0.305 moles) of zirconium tetrachloride are added in portions. The solution is stirred for two hours at 45° C. and the precipitate that forms is separated by filtration through a G3 fritted glass filter and then carefully washed with 700-mL portions of tetrahydrofuran. The residue is dried in an oil-pump vacuum, and the product is obtained in a yield of 155 g (80%) and with a rac:meso ratio of 1:1. The isomers must be separated in an additional step to obtain selective catalysts for propylene polymerization.

$^1$H-NMR (400 MHz, CDCl$_3$): 7.63-6.85 (m, 16H, arom-H), 2.44 (s, 3H, meso-CH$_3$), 2.24 (s, 3H, rac-CH$_3$), 1.46(s, 1.5H, meso-SiMe$_2$), 1.33-1.29 (m, 21H, tert-butyl, rac-SiMe$_2$), 1.23 (s, 1.5H, meso-CH$_3$).

Comparison Example 24

Preparation of Ethyl(methyl)silanediylbis(2-methyl-4-(4'-tert-butyl-phenyl)indenyl)zirconium dichloride 32.8 g (125 mmoles) of 2-methyl-4-(4'-tert-butylphenyl)-1-indene are introduced into 500 mL of toluene and 33 mL of tetrahydrofuran, and 53.8 mL of an n-butyllithium solution (2.5 M in toluene) are added without interruption at room temperature. After this addition is complete, the mixture is heated to 80° C. and stirred for one hour at this temperature. It is allowed to cool to 40° C., then 8.9 g (63 mmoles) of ethyl(methyl)dichlorosilane are added dropwise to this reaction solution. The reaction solution is stirred for three hours at 60° C. It is cooled to room temperature, and then 50 mL of an n-butyllithium solution (2.5 M in toluene) are added dropwise. After this addition is complete, the solution is heated to 80° C. and stirred for one hour at this temperature. It is allowed to cool to room temperature, then 14.7 g (63 mmoles) of zirconium tetrachloride are added in portions. The solution is stirred for two hours at 45° C. and the precipitate that forms is separated by filtration through a G3 fritted glass filter and then carefully washed with 160 mL portions of tetrahydrofuran. The residue is dried in an oil-pump vacuum, and the product is obtained in a yield of 36 g (76%) and with a rac:meso ratio of 1.8:1. The isomers must be separated in an additional step to obtain selective catalysts for propylene polymerization.

$^1$H-NMR (400 MHz, CDCl$_3$): 7.66-6.87 (m, 16H, arom-H), 2.23 (s, 6H, CH$_3$), 1.79-1.48 (m, 5H, aliph-H), 1.35-1.29 (m, 21H, aliph-H).

Comparison Example 25

Preparation of Dimethylbis(2-methyl-4,5-benzoindenyl)silane

A solution of 7.0 g (38.8 mmoles) of the isomeric mixture of 2-methyl-4,5-benzoindene and 2-methyl-6,7-benzoindene in 65 mL of tetrahydrofuran is treated with 15.6 mL of an n-butyllithium solution (2.5 M in hexane) and heated under reflux for one hour. The resulting red solution is then added dropwise at room temperature to a solution of 2.51 g (19.4 mmoles) of dimethyldichlorosilane in 10 mL of THF, and the resulting solution is heated under reflux for 5-6 hours. The reaction solution is then cooled to room temperature and poured into ice water. The aqueous phase is repeatedly extracted with 60 mL of diethyl ether. After the organic phase has been dried with magnesium sulfate, the solvent is removed and the residue is purified by column chromatography. The desired product is isolated in a yield of 4.85 g (60%).

$^1$H-NMR (400 MHz, CDCl$_3$): 8.01-7.36 (m, 12H, arom-H), 7.21 (s, br, 2H, olefin-H indene), 3.96 (s, 2H, SiC-H), 2.43 (s, 6H, CH$_3$), -0.22 (s, 6H, SiMe$_2$).

Comparison Example 26

Preparation of Dimethylsilanediylbis(2-methyl-4,5-benzoindenyl)zirconium dichloride A solution of 3.0 g (7.2 mmoles) of dimethylbis(2-methyl-4,5-benzo-indenyl)silane in 30 mL of tetrahydrofuran is treated with 5.8 mL of an n-butyllithium solution (2.5 M in hexane) and stirred for 16 hours at room temperature. The reaction solution is cooled to 0° C. and 1.68 g (7.2 mmoles) of zirconium tetrachloride are added in portions. After this addition, the solution is warmed to room temperature and stirred for two hours at this temperature. The precipitate that forms is filtered through a G3 fritted glass filter and the residue is washed once with 5 mL of diethyl ether. The residue is then dried in a vacuum, and the desired product is obtained in a yield of 2.32 g (56%) with a rac:meso ratio of nearly 1:1. The isomers must be separated in an additional step to obtain selective catalysts for propylene polymerization.

$^1$H-NMR (400 MHz, CDCl$_3$): 7.85-7.10 (m, 14H, arom-H), 2.25 (s, 6H, CH$_3$), 1.30 (s, 6H, CH$_3$).

Comparison Example 27

Preparation of Dimethylbis(2-methyl-indenyl)silane 8.0 g (61.4 mmoles) of 2-methylindene are introduced into 175 mL of toluene and 13 mL of THF, and 24.6 mL of n-butyllithium (2.5 M in toluene) are added without interruption at room temperature. After this addition is complete, the mixture is heated to 80° C. and stirred at this temperature for one hour. It is allowed to cool to 40° C., then 3.96 g (30.7 mmoles) of dimethyldichlorosilane are slowly added dropwise. After this addition, the reaction solution is stirred for three hours at 60° C. and then overnight at room temperature. 70 mL of water are added and the phases that form are separated. The organic phase is washed with 100 mL of water, and the aqueous phase is extracted three times with a total of 100 mL of toluene. The combined organic phases are dried over magnesium sulfate. After separation of the magnesium sulfate, the solvent is removed and the residue is purified by column chromatography. The desired product is isolated in a yield of 8.16 g (84%) (purity 99%).

$^1$H-NMR (400 MHz, CDCl$_3$): 7.55-7.12 (m, 8H, arom-H), 6.40 (s, br, 2H, olefin-H indene), 3.51, 3.48 (each s, each 1H, SiC-H), 2.09, 2.04 (each s, each 3H, CH$_3$), 1.71 (s, 6H, CH$_3$), 0.08 (s, 6H, SiMe$_2$).

Comparison Example 28

Preparation of Dimethylsilanediylbis(2-methylindenyl)zirconium dichloride

A solution of 5.0 g (15.8 mmoles) of dimethylbis(2-methylindenyl)silane in 45 mL of tetrahydrofuran is treated with 12.6 mL of an n-butyllithium solution (2.5 M in hexane) and stirred for 16 hours at room temperature. The reaction solution is cooled to 0° C. and 1.84 g (7.9 mmoles) of zirconium tetrachloride are added in portions. After this addition, the solution is heated to room temperature and stirred for two hours at this temperature. The precipitate that forms is filtered through a G3 fritted glass filter, and the residue is washed once with 10 mL of diethyl ether. The residue is then dried in a vacuum, and the desired product is obtained in a yield of 1.89 g (50%) with a rac:meso ratio close to 1:1. The isomers must be separated in an additional step to obtain selective catalysts for propylene polymerization.

$^1$H-NMR (400 MHz, CDCl$_3$): 7.75-6.85 (m, 10H, arom-H), 2.24 (s, 6H, CH$_3$), 1.25 (s, 6H, aliph-H).

Comparison Example 29

Preparation of Dimethylbis(2-methyl-4-phenylindenyl)silane 8.0 g (38.8 mmoles) of 2-methyl-4-phenylindene are introduced into 180 mL of toluene and 10 mL of THF, then 15.5 mL of n-butyllithium solution (2.5 M in toluene) are added without interruption at room temperature. After this addition is complete, the mixture is heated to 80° C. and stirred at this temperature for one hour. It is allowed to cool to 40° C., then 2.5 g (19.4 mmoles) of dimethyldichlorosilane are slowly added dropwise. After this addition, the reaction solution is stirred for three hours at 60° C. and then overnight at room temperature. 80 mL of water are added and the phases that form are separated. The organic phase is washed with 80 mL of water, and the aqueous phase is extracted three times with a total of 80 mL of toluene. The combined organic phases are dried over magnesium sulfate. After separation of the magnesium sulfate, the solvent is removed and the residue is purified by column chromatography. The desired product is isolated in a yield of 7.27 g (80%) (purity 97%).

$^1$H-NMR (400 MHz, CDCl$_3$): 7.73-7.12 (m, 16H, arom-H), 6.75 (s, br, 2H, olefin-H indene), 3.76 (s, 2H, SiC-H), 2.17 (s, 6H, CH$_3$), -0.20 (m, 6H, SiMe$_2$).

Comparison Example 30

Preparation of Dimethylsilanediylbis(2-methyl-4-phenylindenyl)zirconium dichloride 5.0 g (10.7 mmoles) of dimethylsilanediylbis(2-methyl-4-phenyl)indene are introduced into 80 mL of diethyl ether, and 8.6 mL of an n-butyllithium solution (2.5 M in toluene) are added at room temperature. After this addition is complete, the mixture is stirred overnight at this temperature. It is cooled to 0° C., then 2.49 g (10.7 mmoles) of zirconium tetrachloride are added in portions. 20 mL of diethyl ether are added, then the solution is heated to room temperature and stirred for two hours at this temperature. The precipitate that forms is filtered through a G3 fritted glass filter and washed once with 20 mL of diethyl ether. The residue is then dried in an oil-pump vacuum, and the desired product is obtained in a yield of 3.70 g (55%) with a rac:meso ratio close to 1:1. The isomers must be separated in an additional step to obtain selective catalysts for propylene polymerization.

$^1$H-NMR (400 MHz, CDCl$_3$): 7.69-6.93 (m, 18H, arom-H), 2.24 (s, 6H, CH$_3$), 1.30 (s, 6H, SiMe$_2$)

Comparison Example 31

Preparation of (2-Isopropyl-4-(4'-tert-butylphenyl)-1-indenyl)(n-propyl)(methyl)chlorosilane 25 g (86.1 mmoles) of 2-isopropyl-4-(4'-tert-butylphenyl)-1-indene are introduced into 180 mL of toluene and 5.6 mL of dimethoxyethane, and 34.4 mL of an n-butyllithium solution (2.5 M in toluene) are added without interruption at room temperature. After this addition is complete, the mixture is heated to 80° C. and stirred for one hour at this temperature. It is then allowed to cool to room temperature. The resulting reaction solution is slowly added dropwise to a solution of 40.5 g (258 mmoles) of n-propyl(methyl)dichlorosilane in 295 mL of tetrahydrofuran, which has been cooled to −40° C. The solution is allowed to warm to room temperature and is then stirred overnight. The solvent is removed in an oil-pump vacuum, and the remaining residue is dissolved in 113 mL of toluene. The insoluble lithium chloride is filtered through a G4 fritted glass filter and washed twice with 15 mL of toluene per washing. The solvent is then removed in a rotary evaporator, and the excess dihexyldichlorosilane is removed by vacuum distillation. The desired product is isolated in a yield of 32.6 g (92%) (70% according to GC).

H-NMR (400 MHz, $CDCl_3$): 7.35-7.13 (m, 7H, arom-H), 6.73 (s, 1H, olefin-H indene), 3.69 (s, 1H, SiCH), 2.90-2.81 (m, 1H, isopropyl-H), 1.33-0.42 (m, 25H, aliph-H).

Comparison Example 32

Preparation of n-Propyl(methyl)silanediyl(2-isopropyl-4-(4'-tert-butylphenyl)-1-indenyl)(2-methyl-4-(4'-tert-butylphenyl)-1-indenyl)zirconium dichloride 15.0 g (57.2 mmoles) of 2-methyl-4-(4'-tert-butylphenyl)-1-indene are introduced into 180 mL of toluene and 8.4 mL of tetrahydrofuran, and 23.2 mL of an n-butyllithium solution (2.5 M in toluene) are added without interruption at room temperature. After this addition is complete, the mixture is heated to 80° C. and stirred for one hour at this temperature. It is then allowed to cool. A solution of 23.5 g (57.2 mmoles) of (2-isopropyl-4-(4'-tert-butylphenyl)-1-indenyl)-n-propyl(methyl)chlorosilane in 62 mL of toluene is added to this reaction solution by drops within 10 minutes. The suspension is then stirred for three hours at 60° C. The reaction solution is cooled to room temperature, and then 45.8 mL of an n-butyllithium solution (2.5 M in toluene) are added without interruption. After this addition is complete, the mixture is heated to 80° C. and stirred for two hours at this temperature. It is allowed to cool to room temperature, and then 13.3 g (57.2 mmoles) of zirconium tetrachloride are added in portions. The resulting mixture is stirred for two hours at 45° C. and for one hour at room temperature. The precipitate that forms is separated by filtration through a G3 fritted glass filter and then carefully washed with 20-mL portions of tetrahydrofuran. The residue is dried in an oil-pump vacuum, and the product is obtained in a yield of 27.4 g (60%, purity 91% according to NMR) and with a rac:meso ratio of 3:1. The isomers must be separated in an additional step to obtain selective catalysts for propylene polymerization.

$^1$H-NMR (400 MHz, $CDCl_3$): 7.75-6.99 (m, 16H, arom-H), 3.20-3.10 (m, 1H, isopropyl-H), 2.25 (s, 3H, $CH_3$), 1.64-0.91 (m, 34H, aliph-H).

Example 33

Preparation of Catalyst System 1 a) Preparation of Bis(pentafluorophenylboroxy)methylalane 1 mL of trimethylaluminium solution (2.1 M in Exxol) is introduced into 13 mL of toluene at room temperature, 1.45 g (4.0 mmoles) of bis(pentafluorophenyl)borinic acid are added, and the solution is stirred for 90 minutes.

b) Preparation of Supported Bis(pentafluorophenylboroxy)methylalane 1.5 g of $SiO_2$ (Grace XPO 2107) are suspended in 15 mL of toluene. 220 μL (1.5 mmoles) of N,N-dimethylbenzylamine are added, and the suspension is stirred slowly for one hour at room temperature. The solution prepared in (a) is added dropwise to this suspension at room temperature, and the resulting suspension is stirred for one hour at room temperature. The suspension is filtered through a G4 fritted glass filter, and the residue is dried in a vacuum. 2.1 g of the support material are obtained.

c) Preparation of Catalyst System 1

0.064 mmole of zirconocene dichloride (see Examples 2, 4, 6, 8, 10, 12, 14, 16, 18, 20, and Comparison Example 23) are dissolved in 18 mL of toluene (due to the poor solubility of the metallocene of Comparison Example 23, in this case 180 ml toluene have been used to solve the metallocene), and 320 μL of a trimethylaluminium solution (2 M in toluene) are added dropwise at room temperature. The suspension is stirred for one hour at 50° C. This solution is added dropwise to a suspension of 2 g of the support material prepared in (b) in 10 mL of toluene. The suspension is stirred for one hour at room temperature; and the solvent is removed in a vacuum. About 2.0-2.3 g of a free-flowing powder are obtained.

Example 34

Preparation of Catalyst System 2

0.032 mmole of zirconocene dichloride (see Examples 2, 4, 6, 8, 10, 12, 14, 16, 18, 20, and Comparison Example 23) are dissolved in 10 mL of toluene (50 ml toluene in the case of Comparison Example 23), and 1.5 mL of a methylaluminoxane solution (30% in toluene) are added. The solution is stirred for one hour at room temperature. The solution is then added to a suspension of 1.5 g of $SiO_2$ (Grace XPO 2107) in 10 mL of toluene, and the suspension is stirred for 15 minutes at room temperature. The solvent is removed in a vacuum, and about 1.8-2.1 g of a free-flowing powder are obtained.

TABLE 1

Metallocene content of selected catalysts produced according to examples 33 and 34

| Metallocene used from example | Catalyst system produced according to example | Metallocene content of the catalyst [mg metallocene/g catalyst] |
| --- | --- | --- |
| 2 | 34 | 15.6 |
| 4 | 34 | 13.7 |
| 6 | 34 | 16.1 |
| 8 | 33 | 25.5 |
| 10 | 34 | 12.7 |
| 12 | 33 | 19.7 |
| 14 | 33 | 24.6 |
| 16 | 34 | 16.4 |
| 18 | 33 | 25.8 |
| 20 | 34 | 15.1 |
| 21 | 34 | 12.5 |
| 22 | 33 | 25.9 |
| Comp. Ex. 23 | 34 | 13.2 |
| Comp. Ex. 23 | 33 | 23.7 |
| Comp. Ex. 24 | 34 | 12.7 |
| Comp. Ex. 24 | 33 | 23.0 |
| Comp. Ex. 26 | 34 | 10.2 |
| Comp. Ex. 26 | 33 | 17.6 |
| Comp. Ex. 28 | 34 | 8.5 |
| Comp. Ex. 28 | 33 | 15.2 |
| Comp. Ex. 30 | 34 | 10.6 |
| Comp. Ex. 30 | 33 | 18.3 |
| Comp. Ex. 32 | 34 | 13.4 |
| Comp. Ex. 32 | 33 | 24.3 |

Polymerization Procedure A

Polymerization Examples P 1-P 10, Comparison Examples P 11 and P 12

A dry 1.8 dm$^3$ autoclave is purged with nitrogen and subsequently with propylene and charged with 1500 cm$^3$ of liquid propylene. 2 cm$^3$ of triisobutylaluminum (20 wt.-% solution in heptane) are added and the mixture is stirred for 15 minutes at 30° C.

For the polymerizations 0.004 mmol of the respective metallocene compounds, supported according to examples 33 or 34, are used. The corresponding amount of the catalyst powder is suspended in 20 cm$^3$ of heptane and is injected with 15 cm$^3$ of heptane. The reaction mixture is heated to the polymerization temperature of 65° C. and polymerization is allowed to proceed at 65° C. 60 minutes. The polymerization is stopped by releasing the liquid monomer and cooling down the reactor. The produced polymer is dried under reduced pressure at 80° C. (the results of the polymerizations are summarized in Table 2 and Table 3).

The polymer produced in examples P 1 to P 10 was a free flowing powder of spherical polymer particles with a narrow particle size distribution and a bulk density>430 g/dm$^3$.

The polymer produced in the comparison examples P 11 and P 12 showed agglomeration of polymer particles, the particle size distribution was much broader than in examples P 1 to P 10 and the bulk density was <400 g/dm$^3$. In addition, the reactor wall and the stirrer was covered by a layer of sticky polymer material.

The heptane extraxtion test (in accordance to ISO 6427: 1992(E)) of the polymer produced in the comparison examples P 11 and P 12 resulted in an intolerable amount of up to 5 wt. % of low molecular weight polypropylene with reduced tacticity (hemiisotactic and atactic polymer). Corresponding tests using the metallocenes and catalyst systems according to the present invention (examples P 1 to P 10) resulted in amounts of less than 0.5 wt. %.

Polymerization Procedure B

Polymerization Examples P 13-P 20, Comparison Example P 21

A dry 1.8 dm$^3$ autoclave is purged with nitrogen and subsequently with propylene and charged with 0.4 Ndm$^3$ hydrogen and 1500 cm$^3$ of liquid propylene. 2 cm$^3$ of triisobutylaluminum (20 wt.-% solution in heptane) are added and the mixture is stirred for 15 minutes at 30° C. For the polymerizations 0.002 mmol of the respective metallocene compounds, supported according to examples 33 or 34, are used. The corresponding amount of the catalyst powder is suspended in 20 cm$^3$ of heptane and is injected with 15 cm$^3$ of heptane. The reaction mixture is heated to the polymerization temperature of 65° C. and polymerization is allowed to proceed at 65° C. for 60 minutes. The polymerization is stopped by releasing the liquid monomer and cooling down the reactor. The produced polymer is dried under reduced pressure at 80° C. (the results of the polymerizations are summarized in Table 4). The examples show the dramatic increase of catalyst productivity by using hydrogen as mole weight regulator together with the catalysts of this invention. In contrast, the increase in productivity of the comparison catalyst was much lower and the reactor wall and the stirrer were again covered by a layer of sticky polymer material.

Polymerization Procedure C

Copolymerization Examples P 22-P 31

A dry and nitrogen purged 5 dm$^3$ autoclave equipped with a helical stirrer is charged with 0.05 Ndm$^3$ hydrogen, 1 cm$^3$ of triisobutylaluminum (25 wt.-% solution in heptane) and 1500 cm$^3$ of liquid propylene. The mixture is stirred for at least 5 minutes (stirrer speed 200 rpm) at 20° C. Then approx. 100 mg of the respective metallocene catalyst (produced according to example 33) are suspended in 5 cm$^3$ of white oil and are injected with 1500 cm$^3$ of liquid propylene. The autoclave is heated up to an internal temperature of 65° C. within 10 minutes. The polymerization reaction is allowed to proceed at 65° C. for 90 minutes. Comonomer addition is started after the injection of the catalyst into the autoclave and continued at a constant rate during the heating up phase and polymerization time. The copolymerization is stopped by releasing the monomers and cooling down the reactor. The produced copolymer is dried under reduced pressure at 80° C. (the added comonomer amounts and the results of the copolymerizations are summarized in Table 5 and Table 6).

TABLE 2

| Polymerization performance | | | |
|---|---|---|---|
| Polymerization example | Catalyst based on metallocene from example | Catalyst produced according to example | Productivity [kg PP/g metallocene × h] |
| P 1 | 2 | 34 | 110.4 |
| P 2 | 4 | 34 | 61.2 |
| P 3 | 6 | 34 | 88.5 |
| P 4 | 8 | 33 | 63.7 |
| P 5 | 10 | 34 | 74.3 |
| P 6 | 12 | 33 | 70.5 |
| P 7 | 14 | 33 | 88.5 |
| P 8 | 16 | 34 | 104.5 |
| P 9 | 18 | 33 | 124.3 |
| P 10 | 20 | 34 | 59.5 |
| Comp. Ex. P 11 | Comp. Ex. 23 | 34 | 43.8 |
| Comp. Ex. P 12 | Comp. Ex. 23 | 33 | 36.0 |

TABLE 3

| Polymer properties | | | | |
|---|---|---|---|---|
| Polymerization Example | Polymer m.p. [° C.] | MW [g/mol] | $M_w/M_n$ | Heptane extractables [wt. %] |
| P 1 | 152 | 688100 | 2.1 | 0.3 |
| P 2 | 151 | 649700 | 2.7 | 0.5 |
| P 3 | 158 | 440500 | 2.3 | 0.2 |
| P 4 | 156 | 425200 | 2.3 | 0.5 |
| P 5 | 145 | 245600 | 2.5 | 0.3 |
| P 6 | 147 | 192700 | 2.1 | 0.3 |
| P 7 | 149 | 861000 | 2.6 | 0.3 |
| P 8 | 153 | 705500 | 2.4 | 0.2 |
| P 9 | 153 | 695400 | 2.2 | 0.3 |
| P 10 | 152 | 692100 | 2.5 | 0.3 |
| Comp. Ex. P 11 | 151 | 690500 | 2.8 | 4.1 |
| Comp. Ex. P 12 | 152 | 687700 | 3.0 | 5.0 |

TABLE 4

Polymerization performance using hydrogen as mole weight regulator

| Polymerization example | Catalyst based on metallocene from example | Catalyst produced according to example | Productivity [kg PP/g metallocene × h] |
|---|---|---|---|
| P 13 | 2 | 34 | 267.4 |
| P 14 | 4 | 34 | 141.2 |
| P 15 | 6 | 34 | 178.3 |
| P 16 | 10 | 34 | 154.7 |
| P 17 | 12 | 33 | 135.2 |
| P 18 | 14 | 33 | 205.4 |
| P 19 | 16 | 34 | 254.4 |
| P 20 | 18 | 33 | 244.2 |
| Comp. Ex. P 21 | Comp. Ex. 23 | 33 | 66.9 |

TABLE 5

Copolymerization conditions

| Polymerization example | Catalyst based on metallocene from example | Comonomer added [g ethylene] |
|---|---|---|
| P 22 | 2 | 25 |
| P 23 | 2 | 50 |
| P 24 | 6 | 30 |
| P 25 | 6 | 90 |
| P 26 | 6 | 300 |
| P 27 | 10 | 25 |
| P 28 | 12 | 25 |
| P 29 | 14 | 25 |
| P 30 | 16 | 25 |
| P 31 | 18 | 25 |

TABLE 6

Copolymer properties

| Polymerization example | Comonomer content [wt.-%] | Polymer m.p. [° C.] | MW [g/mol] |
|---|---|---|---|
| P 22 | 2.8 | 146 | 702000 |
| P 23 | 5.0 | 132 | 604300 |
| P 24 | 1.8 | 151 | 437300 |
| P 25 | 5.2 | 143 | 498500 |
| P 26 | 17.1 | $T_g = -33$ | 527500 |
| P 27 | 2.2 | 141 | n.m. |
| P 28 | 2.0 | 143 | n.m. |
| P 29 | 2.5 | 145 | n.m. |
| P 30 | 2.3 | 147 | 703100 |
| P 31 | 1.9 | 148 | 785500 |

Polymerization Example P 32

Polymerization Example P 26 was repeated. But the addition of the comonomer was not started until 60 minutes after the addition of the catalyst i.e. the amount of ethylene was dosed to the autoclave during the remaining 30 minutes of the polymerisation time. Instead of 300 g, only 180 g of ethylene were added.

The isolated impact copolymer had a MFR of 12 dg/min. The polymer was fractionated and the homopolymer part (78 wt.-%) showed a melting point of 157° C., while the copolymer rubber part (22 wt.-%) showed a $T_g$ of −55° C. and an ethylene content of 43.5 wt.-%. Injection molded parts produced using the polymer, additivated with 0.05 wt. % calcium stearate, 0.1% Irganox 1010 and Irgafos 168 each, showed an excellent stress whitening behavior.

Polymerization Example P 33

Polymerization Example P32 was repeated, but instead of 180 g, only 100 g of ethylene were added.

The isolated impact copolymer had a MFR of 15 dg/min. The polymer was fractionated and the homopolymer part (81 wt.-%) showed a melting point of 157° C., while the copolymer rubber part (19 wt.-%) showed a $T_g$ of −35° C. and an ethylene content of 18.2 wt.-%. Injection molded parts produced using the polymer, additivated with 0.25 wt.-% Millad 3988, 0.05 wt. % calcium stearate, 0.1 wt.-% Irganox 1010 and 0.1 wt.-% Irgafos 168, showed an excellent combination of stiffness, transparency and low temperature impact strength.

Polymerization Example P 34

Polymerization Example P32 was repeated, but instead of 180 g, only 60 g of ethylene were added.

The isolated impact copolymer had a MFR of 20 dg/min. The polymer was fractionated and the homopolymer part (80 wt.-%) showed a melting point of 157° C., while the copolymer rubber part (20 wt.-%) showed a $T_g$ of −9° C. and an ethylene content of 10.2 wt.-%. Injection molded parts produced using the polymer, additivated with 0.2 wt.-% Millad 3988, 0.05 wt. % calcium stearate, 0.1 wt.-% Irganox 1010 and 0.1 wt.-% Irgafos 168, showed an excellent combination of stiffness, transparency and impact strength at 0° C.

Polymerization Example P 35

Polymerization Example P 26 was repeated. But the addition of the comonomer was performed in the following manner: After the addition of the catalyst and during the first 60 minutes of the polymerisation 30 g of ethylene were added and during the remaining 30 minutes of the polymerisation time additional 120 g of ethylene were added.

The isolated random impact copolymer had a MFR of 10 dg/min. The polymer was fractionated and the random copolymer part (85 wt.-%) showed a melting point of 149° C. and an ethylene content of 2.2 wt.-%, while the copolymer rubber part (15 wt.-%) showed a $T_g$ of −45° C. and an ethylene content of 25.5 wt.-%. Injection molded parts produced using the polymer, additivated with 0.22 wt.-% Millad 3988, 0.05 wt. % calcium stearate, 0.1 wt.-% Irganox 1010 and 0.1 wt.-% Irgafos 168, showed an excellent combination of stiffness, transparency and low temperature impact strength at −30° C.

What is claimed is:

1. A composition comprising a mixture of racemic and meso isomers of metallocene compounds having the formula:

$$R^9L^1L^2M^1R^1R^2 \qquad \text{(formula 1a)}$$

where $L^1$ and $L^2$ are identical or different ligands and are each a substituted mononuclear or polynuclear hydrocarbon radical selected from the group consisting of substituted cyclopentadienyl, indenyl, tetrahydroindenyl, azurenyl, fluorenyl, azapentalenyl, thiapentalenyl or oxapentalenyl, which form a sandwich structure with atom $M^1$ therebetween, $R^1$ and $R^2$ are identical or different and are each a hydrogen atom, an alkyl group of from 1 to about 10 carbon atoms, an alkoxy group of from 1 to about 10 carbon atoms, an aryl group of from 6 to about 20 carbon atoms, an aryloxy group of from about 6 to about 10 carbon atoms, an alkenyl group of from 2 to about 10 carbon atoms, an OH group, a halogen atom, or a $NR_2^{32}$ group, where $R^{32}$ is an alkyl group of from 1 to about 10 carbon atoms or an aryl group of from 6 to about 14 carbon atoms, or $R^1$ and $R^2$ form one or more ring system(s), $M^1$ is a metal of group IVb of the Periodic Table of the Elements, $R^9$ is a bridge between the ligands $L^1$ and $L^2$ having one of the structures:

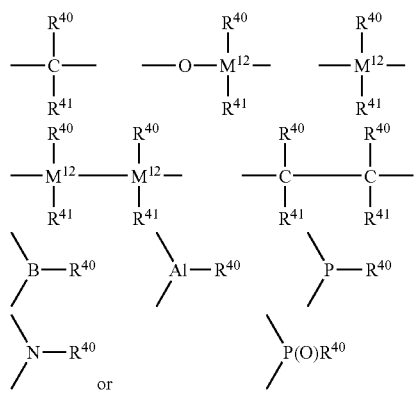

where $R^{40}$ and $R^{41}$, are identical or different, with or without heteroatoms, when $R^{40}$ and $R^{41}$ are identical they are selected from the group consisting of a cyclic or non-cyclic alkyl group having from 2 to about 30 carbon atoms, a fluoroalkyl group of from 2 to about 10 carbon atoms, an alkoxy group of from 2 to about 10 carbon atoms, an aryloxy group of from 6 to about 10 carbon atoms, an alkenyl group of from about 3 to about 10 carbon atoms, an arylalkyl group of from 7 to about 40 carbon atoms, an alkylaryl group of from 7 to about 40 carbon atoms, a substituted or unsubstituted alkylsilyl or arylsilyl group and an arylalkenyl group of from 8 to about 40 carbon atoms, when $R^{40}$ and $R^{41}$ are different one of either $R^{40}$ and $R^{41}$ is selected from the group consisting of a cyclic or non-cyclic alkyl group having from 4 to about 40 carbon atoms, a fluoroalkyl group of from 2 to about 10 carbon atoms, an alkoxy group of from 2 to about 10 carbon atoms, an aryloxy group of from 6 to about 10 carbon atoms, an alkenyl group of from 3 to about 10 carbon atoms, an arylalkyl group of from 7 to about 40 carbon atoms, an alkylaryl group of from 7 to about 40 carbon atoms, a substituted or unsubstituted alkylsilyl or arylsilyl group and an arylalkenyl group of from 8 to about 40 carbon atoms, and the other of $R^{40}$ and $R^{41}$ is selected from the group consisting of a cyclic or non-cyclic alkyl group having from 1 to 40 carbon atoms, a fluoroalkyl group of from 2 to about 10 carbon atoms, an alkoxy group of from 2 to about 10 carbon atoms an aryloxy group of from 6 to about 10 carbon atoms, an alkenyl group of from 3 to about 10 carbon atoms, an arylalkyl group of from 7 to about 40 carbon atoms, an alkylaryl group of from 7 to about 40 carbon atoms, a substituted or unsubstituted alkylsilyl or arylsilyl group and an arylalkenyl group of from 8 to about 40 carbon atoms, $M^{12}$ is silicon, germanium or tin, and wherein the mixture of racemic and meso isomers as synthesized has a weight ratio of racemic to meso isomers of greater than 5:1.

2. The composition of claim 1 wherein $L^1$ is a substituted cyclopentadienyl, indenyl, tetrahydroindenyl, azurenyl, fluorenyl, azapentalenyl, thiapentalenyl or oxapentalenyl, $L^2$ is a substituted indenyl, tetrahydroindenyl, azurenyl, fluorenyl, azapentalenyl, thiapentalenyl or oxapentalenyl, and the bridging unit $R^9$ is $R^{40}R^{41}Si=$, $R^{40}R^{41}Ge=$, $R^{40}R^{41}C=$ or $-(R^{40}R^{41}C-CR^{40}R^{41})-$, where $R^{40}$ and $R^{41}$ are identical or different and are each an alkyl group of from 2 to about 30 carbon atoms, an arylalkyl group of from 7 to about 14 carbon atoms or an alkylaryl group of from 7 to about 14 carbon atoms.

3. The composition of claim 1 wherein $R^{40}$ and $R^{41}$ are different, $R^{40}$ is a $C_4$-$C_{30}$ cyclic or non-cyclic alkyl group and $R^{41}$ is a $C_1$-$C_{30}$ cyclic or non-cyclic alkyl group.

4. The composition of claim 1 wherein $L^1$ and $L^2$ are identical or different and are each a substituted indenyl, azurenyl, fluorenyl, azapentalenyl, thiapentalenyl or oxapentalenyl, and the bridging unit $R^9$ is $R^{40}R^{41}Si=$ or $R^{40}R^{41}Ge=$, where $R^{40}$ and $R^{41}$ are identical or different and are propyl, butyl, pentyl, hexyl, heptyl, octyl, nonyl, decyl, undecyl, dodecyl, cyclopentyl, or cyclohexyl.

5. The composition of claim 4 wherein $R^{40}$ and $R^{41}$ are different, $R^{40}$ is butyl, pentyl, hexyl, heptyl, octyl, nonyl, decyl, undecyl, dodecyl, cyclopentyl, or cyclohexyl, and $R^{41}$ is methyl, ethyl, propyl, butyl, pentyl, hexyl, heptyl, octyl, nonyl, decyl, undecyl, dodecyl, cyclopentyl, or cyclohexyl.

6. The composition of claim 1 wherein the weight ratio of racemic to meso isomers is greater than 10:1.

7. The composition of claim 1 wherein the weight ratio of racemic to meso isomer is greater than 15:1.

8. The composition of claim 1 wherein the weight ratio of racemic to meso isomers is greater than 20:1.

9. The composition of claim 1 wherein the compound has the formula:

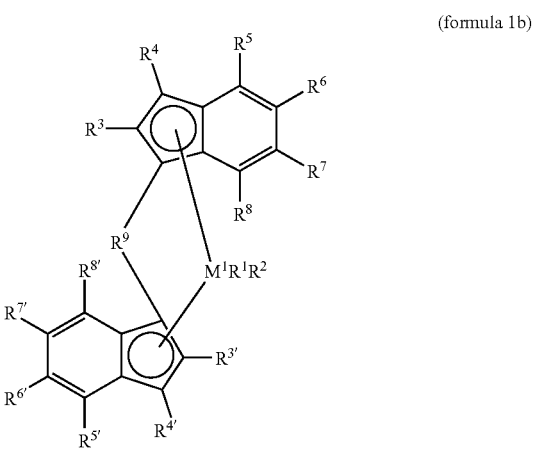

(formula 1b)

where $R^3$, $R^4$, $R^5$, $R^6$, $R^7$, $R^8$ and also $R^{3'}$, $R^{4'}$, $R^{5'}$, $R^{6'}$, $R^{7'}$ and $R^{8'}$ are identical or different and are each a hydrogen atom or a linear, cyclic or branched group, with or without heteroatoms, selected from an alkyl group of from 1 to about 10 carbon atoms, an alkenyl group of from 2 to about 10 carbon atoms, an aryl group of from 6 to about 20 carbon atoms, an arylalkyl group of from 7 to about 40 carbon atoms, an alkylaryl group of from 7 to about 40 carbon atoms, an arylalkenyl group of from 8 to about 40 carbon atoms, or a substituted or unsubstituted alkylsilyl or arylsilyl group, with the proviso that $R^3$ and $R^{3'}$ are not hydrogen, and wherein two adjacent radicals $R^5$, $R^6$ or $R^{5'}$, $R^{6'}$, or $R^6$, $R^7$ or $R^{6'}$, $R^{7'}$, or $R^7$, $R^8$, or $R^{7'}$, $R^{8'}$ can form a hydrocarbon ring system.

10. The composition of claim 9 wherein at least one of $R^3$, $R^4$, $R^5$, $R^6$, $R^7$, $R^8$, $R^{3'}$, $R^{4'}$, $R^{5'}$, $R^{6'}$, $R^{7'}$ and $R^{8'}$ includes a heteroatom selected from the group consisting of Si, B, Al, O, S, N, P, F, Cl and Br.

11. The composition of claim 9 where
$M^1$ is zirconium or hafnium,
$R^1$ and $R^2$ are identical or different and are an alkyl group of from 1 to about 10 carbon atoms, an alkoxy group of from 1 to about 10 carbon atoms, an aryloxy group of from 6 to about 10 carbon atoms, or a halogen atom, or $R^1$ and $R^2$ together form one or more ring system(s),
$R^3$ and $R^{3'}$, are identical or different and are each a linear, cyclic or branched group, with or without a halogen, selected from the group consisting of an alkyl group of from 1 to about 10 carbon atoms and an alkenyl group of from 2 to about 10 carbon atoms,
$R^4$, $R^5$, $R^6$, $R^7$, $R^8$ and also $R^{4'}$, $R^{5'}$, $R^{6'}$, $R^{7'}$ and $R^{8'}$ are identical or different and are each a hydrogen atom, or a substituted or unsubstituted alkylsilyl or arylsilyl group, or a linear, cyclic or branched group, with or without heteroatoms, or an alkyl group of from 1 to about 10 carbon atoms, an aryl group of from 6 to about 10 carbon atoms, or the two adjacent radicals $R^5$, $R^6$ and $R^{5'}$, $R^{6'}$ may form a hydrocarbon ring system,
$R^9$ is $R^{40}R^{41}Si{=}$, $R^{40}R^{41}Ge{=}$, $R^{40}\ R^{41}C{=}$ or $-(R^{40}R^{41}C{-}CR^{40}R^{41})-$, where $R^{40}$ and $R^{41}$ are identical or different and are each an alkyl group of from 2 to about 30 carbon atoms, an arylalkyl group of from 7 to about 14 carbon atoms or an alkylaryl group of from 7 to about 14 carbon atoms.

12. The composition of claim 9 wherein $R^{40}$ and $R^{41}$ are different, $R^{40}$ is an alkyl group of from 4 to about 30 carbon atoms, and $R^{41}$ is a an alkyl group of from 1 to about 30 carbon atoms.

13. The composition of claim 9 wherein
$M^1$ is zirconium,
$R^3$ and $R^2$ are identical or different and are methyl, chlorine or phenolate,
$R^3$ and $R^{3'}$, are identical or different and are each a linear, cyclic or branched group, with or without a halogen, and are selected from the group consisting of an alkyl group of from 1 to about 10 carbon atoms and an alkenyl group of from 2 to about 10 carbon atoms,
$R^4$ and $R^{4'}$ are hydrogen,
$R^5$, $R^6$, $R^7$, $R^8$ and $R^{5'}$, $R^{6'}$, $R^{7'}$, $R^{8'}$ are identical or different and are each a hydrogen atom or a linear, cyclic or branched alkyl group of from 1 to about 10 carbon atoms, or an aryl group of from 6 to about 10 carbon atoms, or the two adjacent radicals $R^5$, $R^6$ and $R^{5'}$, $R^{6'}$ form a hydrocarbon ring system, and
$R^9$ is $R^{40}R^{41}Si{=}$ or $R^{40}R^{41}Ge{=}$, where $R^{40}$ and $R^{41}$ are identical or different and are propyl, butyl, pentyl, hexyl, heptyl, octyl, nonyl, decyl, undecyl, dodecyl, cyclopentyl, or cyclohexyl.

14. The composition of claim 13 wherein $R^{40}$ and $R^{41}$ are different and $R^{40}$ is butyl, pentyl, hexyl, heptyl, octyl, nonyl, decyl, undecyl, dodecyl, cyclopentyl, or cyclohexyl and $R^{41}$ is methyl, ethyl, propyl, butyl, pentyl, hexyl, heptyl, octyl, nonyl, decyl, undecyl, dodecyl, cyclopentyl, or cyclohexyl.

15. The composition of claim 1 wherein the compound has the formula:

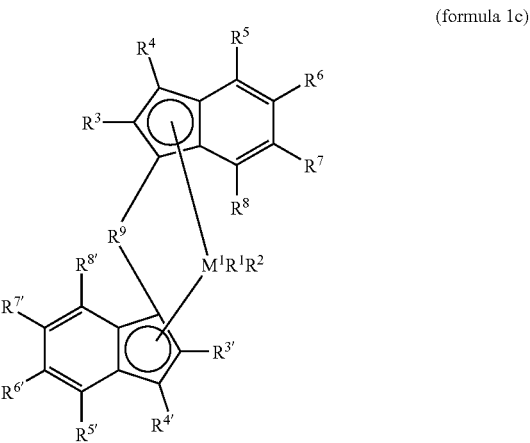

(formula 1c)

where $R^3$, $R^4$, $R^5$, $R^6$, $R^7$, $R^8$ and also $R^{3'}$, $R^{4'}$, $R^{5'}$, $R^{6'}$, $R^{7'}$ and $R^{8'}$ are identical or different and are each a hydrogen atom, or a linear, cyclic or branched hydrocarbon group with or without heteroatoms and selected from an alkyl group of from 1 to about 10 carbon atoms, an alkenyl group of from 2 to about 10 carbon atoms, an aryl group of from 6 to about 20 carbon atoms, an arylalkyl group of from 7 to about 40 carbon atoms, an alkylaryl group of from 7 to about 40 carbon atoms or an arylalkenyl group of from 8 to about 40 carbon atoms, or a substituted or unsubstituted alkylsilyl or arylsilyl group, with the proviso that $R^3$ and $R^{3'}$ are not hydrogen and that $R^5$ and $R^{5'}$ are identical or different and are each a substituted or unsubstituted aryl group of from 6 to 20 carbon atoms.

16. The composition of claim 15 wherein at least one of $R^3$, $R^4$, $R^5$, $R^6$, $R^7$, $R^8$, $R^{3'}$, $R^{4'}$, $R^{5'}$, $R^{6'}$, $R^{7'}$ and $R^{8'}$ includes a heteroatom selected from the group consisting of Si, B, Al, O, S, N, P, F, Cl and Br.

17. The composition of claim 15 wherein $M^1$ is zirconium or hafnium,
$R^1$ and $R^2$ are identical or different and are an alkyl group of from 1 to about 10 carbon atoms, an alkoxy group of from 1 to about 10 carbon atoms, an aryloxy group of from 6 to about 10 carbon atoms or a halogen atom, or $R^1$ and $R^2$ together form one or more ring system(s), and
$R^3$ and $R^{3'}$, are identical or different and are each a linear, cyclic or branched group, with or without a halogen, and selected from the group consisting of an alkyl group of from 1 to about 10 carbon atoms and an alkenyl group of from 2 to about 10 carbon atoms, and
$R^4$, $R^6$, $R^7$, $R^8$ and also $R^{4'}$, $R^{6'}$, $R^{7'}$ and $R^{8'}$ are identical or different and are each a hydrogen atom or a linear, cyclic or branched alkyl group of from 1 to about 10 carbon atoms, with or without a heteroatom,
$R^5$ and $R^{5'}$ are identical or different and are each a substituted aryl group of from 6 to about 20 carbon atoms,
$R^9$ is $R^{40}R^{41}Si{=}$, $R^{40}R^{41}Ge{=}$, $R^{40}R^{41}C{=}$ or $(R^{40}R^{41}C{-}R^{40}R^{41})-$, where $R^{40}$ and $R^{41}$ are identical or different and are each an alkyl group of 2 to about 30 carbon atoms, an arylalkyl group of from 7 to about 14 carbon atoms or an alkylaryl group of from 7 to about 14 carbon atoms.

18. The composition of claim 17 wherein $R^{40}$ and $R^{41}$ are different, $R^{40}$ is a cyclic or non-cyclic alkyl group of from 4 to about 30 carbon atoms and $R^{41}$ is a cyclic or non-cyclic alkyl group of from 1 to about 30 carbon atoms.

19. The composition of claim 15 wherein $M^1$ is zirconium,
$R^1$ and $R^2$ are identical or different and are an alkyl group of from 1 to about 10 carbon atoms, an alkoxy group of from 1 to about 10 carbon atoms, an aryloxy group of from 6 to about 10 carbon atoms or a halogen atom, or $R^1$ and $R^2$ together form one or more ring system(s),
$R^3$ and $R^{3'}$ are identical or different and are each a linear, cyclic or branched methyl, ethyl, propyl, butyl, pentyl or hexyl,
$R^4$ and $R^{4'}$ are both hydrogen,
$R^6$, $R^7$, $R^8$ and also $R^{6'}$, $R^{7'}$ and $R^{8'}$ are identical or different and are each a hydrogen atom or a linear, cyclic or branched alkyl group of from 1 to about 10 carbon atoms, with or without a heteroatom,
$R^5$ and $R^{5'}$ are identical or different and are naphthyl, para-$(C_1$-$C_{10}$-alkyl)phenyl, para -$(C_1$-$C_{10}$-fluoroalkyl)phenyl, meta-$(C_1$-$C_{10}$-alkyl)phenyl, meta-$(C_1$-$C_{10}$-alkyl)phenyl, meta, meta'-$(C_1$-$C_{10}$-alkyl)$_2$phenyl or meta, meta'-$(C_1$-$C_{10}$-fluoroalkyl)$_2$phenyl, and
$R^9$ is $R^{40}R^{41}Si=$ or $R^{40}R^{41}Ge=$.

20. The composition of claim 19 wherein $R^1$ and $R^2$ are identical and are methyl, chlorine, or phenolate.

21. The composition of claim 19 wherein $R^{40}$ and $R^{41}$ are different and $R^{40}$ is butyl, pentyl, hexyl, heptyl, octyl, nonyl, decyl, undecyl, dodecyl, cyclopentyl, or cyclohexyl, and $R^{41}$ is methyl, ethyl, propyl, butyl, pentyl, hexyl, heptyl, octyl, nonyl, decyl, undecyl, dodecyl, cyclopentyl,or cyclohexyl.

22. The composition of claim 1 wherein the compound has the formula:

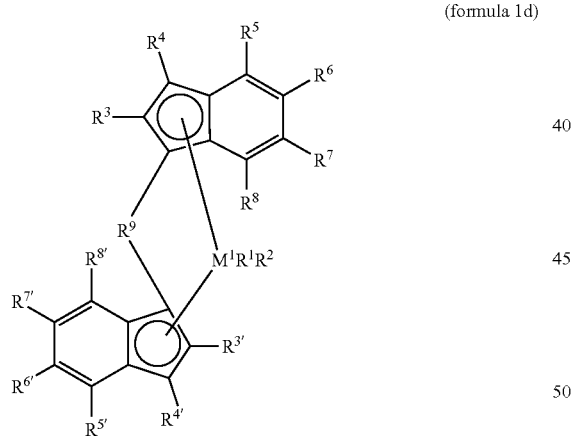

(formula 1d)

where $R^4$, $R^5$, $R^6$, $R^7$, $R^8$ and also $R^{4'}$, $R^{5'}$, $R^{6'}$, $R^{7'}$ and $R^{8'}$ are identical or different and are each a hydrogen atom, a linear, cyclic or branched hydrocarbon group, with or without heteroatoms, and selected from the group consisting of an alkyl group of from 1 to about 10 carbon atoms, an alkenyl group of from 2 to about 10 carbon atoms, an aryl group of from 6 to about 20 carbon atoms, an arylalkyl group of from 7 to about 40 carbon atoms, an alkylaryl group of from 7 to about 40 carbon atoms or an arylalkenyl group of from 8 to about 40 carbon atoms, or a substituted or unsubstituted alkylsilyl or arylsilyl group, with the proviso that $R^5$ and $R^{5'}$ are identical or different and are each a substituted aryl group of from 6 to about 40 carbon atoms,
$R^3$ is a linear hydrocarbon group, with or without a heteroatom, and selected from the group consisting of an alkyl group of from 1 to about 20 carbon atoms, an aryl substituted alkyl group of from 7 to about 40 carbon atoms and an aryl substituted alkenyl group of from 8 to about 40 carbon atoms,
$R^{3'}$ is a hydrocarbon group, cyclic or branched in the α position, with or without a heteroatom, and selected from the group consisting of an alkyl group of from 3 to about 20 carbon atoms, an alkenyl group of from 3 to about 20 carbon atoms, an aryl group of from 6 to about 20 carbon atoms, an arylalkyl group of from 7 to about 40 carbon atoms, an alkylaryl group of from 7 to about 40 carbon atoms and an arylalkenyl group of from 8 to about 40 carbon atoms.

23. The composition of claim 22 wherein $M^1$ is zirconium or hafnium,
$R^1$ and $R^2$ are identical or different and are an alkyl group of from 1 to about 10 carbon atoms, an alkoxy group of from 1 to about 10 carbon atoms, an aryloxy group of from 6 to about 10 carbon atoms or a halogen atom, or $R^1$ and $R^2$ together form one or more ring system(s),
$R^3$ is a linear alkyl group of from 1 to about 10 carbon atoms or an alkenyl group of from 2 to about 10 carbon atoms, with or without a halogen,
$R^{3'}$ is a hydrocarbon group, cyclic or branched in the α position and selected from the group consisting of an alky group of from 3 to about 20 carbon atoms an alkenyl group of from 3 to about 20 carbon atoms, or an arylalkyl group of from 7 to about 20 carbon atoms,
$R^4$, $R^6$, $R^7$, $R^8$ and also $R^{4'}$, $R^{6'}$, $R^{7'}$ and $R^{8'}$ are identical or different and are each a hydrogen atom or a linear, cyclic or branched alkyl group of from 1 to about 10 carbon atoms, with or without a halogen,
$R^5$ and $R^{5'}$ are identical or different and are each a substituted aryl group of from 6 to about 40 carbon atoms, selected from para-$(C_1$-$C_{10}$-alkyl)phenyl,meta-$(C_1$-$C_{10}$-alkyl)phenyl, meta, meta'-$(C_1$-$C_{10}$-alkyl)$_2$phenyl, and
$R^9$ is $R^{40}R^{41}Si=$, $R^{40}R^{41}Ge=$, $R^{40}R^{41}C=$ or $-(R^{40}R^{41}C-CR^{40}R^{41})-$, where $R^{40}$ and $R^{41}$ are identical or different and are each an alkyl group of from 2 to about 30 carbon atoms, an arylalkyl group of from 7 to about 14 carbon atoms or an alkylaryl group of from 7 to about 14 carbon atoms.

24. The composition of claim 22 wherein $R^{40}$ and $R^{41}$ are different, $R^{40}$ is a cyclic or non-cyclic alkyl group of from 4 to about 30 carbon atoms and $R^{41}$ is a cyclic or non-cyclic alkyl group of from 1 to about 30 carbon atoms.

25. The composition of claim 22 where $M^1$ is zirconium, $R^1$ and $R^2$ are identical and are methyl, chlorine, or phenolate,
$R^3$ is methyl, ethyl, n-propyl, n-butyl, n-pentyl or n-hexyl,
$R^{3'}$ is iso-propyl, sec-butyl, cyclobutyl, 1-methyl-butyl, 1-ethyl-butyl, 1-methyl-pentyl, cyclopentyl, cyclohexyl, cyclopent-2-enyl, cyclopent-3-enyl, cyclohex-2-enyl, cyclohex-3-enyl or para-methyl-cyclohexyl,
$R^4$ and also $R^{4'}$ are hydrogen, and
$R^6$, $R^7$, $R^8$ and also $R^{6'}$, $R^{7'}$ and $R^{8'}$ are identical or different and are each a hydrogen atom or a linear, cyclic or branched alkyl group of from 1 to about 10 carbon atoms, with or without a heteroatom, and,
$R^5$ and $R^{5'}$ are identical or different and are p-isopropyl-phenyl, p-tert-butyl-phenyl, p-s-butyl-phenyl, p-cyclohexyl-phenyl, p-trimethylsilyl-phenyl, p-adamantyl-phenyl, p-(trisfluor)trimethyl-phenyl, m,m'-dimethyl-phenyl, and
$R^9$ is $R^{40}R^{41}Si=$ or $R^{40}R^{41}Ge=$.

26. The composition of claim 25 wherein $R^{40}$ and $R^{41}$ are different and $R^{40}$ is butyl, pentyl, hexyl, heptyl, octyl, nonyl, decyl, undecyl, dodecyl, cyclopentyl, or cyclohexyl, and $R^{41}$ is methyl, ethyl, propyl, butyl, pentyl, hexyl, heptyl, octyl, nonyl, decyl, undecyl, dodecyl, cyclopentyl, or cyclohexyl.

27. The composition of claim 1 wherein the synthesized compound is selected from the group consisting of:
- A-(2-isopropyl-4-(p-isopropyl-phenyl)indenyl)(2-methyl-4-(p-isopropyl-phenyl) indenyl)-zirconiumdichloride,
- A-(2-isopropyl-4-(p-tert-butyl-phenyl)indenyl)(2-methyl-4-(p-tert-butyl-phenyl) indenyl)-zirconiumdichloride,
- A-(2-isopropyl-4-(p-tert-butyl-phenyl)indenyl)(2,7-dimethyl-4-(p-tert-butyl-phenyl) indenyl)-zirconiumdichloride,
- A-(2-isopropyl-4-(p-tert-butyl-phenyl)indenyl)(2,5,6,7-tetramethyl-4-(p-tert -butyl-phenyl)indenyl)-zirconiumdichloride,
- A-(2-isopropyl-6-methyl-4-(p-tert-butyl-phenyl)indenyl) (2,6-dimethyl-4-(p-tert -butyl-phenyl)indenyl)-zirconiumdichloride,
- A-(2-isopropyl-4-(p-sec-butyl-phenyl)indenyl)(2-methyl-4-(p-sec-butyl-phenyl) -indenyl)-zirconiumdichloride,
- A-(2-isopropyl-4-(p-cyclohexyl-phenyl)indenyl)(2-methyl-4-(p-cyclohexyl-phenyl) indenyl)-zirconiumdichloride,
- A-(2-isopropyl-4-(p-trimethylsilyl-phenyl)indenyl)(2-methyl-4-(p -trimethylsilyl-phenyl)indenyl)-zirconiumdichloride,
- A-(2-isopropyl-4-(p-adamantyl-phenyl)indenyl)(2-methyl-4-(p-adamantyl-phenyl)indenyl)-zirconiumdichloride,
- A-(2-isopropyl-4-(p-tris(trifluoromethyl)methyl-phenyl)indenyl)(2-methyl-4-(p-tris(trifluoromethyl)methyl-phenyl)indenyl)-zirconiumdichloride,
- A-(2-isopropyl-4-phenyl-indenyl)(2-methyl-4-(p-tert-butyl-phenyl)indenyl)-zirconiumdichloride;
- A-(2-isopropyl-4-(p-tert-butyl-phenyl)indenyl)(2-methyl-4-phenyl-indenyl)-zirconiumdichloride,
- A-(2-isopropyl-4-(p-tert-butyl-phenyl)indenyl)(2,7-dimethyl-4-phenyl-indenyl)-zirconiumdichloride,
- A-(2-isopropyl-4-(p-tert-butyl-phenyl)indenyl)(2,5,6,7-tetramethyl-4-phenyl-indenyl)-zirconiumdichloride,
- A-(2-isopropyl-6-methyl-4-(p-tert-butyl-phenyl)indenyl) (2,6-dimethyl-4-phenyl-indenyl)-zirconiumdichloride,
- A-(2-isopropyl-4-phenyl-indenyl)(2,7-dimethyl-4-(p-tert-butyl-phenyl)indenyl)-zirconiumdichloride,
- A-(2-isopropyl-4-phenyl-indenyl)(2,5,6,7-tetramethyl-4-(p-tert-butyl-phenyl) indenyl)-zirconiumdichloride,
- A-(2-isopropyl-6-methyl-4-phenyl-indenyl)(2,6-dimethyl-4-(p-tert-butyl-phenyl) indenyl)-zirconiumdichloride,
- A-(2-isopropyl-4-(p-tert-butyl-phenyl)indenyl)(2-methyl-4-(4-naphthyl)-indenyl) indenyl)-zirconiumdichloride,
- A-(2-isopropyl-4-(4-naphthyl-indenyl)indenyl)(2-methyl-4-(p-tert-butyl-phenyl) indenyl)-zirconiumdichloride,
- A-bis(4-naphthyl-indenyl)zirconiumdichloride,
- A-bis(2-methyl-benzo-indenyl)zirconiumdichloride
- A-bis(2-methyl-indenyl)zirconiumdichloride,
- A-bis(2-methyl-4-(1-naphthyl)-indenyl)zirconiumdichloride,
- A-bis(2-methyl-4-(2-naphthyl)-indenyl)zirconiumdichloride,
- A-bis(2-methyl-4-phenyl-indenyl)zirconiumdichloride,
- A-bis(2-methyl-4-t-butyl-indenyl)zirconiumdichloride,
- A-bis(2-methyl-4-isopropyl-indenyl)zirconiumdichloride,
- A-bis(2-methyl-4-ethyl-indenyl)zirconiumdichloride,
- A-bis(2-methyl-4-acenaphth-indenyl)zirconiumdichloride,
- A-bis(2,4-dimethyl-indenyl)zirconiumdichloride,
- A-bis(2-ethyl-indenyl)zirconiumdichloride,
- A-bis(2-ethyl-4-ethyl-indenyl)zirconiumdichloride,
- A-bis(2-ethyl-4-phenyl-indenyl)zirconiumdichloride,
- A-bis(2-methyl-4,6 diisopropyl-indenyl)zirconiumdichloride,
- A-bis(2-methyl-4,5 diisopropyl-indenyl)zirconiumdichloride,
- A-bis(2,4,6-trimethyl-indenyl)zirconiumdichloride,
- A-bis(2,5,6-trimethyl-indenyl)zirconiumdichloride,
- A-bis(2,4,7-trimethyl-indenyl)zirconiumdichloride,
- A-bis(2-methyl-5-isobutyl-indenyl)zirconiumdichloride,
- A-bis(2-methyl-5-t-butyl-indenyl)zirconiumdichloride,
- A-bis(2-methyl-4-(tert-butyl-phenyl)-indenyl)zirconiumdichloride,
- A-bis(2-methyl-4-(4-methyl-phenyl)-indenyl)zirconiumdichloride,
- A-bis(2-methyl-4-(4-ethyl-phenyl)-indenyl)zirconiumdichloride,
- A-bis(2-methyl-4-(4-trifluoromethyl-phenyl)-indenyl)zirconiumdichloride,
- A-bis(2-methyl-4-(4-methoxy-phenyl)-indenyl)zirconiumdichloride,
- A-bis(2-ethyl-4-(4-tert-butyl-phenyl)-indenyl)zirconiumdichloride,
- A-bis(2-ethyl-4-(4-methyl-phenyl)-indenyl)zirconiumdichloride,
- A-bis(2-ethyl-4-(4-ethyl-phenyl)-indenyl)zirconiumdichloride,
- A-bis(2-ethyl-4-(4-trifluoromethyl-phenyl)-indenyl)zirconiumdichloride,
- A-bis(2-ethyl-4-(4-methoxy-phenyl)-indenyl)zirconiumdichloride,
- A-bis(2-methyl-4-(4-tert-butyl-phenyl)-indenyl)zirconiumdimethyl,
- A-bis(2-methyl-4-(4-methyl-phenyl)-indenyl)zirconiumdimethyl,
- A-bis(2-methyl-4-(4-ethyl-phenyl)-indenyl)zirconiumdimethyl,
- A-bis(2-methyl-4-(4-trifluoromethyl-phenyl)-indenyl)zirconiumdimethyl,
- A-bis(2-methyl-4-(4-methoxy-phenyl)-indenyl)zirconiumdimethyl,
- A-bis(2-ethyl-(4-tert-butyl-phenyl)-indenyl)zirconiumdimethyl,
- A-bis(2-ethyl-4-(4-methyl-phenyl)-indenyl)zirconiumdimethyl,
- A-bis(2-ethyl-4-(4-ethyl-phenyl)-indenyl)zirconiumdimethyl,
- A-bis(2-ethyl-4-(4-triflouromethyl-phenyl)-indenyl)zirconiumdimethyl,
- A-bis(2-ethyl-4-(4-methoxy-phenyl)-indenyl)zirconiumdimethyl,
- A-bis(2-isopropyl-4-(tert-butyl-phenyl)-indenyl)zirconiumdichloride,
- A-bis(2-isopropyl-4-(4-methyl-phenyl)-indenyl)zirconiumdichloride,
- A-bis(2-isopropyl-4-(4-ethyl-phenyl)-indenyl)zirconiumdichloride, A-bis(2-isopropyl-4-(4-trifluoromethyl-phenyl)-indenyl)zirconiumdichloride,
A-bis(2-isopropyl-4-(4-methoxy-phenyl)-indenyl)zirconiumdichloride,
A-bis(2-isopropyl-4-(4'-tert-butyl-phenyl)-indenyl)zirconiumdichloride,
A-bis(2-isopropyl-4-(4'-tert-butyl-phenyl)-indenyl)hafniumdichloride,
A-bis(2-isopropyl-4-(4'-tert-butyl-phenyl)-indenyl)titaniumdichloride,
A-bis(2-isopropyl-4-(4'-methyl-phenyl)-indenyl)zirconiumdichloride,
A-bis(2-isopropyl-4-(4'-n-propyl-phenyl)-indenyl)zirconiumdichloride,
A-bis(2-isopropyl-4-(4'-n-butyl-phenyl)-indenyl)zirconiumdichloride,
A-bis(2-isopropyl-4-(4'-hexyl-phenyl)-indenyl)zirconiumdichloride,
A-bis(2-isopropyl 1-4-(4'-sec-butyl-phenyl)-indenyl)zirconiumdichloride,
A-bis(2-isopropyl-4-phenyl)-indenyl)zirconiumdichloride,
A-bis(2-isopropyl-4-(4-methyl-phenyl)-indenyl)zirconiumdichloride,
A-bis(2-isopropyl-4-(4'-ethyl-phenyl)-indenyl)zirconiumdichloride,
A-bis(2-isopropyl-4-(4'-n-propyl-phenyl)-indenyl)zirconiumdichloride,
A-bis(2-isopropyl-4-(4'-n-butyl-phenyl)-indenyl)zirconiumdichloride,
A-bis(2-isopropyl-4-(4'-hexyl-phenyl)-indenyl)zirconiumdichloride,
A-bis(2-isopropyl-4-(4'-pentyl-phenyl)-indenyl)zirconiumdichloride,
A-bis(2-isopropyl-4-(4'-cyclohexyl-phenyl)-indenyl)zirconiumdichloride,
A-bis(2-isopropyl-4-(4'-sec-butyl-phenyl)-indenyl)zirconiumdichloride,
A-bis(2-isopropyl-4-(4'-tert-butyl-phenyl)-indenyl)zirconiumdichloride,
A-bis(2-ethyl-4-(4'-tert-butyl-phenyl)-indenyl)zirconiumdichloride,
A-bis(2-methyl-4-(4'-tert-butyl-phenyl)-indenyl)hafniumdichloride,
A-bis(2-methyl-4-(4'-tert-butyl-phenyl)-indenyl)titaniumdichloride,
A-bis(2-methyl-4-(4'-methyl-phenyl)-indenyl)zirconiumdichloride,
A-bis(2-methyl-4-(4'-n-propyl-phenyl)-indenyl)zirconiumdichloride,
A-bis(2-methyl-4-(4'-n-butyl-phenyl)-indenyl)zirconiumdichloride,
A-bis(2-methyl-4-(4'-hexyl-phenyl)-indenyl)zirconiumdichloride,
A-bis(2-methyl-4-(4'-sec-butyl-phenyl)-indenyl)zirconiumdichloride,
A-bis(2-ethyl-4-phenyl-indenyl)zirconiumdichloride,
A-bis(2-ethyl-4-(4'-methyl-phenyl)-indenyl)zirconiumdichloride,
A-bis(2-ethyl-4-(4'-ethyl-phenyl)-indenyl)zirconiumdichloride,
A-bis(2-ethyl-4-(4'-n-propyl-phenyl)-indenyl)zirconiumdichloride,
A-bis(2-ethyl-4-(4'-n-butyl-phenyl)-indenyl)zirconiumdichloride,
A-bis(2-ethyl-4-(4'-hexyl-phenyl)-indenyl)zirconiumdichloride,
A-bis(2-ethyl-4-(4'-pentyl-phenyl)-indenyl)zirconiumdichloride,
A-bis(2-ethyl-4-(4'-cyclohexyl-phenyl)-indenyl)zirconiumdichloride,
A-bis(2-ethyl-4-(4'-sec-butyl-phenyl)-indenyl)zirconiumdichloride,
A-bis(2-ethyl-4-(4'-tert-butyl-phenyl)-indenyl)zirconiumdichloride,
A-bis(2-n-propyl-4-phenyl-indenyl)zirconiumdichloride,
A-bis(2-n-propyl-4-(4'-methyl-phenyl)-indenyl)zirconiumdichloride,
A-bis(2-n-propyl-4-(4'-ethyl-phenyl)-indenyl)zirconiumdichloride,
A-bis(2-n-propyl-4-(4'-iso-propyl-phenyl)-indenyl)zirconiumdichloride,
A-bis(2-n-propyl-4-(4'-n-butyl-phenyl)-indenyl)zirconiumdichloride,
A-bis(2-n-propyl-4-(4'-hexyl-phenyl)-indenyl)zirconiumdichloride,
A-bis(2-n-propyl-4-(4'-cyclohexyl-phenyl)-indenyl)zirconiumdichloride,
A-bis(2-n-propyl-4-(4'-sec-butyl-phenyl)-indenyl)zirconiumdichloride,
A-bis(2-n-propyl-4-(4'-tert-butyl-phenyl)-indenyl)zirconiumdichloride,
A-bis(2-n-butyl-4-phenyl-indenyl)zirconiumdichloride,
A-bis(2-n-butyl-4-(4'-methyl-phenyl)-indenyl)zirconiumdichloride,
A-bis(2-n-butyl-4-(4'-ethyl-phenyl)-indenyl)zirconiumdichloride,
A-bis(2-n-butyl-4-(4'-n-propyl-phenyl)-indenyl)zirconiumdichloride,
A-bis(2-n-butyl-4-(4'-iso-propyl-phenyl)-indenyl)zirconiumdichloride,
A-bis(2-n-butyl-4-(4'-n-butyl-phenyl)-indenyl)zirconiumdichloride,
A-bis(2-n-butyl-4-(4'-hexyl-phenyl)-indenyl)zirconiumdichloride,
A-bis(2-n-butyl-4-(4'-cyclohexyl-phenyl)-indenyl)zirconiumdichloride,
A-bis(2-n-butyl-4-(4'-sec-butyl-phenyl)-indenyl)zirconiumdichloride,
A-bis(2-n-butyl-4-(4'-tert-butyl-phenyl)-indenyl)zirconiumdichloride,
A-bis(2-hexyl-4-phenyl-indenyl)zirconiumdichloride,
A-bis(2-hexyl-4-(4'-methyl-phenyl)-indenyl)zirconiumdichloride,
A-bis(2-hexyl-4-(4'-ethyl-phenyl)-indenyl)zirconiumdichloride,
A-bis(2-hexyl-4-(4'-n-propyl-phenyl)-indenyl)zirconiumdichloride,
A-bis(2-hexyl-4-(4'-iso-propyl-phenyl)-indenyl)zirconiumdichloride,
A-bis(2-hexyl-4-(4'-n-butyl-phenyl)-indenyl)zirconiumdichloride,
A-bis(2-hexyl-4-(4'-n-hexyl-phenyl)-indenyl)zirconiumdichloride,
A-bis(2-hexyl-4-(4'-cyclohexyl-phenyl)-indenyl)zirconiumdichloride,
A-bis(2-hexyl-4-(4'-sec-butyl-phenyl)-indenyl)zirconiumdichloride,
A-bis(2-hexyl-4-(4'-tert-butyl-phenyl)-indenyl)zirconiumdichloride,
A-bis(2-methyl-4-(4'-tert-butyl-phenyl)-indenyl)zirconiumbis(dimethylamine),
A-bis(2-ethyl-4-(4'-tert-butyl-phenyl)-indenyl)zirconiumdibenzyl, A-bis(2-methyl-4-(4'-tert-butyl-phenyl)-indenyl)zirconiumdimethyl,
A-(2-methyl-4-azapentalene)(2-methyl-4-(4'-methyl-phenyl)-indenyl) zirconiumdichloride,
A-(2-methyl-5-azapentalene)(2-methyl-4-(4'-methyl-phenyl)-indenyl) zirconiumdichloride,
A-(2-methyl-6-azapentalene)(2-methyl-4-(4'-methyl-phenyl)-indenyl) zirconiumdichloride,
A-(2-methyl-4-azapentalene)(2-methyl-4-(4'-ethyl-phenyl)-indenyl) zirconiumdichloride,
A-(2-methyl-4-thiapentalene)(2-methyl-4-(4'-n-propyl-phenyl)-indenyl)-zirconiumdichloride,
A-(2-methyl-4-azapentalene)(2-methyl-4-(4'-isopropyl-phenyl)-indenyl)-zirconiumdichloride,
A-(2-methyl-6-azapentalene)(2-methyl-4-(4'-isopropyl-phenyl)-indenyl)-zirconiumdichloride,
A-(2,5-dimethyl-6-thiapentalene)(2-methyl-4-(4'-isopropyl-phenyl)-indenyl)-zirconiumdichloride,
A-(2-methyl-6-oxapentalen)(2-methyl-4-(4'-isopropyl-phenyl)-indenyl) zirconiumdichloride,
A-(2-methyl-6-azapentalene)(2-methyl-4-(4'-n-butyl-phenyl)-indenyl) zirconiumdichloride,
A-(2-methyl-5-thiapentalene)(2-methyl-4-(4'-n-butyl-phenyl)-indenyl) zirconiumdichloride,
A-(2-methyl-4-oxapentalene)(2-methyl-4-(4'-n-butyl-phenyl)-indenyl) zirconiumdichloride,
A-(2-methyl-4-thiapentalene)(2-methyl-4-(4'-s-butyl-phenyl)-indenyl) zirconiumdichloride,
A-(2-methyl-4-oxapentalene)(2-methyl-4-(4'-s-butyl-phenyl)-indenyl) zirconiumdichloride,
A-(2-methyl-4-azapentalene)(2-methyl-4-(4'-tert-butyl-phenyl)-indenyl)-zirconiumdichloride,
A-(2-methyl-6-azapentalene)(2-methyl-4-(4'-tert-butyl-phenyl)-indenyl)-zirconiumdichloride,
A-(2-methyl-4-azapentalene)(2-methyl-4-(4'-n-pentyl-phenyl)-indenyl)-zirconiumdichloride,
A-(2-methyl-N-phenyl-6-azapentalene)(2-methyl-4-(4'-n-pentyl-phenyl)-indenyl)-zirconiumdichloride,
A-(2-methyl-4-oxapentalene)(2-methyl-4-(4'-n-pentyl-phenyl)-indenyl)-zirconiumdichloride,
A-(2-methyl-4-azapentalene)(2-methyl-4-(4'-n-hexyl-phenyl)-indenyl)-zirconiumdichloride,
A-(2-methyl-4-thiapentalene)(2-methyl-4-(4'-n-hexyl-phenyl)-indenyl)-zirconiumdichloride,
A-(2-methyl-6-thiapentalene)(2-methyl-4-(4'-n-hexyl-phenyl)-indenyl)-zirconiumdichloride,
A-(2,5-dimethyl-4-thiapentalene)(2-methyl-4-(4'-n-hexyl-phenyl)-indenyl)-zirconiumdichloride,
A-(2,5-dimethyl-6-thiapentalene)(2-methyl-4-(4'-n-hexyl-phenyl)-indenyl)-zirconiumdichloride,
A-(2,5-dimethyl-6-thiapentalene)(2-methyl-4-(4'-cyclohexyl-phenyl)-indenyl)-zirconiumdichloride,
A-(2-methyl-4-azapentalene)(2-methyl-4-(4'-trimethylsilyl-phenyl)-indenyl)-zirconiumdichloride,
A-(2-methyl-4-thiapentalene)(2-methyl-4-(4'-trimethylsilyl-phenyl)-indenyl)-zirconiumdichloride,
A-(2-methyl-5-thiapentalene)(2-methyl-4-(4'-trimethylsilyl-phenyl)-indenyl)-zirconiumdichloride,
A-(2-methyl-6-thiapentalene)(2-methyl-4-(4'-trimethylsilyl-phenyl)-indenyl)-zirconiumdichloride,
A-(2,5-dimethyl-4-azapentalene)(2-methyl-4-(4'-adamantyl-phenyl)-indenyl)-zirconiumdichloride,
A-(2-methyl-4-thiapentalene)(2-methyl-4-(4'-adamantyl-phenyl)-indenyl)-zirconiumdichloride,
A-(2-methyl-6-thiapentalene)(2-methyl-4-(4'-adamantyl-phenyl)-indenyl)-zirconiumdichloride,
A-(2,5-dimethyl-4-thiapentalene)(2-methyl-4-(4'-adamantyl-phenyl)-indenyl)-zirconiumdichloride,
A-(2-methyl-4-azapentalene)(2-methyl-4-(4'-tris(trifluoromethyl)methyl-phenyl)-indenyl)-zirconiumdichloride,
A-(2,5-dimethyl-4-azapentalene)(2-methyl-4-(4'-tris(trifluoromethyl)methyl-phenyl)-indenyl) zirconiumdichloride,
A-(2-methyl-4-thiapentalene)(2-methyl-4-(4'-tris(trifluoromethyl)methyl-phenyl)-indenyl)zirconiumdichloride,
A-(2-methyl-6-thiapentalene)(2-methyl-4-(4'-tris(trifluoromethyl)methyl-phenyl)-indenyl)zirconiumdichloride,
A-(2-methyl-4-azapentalene)(2-ethyl-4-(4'-tert-butyl-phenyl)-indenyl)-zirconiumdichloride,
A-(2-methyl-5-azapentalene)(2-n-butyl-4-(4'-tert-butyl-phenyl)-indenyl)-zirconiumdichloride,
A-(2-methyl-N-phenyl-6-azapentalene)(2-methyl-4-(4'-tert-butyl-phenyl)-indenyl)-zirconiumdichloride,
A-(2-methyl-4-azapentalene)(2-methylindenyl)zirconiumdichloride,
A-(2-methyl-N-phenyl-4-azapentalene)(2-methylindenyl)zirconiumdichloride,
A-(2-methyl-4-thiapentalene)(2-methylindenyl)zirconiumdichloride,
A-(2-methyl-5-thiapentalene)(2-methylindenyl)zirconiumdichloride,
A-(2-methyl-6-thiapentalene)(2-methylindenyl)zirconiumdichloride,
A-(2-methyl-4-azapentalene)(indenyl)zirconiumdichloride,
A-(2-methyl-5-azapentalene)(indenyl)zirconiumdichloride,
A-(2-methyl-6-azapentalene)(indenyl)zirconiumdichloride,
A-(2-methyl-N-phenyl-4-azapentalene)(indenyl)zirconiumdichloride,
A-(2-methyl-N-phenyl-5-azapentalene)(indenyl)zirconiumdichloride,
A-(2-methyl-N-phenyl-6-azapentalene)(indenyl)zirconiumdichloride,
A-(2,5-dimethyl-N-phenyl-6-azapentalene)(indenyl)zirconiumdichloride,
A-(2-methyl-4-thiapentalene)(indenyl)zirconiumdichloride,
A-(2-methyl-5-thiapentalene)(indenyl)zirconiumdichloride,
A-(2-methyl-6-thiapentalene)(indenyl)zirconiumdichloride,
A-(2,5-dimethyl-4-thiapentalene)(indenyl)zirconiumdichloride,
A-(2-methyl-4-azapentalene)(2-methyl-4-phenyl-indenyl)zirconiumdichloride,
A-(2-methyl-5-azapentalene)(2-methyl-4-phenyl-indenyl)zirconiumdichloride,
A-(2-methyl-6-azapentalene)(2-methyl-4-phenyl-indenyl)zirconiumdichloride,
A-(2-methyl-N-phenyl-4-azapentalene)(2-methyl-4-phenyl-indenyl) zirconiumdichloride,
A-(2-methyl-N-phenyl-5-azapentalene)(2-methyl-4-phenyl-indenyl) zirconiumdichloride,
A-(2-methyl-4-thiapentalene)(2-methyl-4-phenyl-indenyl)zirconiumdichloride,
A-(2-methyl-5-thiapentalene)(2-methyl-4-phenyl-indenyl)zirconiumdichloride, A-(2-methyl-6-thiapentalene)(2-methyl-4-phenyl-indenyl)zirconiumdichloride, A-(2-methyl-4-oxapentalene)(2-methyl-4-phenyl-indenyl)zirconiumdichloride, A-(2-methyl-4-azapentalene)(2-methyl-4,5-benzo-indenyl)zirconiumdichloride, A-(2-methyl-N-phenyl-4-azapentalene)(2-methyl-4,5-benzo-indenyl) zirconiumdichloride, A-(2-methyl-N-phenyl-5-azapentalene)(2-methyl-4,5-benzo-indenyl) zirconiumdichloride, A-(2-methyl-N-phenyl-6-azapentalene)(2-methyl-4,5-benzo-indenyl) zirconiumdichloride, A-bis(2-methyl-4-azapentalene)zirconiumdichloride, A-bis(2-methyl-N-phenyl-4-azapentalene)zirconiumdichloride, A-bis(2-methyl-4-thiapentalene)zirconiumdichloride, wherein A is selected from the group consisting of structural isomers of Dipropylsilanediyl, Dibutylsilanediyl, Dipentylsilanediyl, Dihexylsilanediyl, Diheptylsilanediyl, Dioctylsilanediyl, Dinonylsilanediyl, Didecylsilanediyl, Diundecylsilanediyl, Didodecylsilanediyl, Di(cyclopentyl)silanediyl, Cyclohexyl(methyl)silanedyl, Dipropylgermanediyl, Dibutylgermanediyl, Dipentylgermanediyl, Dihexylgermanediyl, Diheptylgermanediyl, Dioctylgermanediyl, Dinonylgermanediyl, Didecylgermanediyl, Diundecylgermanediyl or Didodecylgermanediyl, Hexyl(methyl)germanediyl, Butyl(methyl)silanediyl, Butyl(ethyl)silanediyl, Butyl(propyl)silanediyl, Pentyl(methyl)silanediyl, Pentyl(ethyl)silanediyl, Pentyl(propyl)silanediyl, Hexyl(methyl)silanediyl, Hexyl(ethyl)silanediyl and Hexyl(propyl)silanediyl.

28. The composition of claim 27 where the units A are:
Di-n-propylsilanediyl, Di-n-butylsilanediyl, Di-n-pentylsilanediyl, Di(cyclopentyl)silanediyl, Di-n-hexylsilanediyl, Cyclohexyl(methyl)silanediyl, (n-butyl)(methyl)silanediyl or (n-hexyl)(methyl)silanediyl.

29. A process for the production of a mixture of racemic and meso isomers of metallocene compounds comprising the steps of:

a) providing a ligand system of the formula

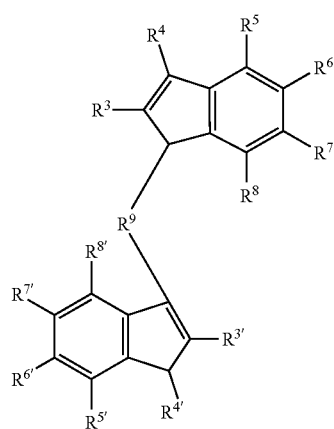

(formula LS)

wherein
$R^9$ is a bridge having one of the structures:

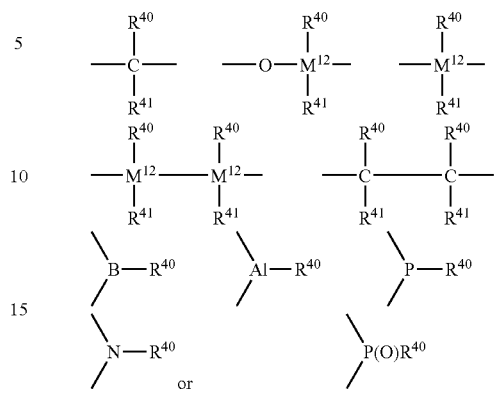

or where $R^{40}$ and $R^{41}$, can be identical or different, with or without heteroatoms, when $R^{40}$ and $R^{41}$ are identical they are selected from the group consisting of an alkyl group having from 2 to about 30 carbon atoms, a fluoroalkyl group of from 2 to about 10 carbon atoms, an alkoxy group of from 2 to about 10 carbon atoms, an aryloxy group of from 6 to about 10 carbon atoms, an alkenyl group of from about 3 to about 10 carbon atoms, an arylalkyl group of from 7 to about 40 carbon atoms, an alkylaryl group of from 7 to about 40 carbon atoms, a substituted or unsubstituted alkylsilyl or arylsilyl group, or an arylalkenyl group of from 8 to about 40 carbon atoms, when $R^{40}$ and $R^{41}$ are different one of either $R^{40}$ and $R^{41}$ is selected from the group consisting of an alkyl group having from 4 to about 40 carbon atoms, a fluoroalkyl group of from 2 to about 10 carbon atoms, an alkoxy group of from 2 to about 10 carbon atoms, an aryloxy group of from 6 to about 10 carbon atoms, an alkenyl group of from 3 to about 10 carbon atoms, an arylalkyl group of from 7 to about 40 carbon atoms, an alkylaryl group of from 7 to about 40 carbon atoms, a substituted or unsubstituted alkylsilyl or arylsilyl group and an arylalkenyl group of from 8 to about 40 carbon atoms, and the other of $R^{40}$ and $R^{41}$ is selected from the group consisting of an alkyl group having from 1 to 40 carbon atoms, a fluoroalkyl group of from 2 to about 10 carbon atoms, an alkoxy group of from 2 to about 10 carbon atoms an aryloxy group of from 6 to about 10 carbon atoms, an alkenyl group of from 3 to about 10 carbon atoms, an arylalkyl group of from 7 to about 40 carbon atoms, an alkylaryl group of from 7 to about 40 carbon atoms, a substituted or unsubstituted alkylsilyl or arylsilyl group and an arylalkenyl group of from 8 to about 40 carbon atoms, $M^{12}$ is silicon, germanium or tin, and $R^3$, $R^4$, $R^5$, $R^6$, $R^7$, $R^8$ and also $R^{3'}$, $R^{4'}$, $R^{5'}$, $R^{6'}$, $R^{7'}$ and $R^{8'}$ are identical or different and are each a hydrogen atom, or a linear, cyclic or branched group, with or without heteroatoms, selected from the group consisting of an alkyl group of from 1 to about 10 carbon atoms, an alkenyl group of from 2 to about 10 carbon atoms, an aryl group of from 6 to about 20 carbon atoms, an arylalkyl group of from 7 to about 40 carbon atoms, an alkylaryl group of from 7 to about 40 carbon atoms or an arylalkenyl group of from 8 to about 40 carbon atoms, a substituted or unsubstituted alkylsilyl or arylsilyl group, with the proviso that $R^3$ and $R^{3'}$ are not hydrogen, or wherein two adjacent radicals $R^5$, $R^6$ or $R^{5'}$, $R^{6'}$, or $R^6$, $R^7$ or $R^{6'}$, $R^{7'}$, or $R^7$, $R^8$ or $R^{7'}$, $R^{8'}$ can form one or more hydrocarbon ring system(s), wherein said ligand system is produced by deprotonation of a compound of the formula

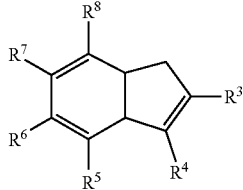

(formula 2)

with a base in an inert solvent at temperatures of −70° C. to 80° C.; and,
b) combining said ligand system of formula LS with a compound having the formula $M^1X_4$ at a temperature of from about −70° C. to about 80° C., wherein $M^1$ is zirconium, titanium or hafnium and X is a halogen, to provide a metallocene compound(s) having a weight ratio of racemic to meso isomers of greater than 5:1 as synthesized.

30. The process of claim 29 wherein the weight ratio of racemic to meso isomers is greater than 10:1 without any further separation of racemic from meso isomers.

31. The process of claim 29 wherein the weight ratio of racemic to meso isomers is greater than 15:1 without any further separation of racemic from meso isomers.

32. The process of claim 29 wherein the weight ratio of racemic to meso isomers is greater than 20:1 without any further sepration of racemic isomers from meso isomers.

33. A catalyst composition comprising:
a) mixed isomers of at least one metallocene compound having the formula 1a:

$$R^9L^1L^2M^1R^1R^2 \quad \text{(formula 1a)}$$

where $L^1$ and $L^2$ are identical or different ligands and are each a substituted mononuclear or polynuclear hydrocarbon radical selected from the group consisting of substituted cyclopentadienyl, indenyl, tetrahydroindenyl, azurenyl, fluorenyl, azapentalenyl, thiapentalenyl or oxapentalenyl, which form a sandwich structure with atom $M^1$, therebetween, $R^1$ and $R^2$ are identical or different and are each a hydrogen atom, an alkyl group of from 1 to about 10 carbon atoms, an alkoxy group of from 1 to about 10 carbon atoms, an aryl group of from 6 to about 20 carbon atoms, an aryloxy group of from about 6 to about 10 carbon atoms, an alkenyl group of from 2 to about 10 carbon atoms, an OH group, a halogen atom, or a $NR^{232}$ group, where $R^{32}$ is an alkyl group of from 1 to about 10 carbon atoms or an aryl group of from 6 to about 14 carbon atoms, or $R^1$ and $R^2$ form one or more ring system(s), $M^1$ is a metal of group IVb of the Periodic Table of the Elements, $R^9$ is a bridge between the ligands $L^1$ and $L^2$ having one of the structures:

-continued

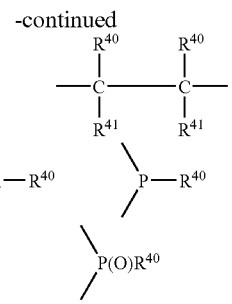

where $R^{40}$ and $R^{41}$, are identical or different, with or without heteroatoms, when $R^{40}$ and $R^{41}$ are identical they are selected from the group consisting of an alkyl group having from 2 to about 30 carbon atoms, a fluoroalkyl group of from 2 to about 10 carbon atoms, an alkoxy group of from 2 to about 10 carbon atoms, an aryloxy group of from 6 to about 10 carbon atoms, an alkenyl group of from about 3 to about 10 carbon atoms, an arylalkyl group of from 7 to about 40 carbon atoms, an alkylaryl group of from 7 to about 40 carbon atoms, a substituted or unsubstituted alkylsilyl or arylsilyl group and an arylalkenyl group of from 8 to about 40 carbon atoms, when $R^{40}$ and $R^{41}$ are different one of either $R^{40}$ and $R^{41}$ is selected from the group consisting of an alkyl group having from 4 to about 40 carbon atoms, a fluoroalkyl group of from 2 to about 10 carbon atoms, an alkoxy group of from 2 to about 10 carbon atoms, an aryloxy group of from 6 to about 10 carbon atoms, an alkenyl group of from 3 to about 10 carbon atoms, an arylalkyl group of from 7 to about 40 carbon atoms, an alkylaryl group of from 7 to about 40 carbon atoms, a substituted or unsubstituted alkylsilyl or arylsilyl group and an arylalkenyl group of from 8 to about 40 carbon atoms, and the other of $R^{40}$ and $R^{41}$ is selected from the group consisting of an alkyl group having from 1 to 40 carbon atoms, a fluoroalkyl group of from 2 to about 10 carbon atoms, an alkoxy group of from 2 to about 10 carbon atoms an aryloxy group of from 6 to about 10 carbon atoms, an alkenyl group of from 3 to about 10 carbon atoms, an arylalkyl group of from 7 to about 40 carbon atoms, an alkylaryl group of from 7 to about 40 carbon atoms, a substituted or unsubstituted alkylsilyl or arylsilyl group and an arylalkenyl group of from 8 to about 40 carbon atoms, M2 is silicon, germanium or tin, and
wherein the compound as synthesized has a ratio of racemic or pseudoracemic isomers to meso or pseudomeso isomers of greater than 5:1;
b) at least one cocatalyst; and
c) at least one porous support.

34. The catalyst composition of claim 33 wherein the cocatalyst is an aluminoxane having one of the following formulas

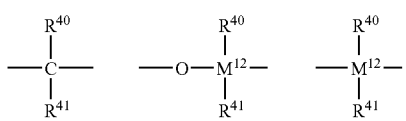

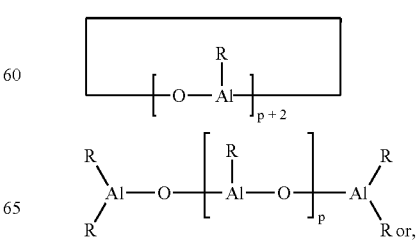

-continued

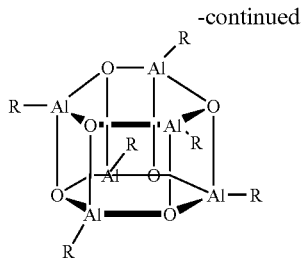

wherein R is hydrogen, an alkyl group of from 1 to about 6 carbon atoms, an aryl group of from 6 to about 18 carbon atoms, or benzyl, and p is an integer from 2 to 50.

35. The catalyst composition system of claim 34 wherein the atomic ratio of aluminum from the aluminoxane to the metal $M^1$ of the metallocene ranges from about 10:1 to about 1000:1.

36. The catalyst composition of claim 33 wherein the cocatalyst is a Lewis acid having the formula $$M^2X^1X^2X^3$$

wherein $M^2$ is selected from boron, aluminum or gallium, and $X^1$, $X^2$ and $X^3$ are the same or different and are each individually hydrogen, an alkyl group of from 1 to about 20 carbon atoms, an aryl group of from 6 to about 15 carbon atoms, or an alkaryl, aralkyl, halo-alkyl or haloaryl group having 1 to about 10 carbon atoms in the alkyl radical and from 6 to about 20 carbon atoms in the aryl radical, wherein the halogen component can be fluorine, chlorine, bromine or iodine.

37. The catalyst composition of claim 33 wherein the Lewis acid is selected from the group consisting of trimethylaluminium, triethylaluminum, triisobutylaluminum, tributylaluminum, trifluoroborane, triphenylborane, tris(4-fluorophenyl)borane, tris(3,5-difluorophenyl)borane, tris(4-fluoromethylphenyl)borane, tris(2,4,6-trifluorophenyl)borane, tris(pentafluorophenyl)borane, tritolylborane, tris(3,5-dimethyl-phenyl)borane, tris(3,5-difluorophenyl)borane and tris (3,4,5-trifluorophenyl)borane.

38. The catalyst composition of claim 33 wherein the cocatalyst is an ionic compound containing a non-coordinating anion selected from the group consisting of tetrakis (pentafluorophenyl)borate, tetraphenylborate, $SbF_6^-$, $CF_3SO_3^-$ and $ClO_4^-$.

39. The catalyst composition of claim 33 wherein the porous support is selected from the group consisting of inorganic oxides, inorganic salts, and polymer powders.

40. The catalyst composition of claim 33 wherein the porous support is selected from the group consisting of silica, alumina, aluminosilicates, zeolites, MgO, $ZrO_2$, $TiO_2$, $B_2O_3$, CaO, ZnO, $ThO_2$, $Na_2O$, $K_2O$, $Li_2O$, $Na_2CO_3$, $K_2CO_3$, $CaCO_3$, $MgCl_2$, $Na_2SO_4$, $Al_2(SO_4)_3$, $BaSO_4$, $KNO_3$, $Mg(NO_3)_2$; $Al(NO_3)_3$ and combinations thereof.

41. The catalyst system of claim 33 wherein the porous support is selected from the group consisting of polyethylene, polypropylene, polybutene, polystyrene, divinylbenzene crosslinked polystyrene, polyvinyl chloride, acrylonitrile-butadiene-styrene copolymer, polyamide, polymethacrylate, polycarbonate, polyester, polyacetal and polyvinyl alcohol.

42. The catalyst composition of claim 33 wherein the cocatalyst is a reaction product of at least one compound of formulas (C) and/or (D) and/or (E) with at least one compound of formula (F),

where $R^{27}$ is a hydrogen atom or a boron-free $C_1$-$C_{40}$ carbon-containing group, selected from an alkyl group of from 1 to about 20 carbon atoms, an aryl group of from 6 to about 20 carbon atoms, an arylalkyl group of from 7 to about 40 carbon atoms or an alkylaryl group of from 7 to about 40 carbon atoms, R7 and $R^{18}$ are the same or different and are a hydrogen atom, a halogen atom, or a $C_1$-$C_{40}$ carbon-containing group, selected from an alkyl group of from 1 to about 20 carbon atoms, a haloalkyl group of from 1 to about 20 carbon atoms, an alkoxy group of from 1 to about 10 carbon atoms, an aryl group of from 6 to about 20 carbon atoms, a haloaryl group of from 6 to about 20 carbon atoms, an aryloxy group of from 6 to about 20 carbon atoms, an arylalkyl group of from 7 to about 40 carbon atoms, a haloarylalkyl group of from 7 to about 40 carbon atoms, an alkylaryl group of from 7 to about 40 carbon atoms or a haloalkylaryl group of from 7 to about 40 carbon atoms or $R^{17}$ may also be an —$OSiR_{51_3}$ group, in which the $R^{51}$ groups are the same or different and are each a hydrogen atom, a halogen atom, or a $C_1$-$C_{40}$ carbon-containing group, selected from an alkyl group of from 1 to about 20 carbon atoms, a haloalkyl group of from 1 to about 20 carbon atoms, an alkoxy group of from 1 to about 10 carbon atoms, an aryl group of from 6 to about 20 carbon atoms, a haloaryl group of from 6 to about 20 carbon atoms, an aryloxy group of from 6 to about 20 carbon atoms, an arylalkyl group of from 7 to about 40 carbon atoms, a haloarylalkyl group of from 7 to about 40 carbon atoms, an alkylaryl group of from 7 to about 40 carbon atoms or a haloaryalkyl group of from 7 to about 40 carbon atoms.

D is an element of main Group VI of the periodic table of elements or an $NR^{61}$ group, where $R^{61}$ is a hydrogen atom or a $C_1$-$C_{20}$ hydrocarbon group, selected from an alkyl group of from 1 to about 20 carbon atoms or an aryl group of from 6 to about 20 carbon atoms, f is a whole number from 0 to 3, g is a whole number from 0 to 3 with f+g not equal to 0, and h is a whole number from 1 to 10.

43. The catalyst composition of claim 33 wherein the cocatalyst is a compound or a mixture of compounds of formulas (A) and/or (B)

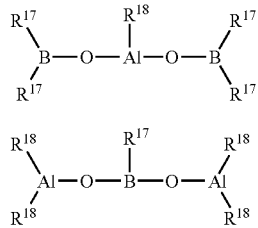

(A)

(B)

where $R^{17}$ and $R^{18}$ are the same or different and are a hydrogen atom, a halogen atom, a $C_1$-$C_{40}$ carbon-containing group, selected from an alkyl group of from 1 to about 20 carbon atoms, a haloalkyl group of from 1 to about 20 carbon atoms, an alkoxy group of from 1 to about 10 carbon atoms, an aryl group of from 6 to about 20 carbon atoms, a haloaryl group of from 6 to about 20 carbon atoms, an aryloxy group of from 6 to about 20 carbon atoms, an arylalkyl group of from 7 to about 40 carbon atoms, a haloarylalkyl group of from 7 to about 40 carbon atoms, an alkylaryl group of from 7 to about 40 carbon atoms or a haloalkylaryl group of from 7 to about 40 carbon atoms or $R^{17}$ may also be an —$OSiR^{51}{}_3$ group, where the $R^{51}$ groups are the same or different and are each a hydrogen atom, a halogen atom, a $C_1$-$C_{40}$ carbon-containing group, selected from an alkyl group of from 1 to about 20 carbon atoms, a haloalkyl group of from 1 to about 20 carbon atoms, an alkoxy group of from 1 to about 10 carbon atoms, an aryl group of from 6 to about 20 carbon atoms, a haloaryl group of from 6 to about 20 carbon atoms, an aryloxy group of from 6 to about 20 carbon atoms, an arylalkyl group of from 7 to about 40 carbon atoms, a haloarylalkyl group of from 7 to about 40 carbon atoms, an alkylaryl group of from 7 to about 40 carbon atoms or a halo alkylaryl group of from 7 to about 40 carbon atoms.

44. The catalyst composition of claim 33 wherein the cocatalyst is a compound or a mixture of compounds of the following formulas

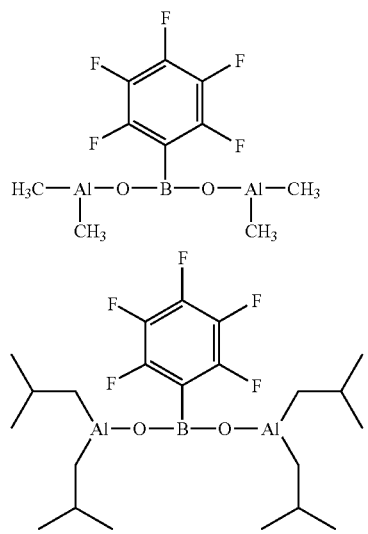

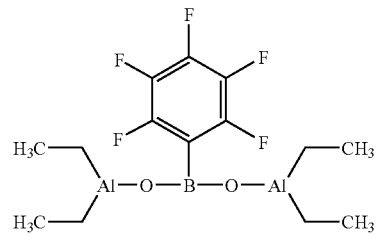

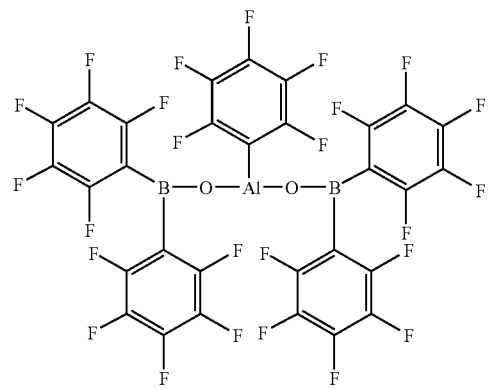

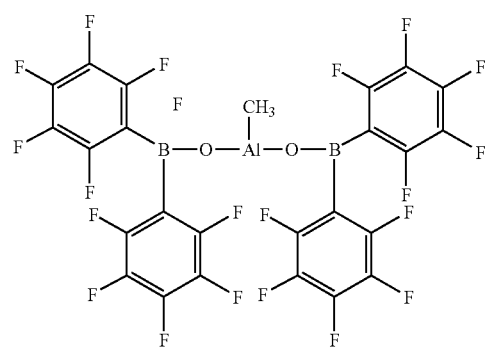

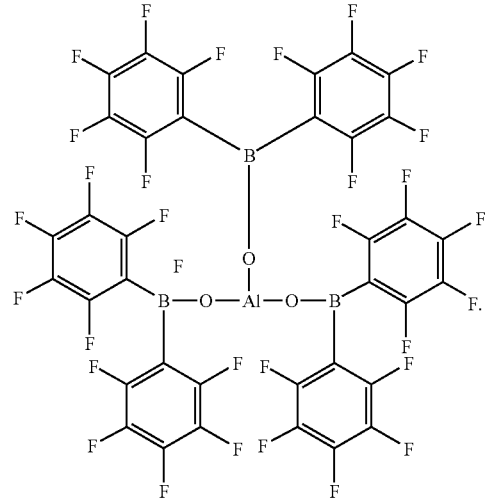

45. The catalyst composition of claim 33 wherein the cocatalyst is

[chemical structure: (C6F5)2B—O—Al(CH3)—O—B(C6F5)2]

46. The catalyst composition of claim 33 wherein the cocatalyst is

[chemical structure: tris-borate aluminum complex with pentafluorophenyl groups]

47. A process for the polymerization of olefins comprising contacting one or more olefins each having from about 2 to about 20 carbon atoms under polymerization reaction conditions with the catalyst composition of claim 42.

48. A process for the polymerization of olefins comprising contacting one or more olefins each having from about 2 to about 20 carbon atoms under polymerization reaction conditions with the catalyst composition of claim 43.

49. A process for the polymerization of olefins comprising contacting one or more olefins each having from about 2 to about 20 carbon atoms under polymerization reaction conditions .with the catalyst composition of claim 44.

50. A process for the polymerization of olefins comprising contacting one or more olefins each having from about 2 to about 20 carbon atoms under polymerization reaction conditions with the catalyst composition of claim 45.

51. A process for the polymerization of olefins comprising contacting one or more olefins each having from about 2 to about 20 carbon atoms under polymerization reaction conditions with the catalyst composition of claim 46.

52. A process for the polymerization of olefins comprising contacting one or more olefins each having from about 2 to about 20 carbon atoms under polymerization reaction conditions with the catalyst composition of claim 33.

53. A process for the polymerization of olefins comprising contacting one or more olefins each having from 2 to about 20 carbon atoms under polymerization reaction conditions with the catalyst composition of claim 34.

54. A process for the polymerization of olefins comprising contacting one or more olefins each having from 2 to about 20 carbon atoms under polymerization reaction conditions with the catalyst composition of claim 35.

55. A process for the polymerization of olefins comprising contacting one or more olefins each having from 2 to about 20 carbon atoms under polymerization reaction conditions with the catalyst composition of claim 36.

56. A process for the polymerization of olefins comprising contacting one or more olefins each having from 2 to about 20 carbon atoms under polymerization reaction conditions with the catalyst composition of claim 37.

57. A process for the polymerization of olefins comprising contacting one or more olefins each having from 2 to about 20 carbon atoms under polymerization reaction conditions with the catalyst composition of claim 38.

58. A process for the polymerization of olefins comprising contacting one or more olefins each having from 2 to about 20 carbon atoms under polymerization reaction conditions with the catalyst composition of claim 39.

59. A process for the polymerization of olefins comprising contacting one or more olefins each having from 2 to about 20 carbon atoms under polymerization reaction conditions with the catalyst composition of claim 40.

60. A process for the polymerization of olefins comprising contacting one or more olefins each having from 2 to about 20 carbon atoms under polymerization reaction conditions with the catalyst composition of claim 41.

61. The process of claim 52 wherein at least one olefin is a 1-olefin.

62. The process of claim 52 wherein at least one olefin has the formula $$R'''\!-\!CH\!=\!CH\!-\!R''$$

wherein $R'''$ and $R''$ can be identical or different and are each individually a hydrogen atom or a radical having from 1 to about 20 carbon atoms or $R'''$ and $R''$ together can form one or more rings.

63. The process of claim 52 wherein the olefins include ethylene and one or more 1-olefins having from 4 to about 20 carbon atoms.

64. The process of claim 52 wherein the olefins include propylene.

65. The process of claim 52 wherein the olefins include propylene and ethylene.

66. The process of claim 52 wherein the olefins include propylene and one or more 1-olefins having from 4 to about 20 carbon atoms.

67. The process of claim 52 wherein the olefins include propylene, ethylene and one or more 1-olefins having from 4 to about 20 carbon atoms.

68. A process for the polymerization of olefins comprising:
    contacting one or more olefins each having from 2 to about 20 carbon atoms under polymerization reaction conditions with a catalyst composition including at least one compound having the formula 1 a as set forth in claim 1.

69. A process for the polymerization of olefins comprising:
    contacting one or more olefins each having from 2 to about 20 carbon atoms under polymerization reaction conditions with a catalyst composition including at least one compound having the formula 1b as set forth in claim 9.

70. A process for the polymerization of olefins comprising:

contacting one or more olefins each having from 2 to about 20 carbon atoms under polymerization reaction conditions with a catalyst composition including at least one compound having the formula 1c as set forth in claim 15.

71. A process for the polymerization of olefins comprising:

contacting one or more olefins each having from 2 to about 20 carbon atoms under polymerization reaction conditions with a catalyst composition including at least one compound having the formula 1d as set forth in claim 22.

* * * * *